(12) United States Patent
Lee et al.

(10) Patent No.: US 11,001,841 B2
(45) Date of Patent: May 11, 2021

(54) CCCTC-BINDING FACTOR (CTCF) RNA INTERACTOME

(71) Applicant: The General Hospital Corporation, Boston, MA (US)

(72) Inventors: Jeannie T. Lee, Boston, MA (US); Johnny Kung, Boston, MA (US); Barry Kesner, Charlestown, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/952,679

(22) Filed: Apr. 13, 2018

(65) Prior Publication Data
US 2019/0309291 A1    Oct. 10, 2019

Related U.S. Application Data

(63) Continuation of application No. 14/735,930, filed on Jun. 10, 2015, now abandoned.

(60) Provisional application No. 62/010,342, filed on Jun. 10, 2014.

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/14* (2013.01); *C12N 2310/315* (2013.01); *C12N 2310/3231* (2013.01); *C12N 2310/341* (2013.01); *C12N 2310/531* (2013.01)

(58) Field of Classification Search
None
See application file for complete search history.

(56) References Cited

U.S. PATENT DOCUMENTS

| | | |
|---|---|---|
| 2004/0146902 A1 | 7/2004 | Ecker |
| 2005/0266422 A1 | 12/2005 | Vagle et al. |
| 2009/0215872 A1 | 8/2009 | Lee |
| 2009/0264503 A1 | 10/2009 | Chiang |
| 2011/0098342 A1 | 4/2011 | Ramadass et al. |

FOREIGN PATENT DOCUMENTS

| | | |
|---|---|---|
| WO | WO 2012/065143 | 5/2012 |
| WO | WO 2012/087983 | 6/2012 |
| WO | WO 2013/173608 | 11/2013 |

OTHER PUBLICATIONS

Bacher et al., "Transient colocalization of X-inactivation centres accompanies the initiation of X inactivation," Nat Cell Biol, 8:293-299, Jan. 24, 2006.
Bell and Felsenfeld, "Methylation of a CTCF-dependent boundary controls imprinted expression of the Igf2 gene," Nature, 405:482-485, May 25, 2000.
Berletch, et al., "Genes that escape from X inactivation," Hum Genet, 130(2):237-245, Aug. 2011.
Calabrese et al., "Site-specific silencing of regulatory elements as a mechanism of X inactivation," Cell 151(5):951-963, Nov. 21, 2012.
Carrel and Willard, "X-inactivation profile reveals extensive variability in X-linked gene expression in females," Nature, 434:400-404, Mar. 17, 2005.
Chao et al., "CTCF, a candidate trans-acting factor for X-inactivation choice," Science, 295(5553):345-347, Jan. 2002.
Chen et al., "Comprehensive identification and annotation of cell type-specific and ubiquitous CTCF-binding sites in the human genome," PLoS ONE, 7, e41374, Jul. 19, 2012.
Cifuentes-Rojas et al., "Regulatory interactions between RNA and Polycomb repressive complex 2," Molecular Cell ePub 55(2):171-185, Jul. 17, 2014.
Davidovich et al., "Promiscuous RNA binding by Polycomb repressive complex 2," Nature structural & molecular biology 20:1250-1257, Sep. 2013.
DeMare et al., "The genomic landscape of cohesin-associated chromatin interactions," Genome Res 23:1224-1234, May 2013.
Disteche, "Dosage compensation of the sex chromosomes," Annual Review of Genetics 46:537-560, Sep. 2012.
Dixon et al., "Topological domains in mammalian genomes identified by analysis of chromatin interactions," Nature, 485:376-380, May 17, 2012.
Donohoe et al., "Identification of a Ctcf cofactor, Yyl, for the X chromosome binary switch," Mol Cell 25(1):43-56, Jan. 12, 2007.
Donohoe et al., "The pluripotency factor Oct4 interacts with Ctcf and also controls X-chromosome pairing and counting," Nature 460:128-132, Jul. 2009.
Filippova "Genetics and epigenetics of the multifunctional protein CTCF," Curr Top Dev Biol 80:337-360, Oct. 2013.
Filippova et al., "Boundaries between Chromosomal domains of X inactivation and escape bind CTCF and lack CpG methylation during early development," Dev Cell, 8(1):31-42, Jan. 2005.
Handoko et al., "CTCF-mediated functional chromatin interactome in pluripotent cells," Nat Genet, 43:630-638, Jul. 2011.
Hark e al., "CTCF mediates methylation-sensitive enhancer-blocking activity at the H19/Igf2 locus," Nature, 405:486-489, May 2000.
Heard and Disteche "Dosage compensation in mammals: fine-tuning the expression of the X chromosome," Genes Dev, 20(14):1848-1867, Jul. 15, 2006.
Heintzman et al., "Histone modifications at human enhancers reflect global cell-type-specific gene expression," Nature, 459:108-112, May 7, 2009.

(Continued)

*Primary Examiner* — Kimberly Chong
(74) *Attorney, Agent, or Firm* — Fish & Richardson P.C.

(57) ABSTRACT

This invention relates to methods and compositions for selectively reactivating or downregulating certain genes, e.g., genes regulated by zinc-finger protein CCCTC-binding factor (CTCF) on autosomes (e.g., imprinted genes, tumor suppressors, cancer) and the inactive X chromosome (Xi), e.g., genes associated with X-linked diseases, e.g., Rett Syndrome, Factor VIII or IX deficiency, Fragile X Syndrome, Duchenne muscular dystrophy, and PNH, in heterozygous females carrying a mutated allele, in addition to a functional wildtype or hypomorphic allele.

16 Claims, 26 Drawing Sheets

Specification includes a Sequence Listing.

(56) References Cited

OTHER PUBLICATIONS

International Preliminary Report on Patentability in International Application No. PCT/US2015/035204, dated Dec. 22, 2016, 9 pages.
International Search Report and Written Opinion in International Application No. PCT/US2015/35204, dated Dec. 7, 2015, 19 pages.
Jensen, and Darnell, "CLIP: crosslinking and immunoprecipitation of in vivo RNA targets of RNA-binding proteins," Methods Mol Biol, 488:85-98, 2008.
Jeon and Lee, "YY1 Tethers Xist RNA to the Inactive X Nucleation Center," Cell, 146(1):119-133, Jul. 8, 2011.
Kanduri et al., "A differentially methylated imprinting control region within the Kcnq1 locus harbors a methylation-sensitive chromatin insulator," J Biol Chem, 277(20):18106-18110, May 17, 2002.
Kharchenko et al., "Design and analysis of ChIP-seq experiments for DNA-binding proteins," Nat Biotech, 26:1351-1359, Nov. 2008.
Kim et al., "Analysis of the vertebrate insulator protein CTCF-binding sites in the human genome," Cell, 128(6):1231-1245, Mar. 23, 2007.
Kung et al., "Long noncoding RNAs: Past, present, and future," Genetics 193(3):651-669, Mar. 1, 2013.
Lai et al., "Activating RNAs associate with Mediator to enhance chromatin architecture and transcription," Nature, 494:497-501, Feb. 2013.
Lanz et al., "A steroid receptor coactivator, SRA, functions as an RNA and is present in an SRC-1 complex," Cell, 97(1):17-27, Apr. 2, 1999.
Lee and Bartolomei, "X-Inactivation, Imprinting, and Long Noncoding RNAs in Health and Disease," Cell, 152(6):1308-1323, Mar. 14, 2013.
Lee and Lu, "Targeted mutagenesis of Tsix leads to nonrandom X inactivation," Cell, 99(1):47-57, Oct. 1, 1999.
Lee et al., "Tsix, a gene antisense to Xist at the X-inactivation centre," Nat Genet, 21:400-404, May 1999.
Li and Carrel, "Escape from X chromosome inactivation is an intrinsic property of the Jarid1c locus," Proc Natl Acad Sci USA, 105(44):17055-17060, Nov. 4, 2008.
Li et al., "Functional roles of enhancer RNAs for oestrogen-dependent transcriptional activation," Nature, 498:516-520, Jun. 27, 2013.
Li et al., "TCF regulates allelic expression of Igf2 by orchestrating a promoter-polycomb repressive complex 2 interchromosomal loop," Mol Cell Biol, 28(20):6473-6482, Oct. 2008.
Ling et al., "CTCF mediates interchromosomal colocalization between Igf2/H19 and Wsb1/Nf1," Science, 312(5771):269-272, Apr. 14, 2006.
Lobanenkov et al., "A novel sequence-specific DNA binding protein which interacts with three regularly spaced direct repeats of the CCCTC-motif in the 5' flaking sequence of the chicken c-myc gene," Oncogene, 5:1743-1753, 1991.
Lyon, "X-chromosome inactivation and human genetic disease," Acta Paediatr Suppl, 91(s439):107-112, Nov. 2002.
MacPherson et al., "The CTCF Insulator Protein Is Posttranslationally Modified by SUMO," Mol Cell Biol, 29(3):714-25, Feb. 2009.
Masui et al., "Live-cell chromosome dynamics and outcome of X chromosome pairing events during ES cell differentiation," Cell, 145(3):447-458, Apr. 29, 2011.
Mugford et al., "Evidence for Local Regulatory Control of Escape from Imprinted X Chromosome Inactivation," Genetics, 197(2)715-723, Mar. 19, 2014.
Nakahashi, et al. "A genome-wide map of CTCF multivalency redefines the CTCF code," Cell Rep, 3(5):1678-1689, May 30, 2013.
Navarro et al., "Molecular coupling of Tsix regulation and pluripotency," Nature, 468:457-460, Nov. 18, 2010.
Nora et al., "Spatial partitioning of the regulatory landscape of the X-inactivation centre," Nature, 485:381-385, Apr. 11, 2012.

Ogawa and Lee, "Xite, X-inactivation intergenic transcription elements that regulate the probability of choice," Mol Cell, 11(3):731-743, Mar. 2003.
Ogawa et al., "Intersection of the RNA interference and X-inactivation pathways," Science, 320(5881):1336-1341, Jun. 6, 2008.
Ohlsson et al., "CTCF is a uniquely versatile transcription regulator linked to epigenetics and disease," Trends Genet, 7(9):520-527, Sep. 1, 2001.
Ohlsson et al., "Does CTCF mediate between nuclear organization and gene expression?" BioEssays, 32(1):37-50, Jan. 2010.
Ong and Corces "CTCF: an architectural protein bridging genome topology and function," Nat Rev Genet, 15:234-246, Nov. 11, 2014.
Palstra et al., "The β-globin nuclear compartment in development and erythroid differentiation," Nat Genet, 35:190-194, Sep. 21, 2003.
Phillips-Cremins et al., "Architectural protein subclasses shape 3D organization of genomes during lineage commitment," Cell, 153(6):1281-1295, Jun. 6, 2013.
Pinter et al., "Spreading of X chromosome inactivation via a hierarchy of defined Polycomb stations," Genome Res, 22:1864-1876, Sep. 4, 2012.
Plenge et al., "Skewed X-Chromosome Inactivation Is a Common Feature of X-Linked Mental Retardation Disorders," Am. J. Hum. Genet, 71(1):168-173, Jul. 2002.
Sado et al., "Regulation of imprinted X-chromosome inactivation in mice by Tsix," Development, 128:1275-1286, Apr. 15, 2001.
Saldana-Meyer et al., "CTCF regulates the human p53 gene through direct interaction with its natural antisense transcript, Wrap53," Genes Dev, 28:723-734, 2014.
Sanyal et al., "The long-range interaction landscape of gene promoters," Nature, 489:109-113, Dec. 6, 2012.
Sarma et al., "Locked nucleic acids (LNAs) reveal sequence requirements and kinetics of Xist RNA localization to the X chromosome," Proc Natl Acad Sci USA, 107(51):22196-22201, Dec. 21, 2010.
Shen et al., "A map of the cis-regulatory sequences in the mouse genome," Nature, 488:116-120, Aug. 2, 2012.
Spencer et al., "A boundary element between Tsix and Xist binds the chromatin insulator Ctcf and contributes to initiation of X-chromosome inactivation," Genetics, 189(2):441-454, Aug. 11, 2011.
Splinter et al., "CTCF mediates long-range chromatin looping and local histone modification in the β-globin locus," Genes Dev, 20:2349-2354, Sep. 2006.
Starmer and Magnuson, "A new model for random X chromosome inactivation," Development, 136:1-10, Jan. 1, 2009.
Stavropoulos et al., "Identification of developmentally specific enhancers for Tsix in the regulation of X chromosome inactivation," Mol Cell Biol, 25(7):2757-2769, Apr. 2005.
Sun, et al., "Jpx RNA activates Xist by evicting CTCF," Cell, 153(7):1537-1551, Jun. 20, 2013.
Takahashi et al., "Application of the chromatin immunoprecipitation method to identify in vivo protein-DNA associations in fission yeast," Sci STKE, 2000(56):11, Oct. 31, 2000.
Tsai et al., "Higher order chromatin structure at the X-inactivation center via looping DNA," Dev Biol, 319(2):416-425, Jul. 15, 2008.
Van den Veyver, "Skewed X inactivation in X-linked disorders," Semin Reprod Med, 19(2):183-91, 2001.
Wahlestedt, "Targeting Long Non-Coding RNA to Therapeutically Upregulate Gene Expression," Nature Reviews, Jun. 2013, 12:433-446.
Wan and Bartolomei, "Regulation of imprinting in clusters: Noncoding RNAs versus insulators," Adv Genet, 61:207-223, 2008.
Wutz, "Gene silencing in X-chromosome inactivation: advances in understanding facultative heterochromatin formation," Nat Rev Genet 12:542-553, Aug. 2011.
Xi et al., "Identification and characterization of cell type-specific and ubiquitous chromatin regulatory structures in the human genome," PLoS Genetics, 3(8):e136, Aug. 17, 2007.
Xu et al., "Evidence that homologous X-chromosome pairing requires transcription and Ctcf protein," Nat Genet, 39:1390-1396, Oct. 2007.
Xu et al., "Transient homologous chromosome pairing marks the onset of X inactivation," Science, 311(5764):1149-1152, Jan. 19, 2006.

(56) References Cited

OTHER PUBLICATIONS

Yang et al., "Global survey of escape from X inactivation by RNA-sequencing in mouse," Genome Res, 20:614-622, Apr. 2010.

Yao et al., "Mediation of CTCF transcriptional insulation by Dead-box RNA-binding protein p68 and steroid receptor RNA activator SRA," Genes Dev, 24:2543-2555, Oct. 2010.

Zhang et al., "Interruption of intrachromosomal looping by CCCTC binding factor decoy proteins abrogates genomic imprinting of human insulin-like growth factor II," J Cell Biol, 193(3):475-487, May 2, 2011.

Zhao et al., "Genome-wide identification of polycomb-associated RNAs by RIP-seq," Mol Cell, 40(6):939-953, Dec. 22, 2010.

Zhao et al., "Polycomb proteins targeted by a short repeat RNA to the mouse X chromosome," Science, 322(5902):750-756, Oct. 31, 2008.

Obad et. al., "Silencing of microRNA families by seed-targeting tiny LNAs," Nat. Genet., Apr. 2011, 43(4):371-378.

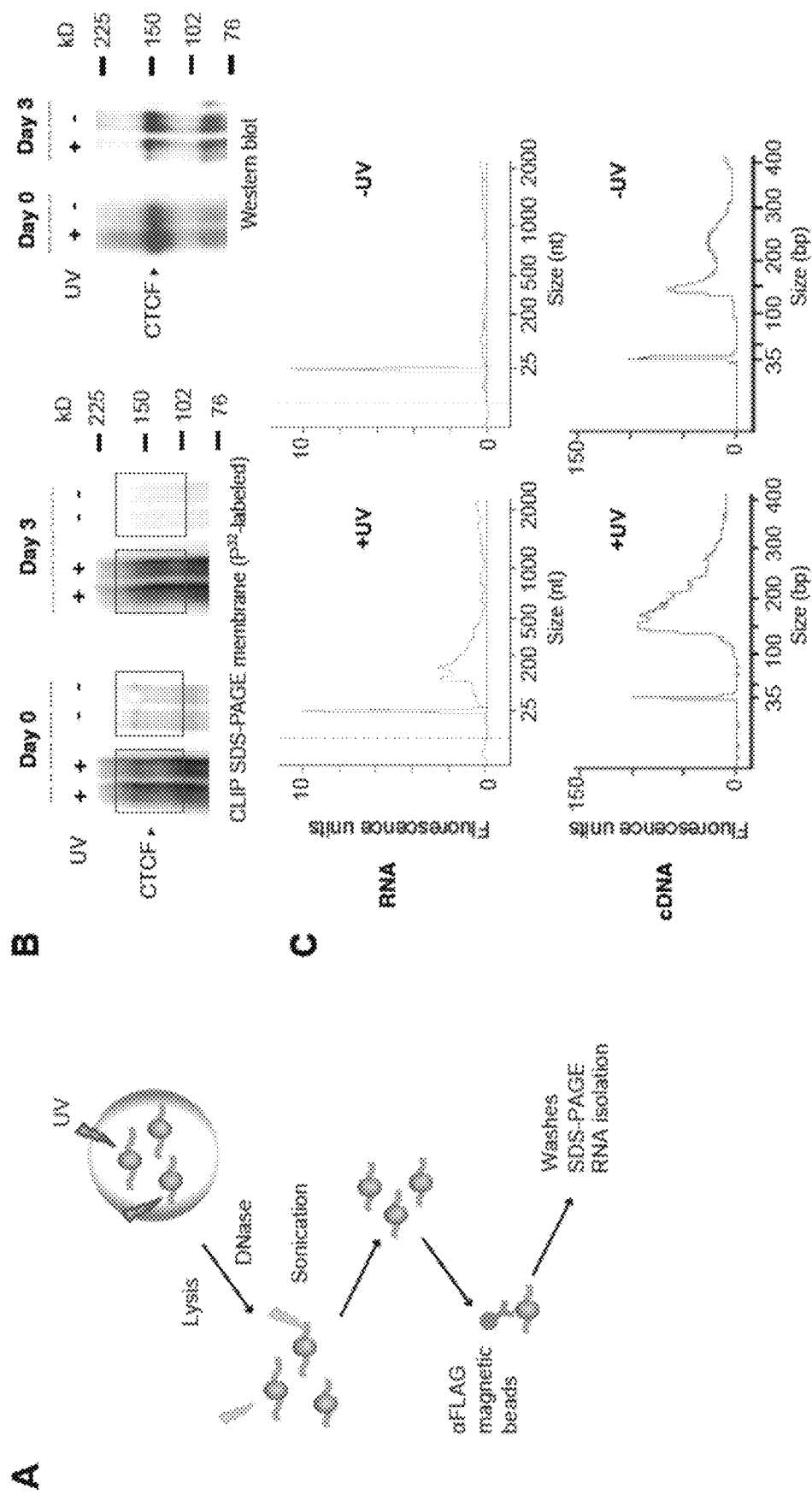
FIGs. 1A-C

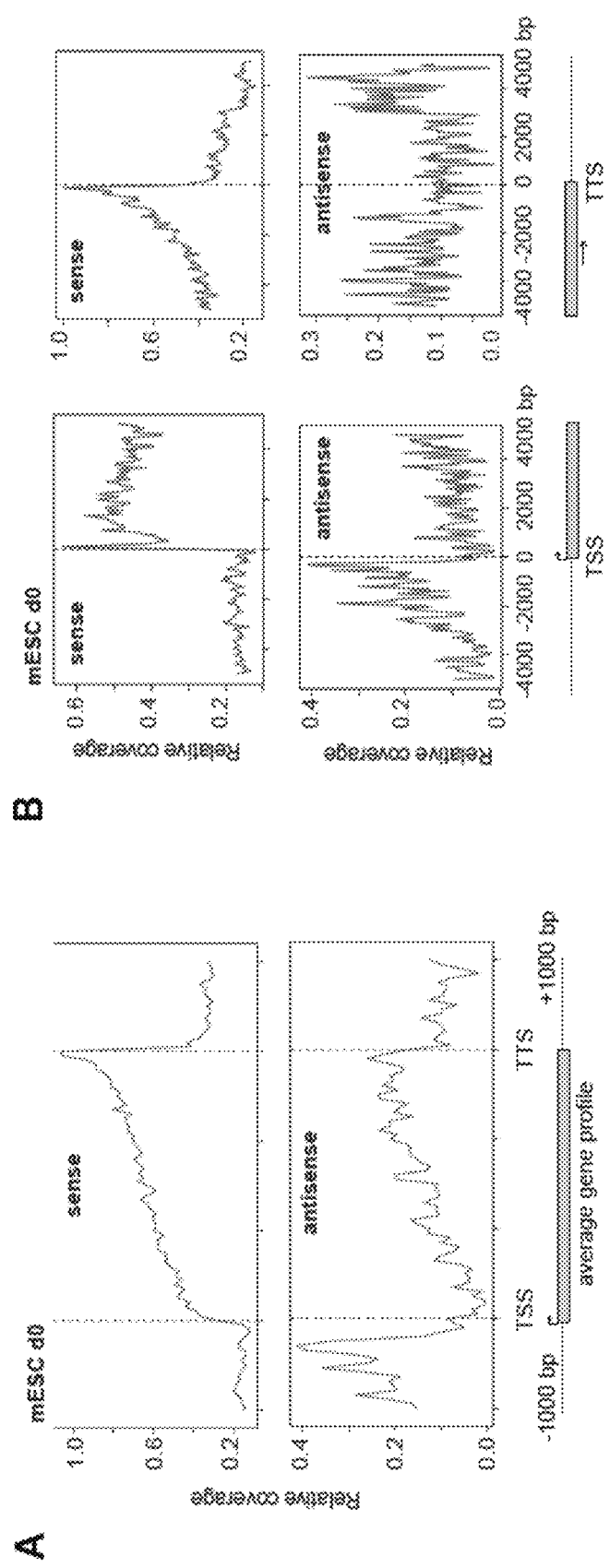
FIGs. 2A-B

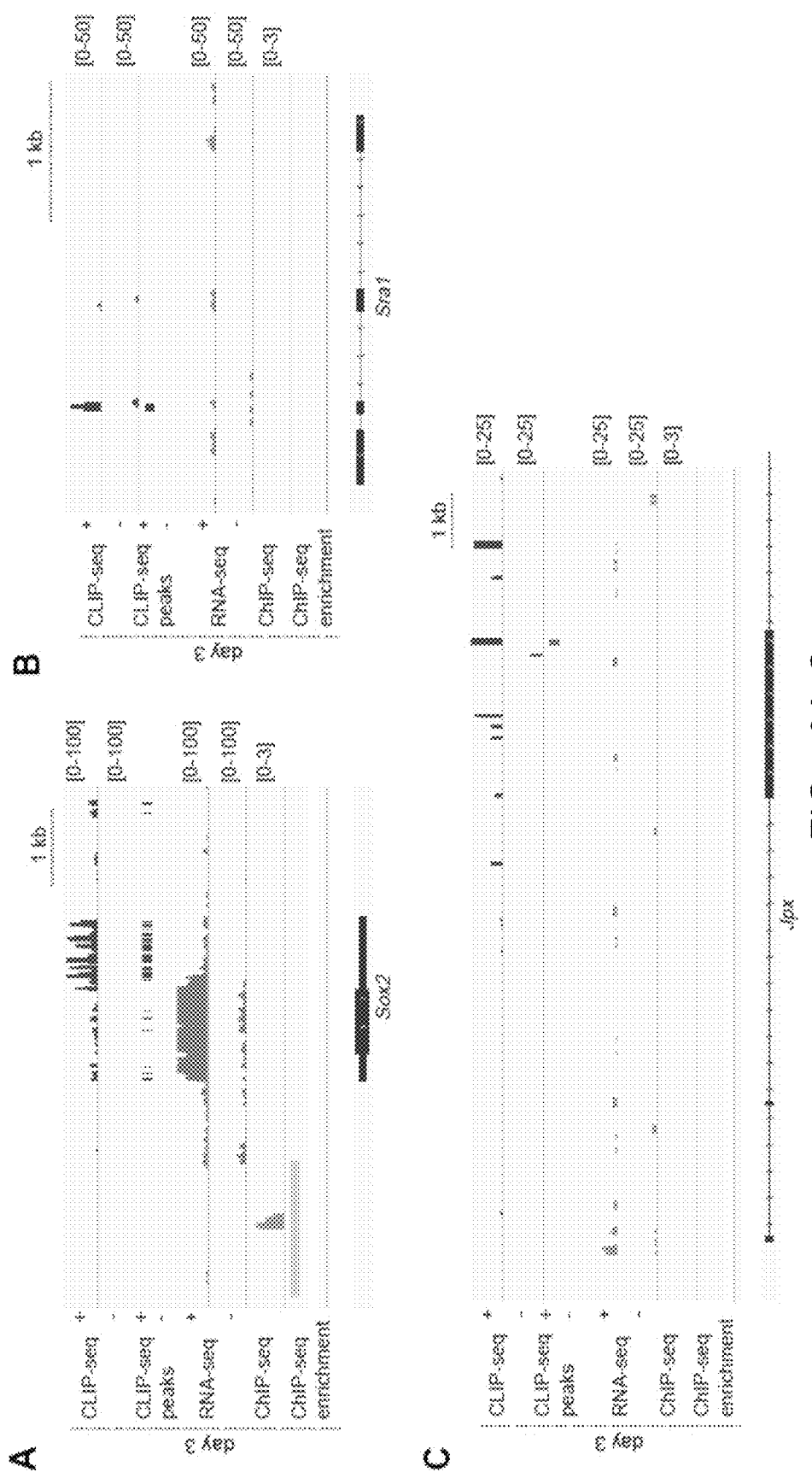
FIGs. 3A-C

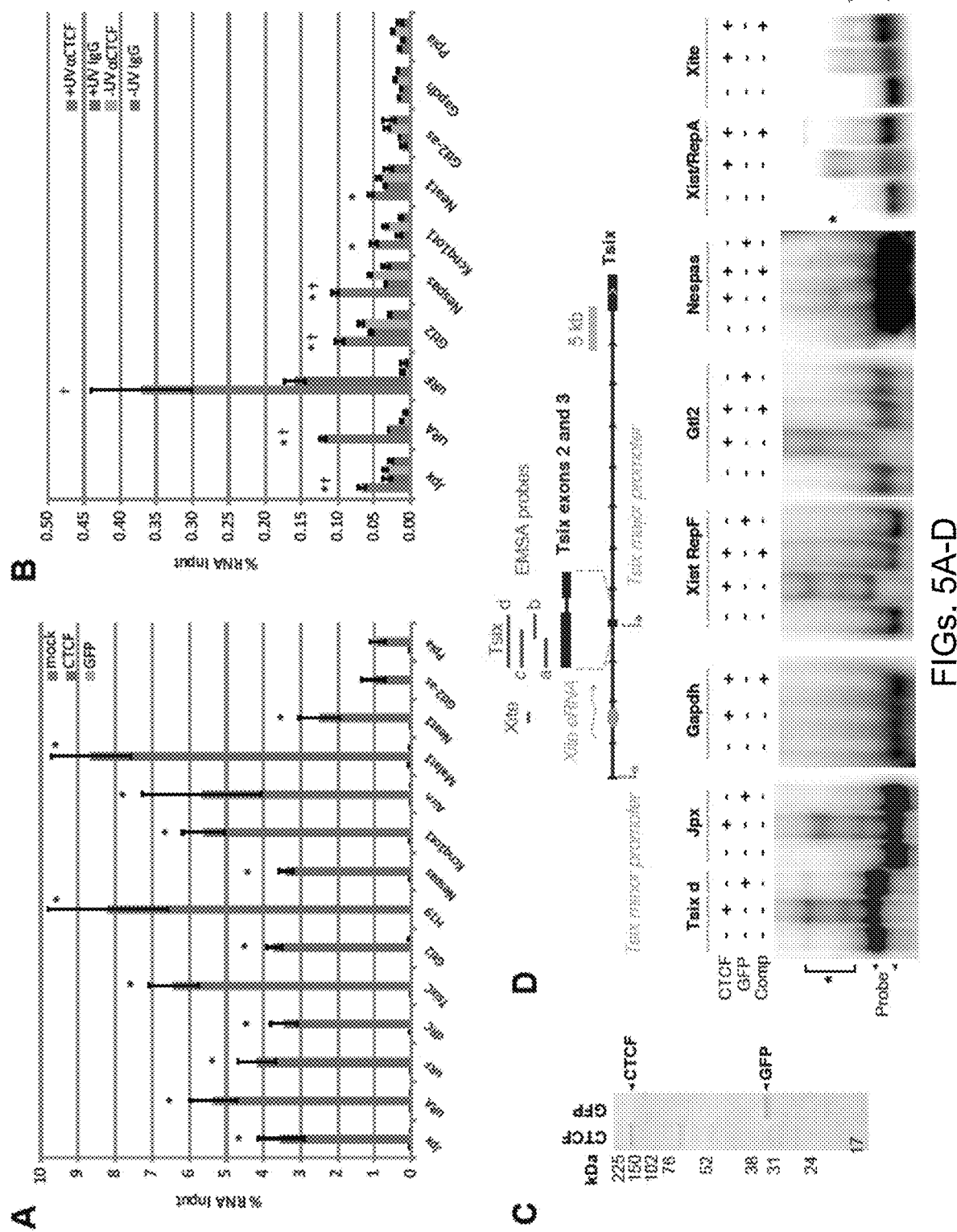
FIGs. 5A-D

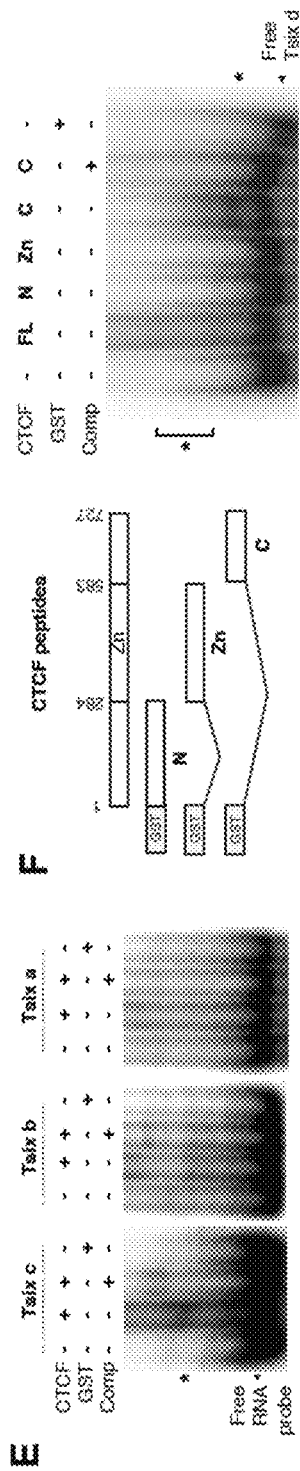
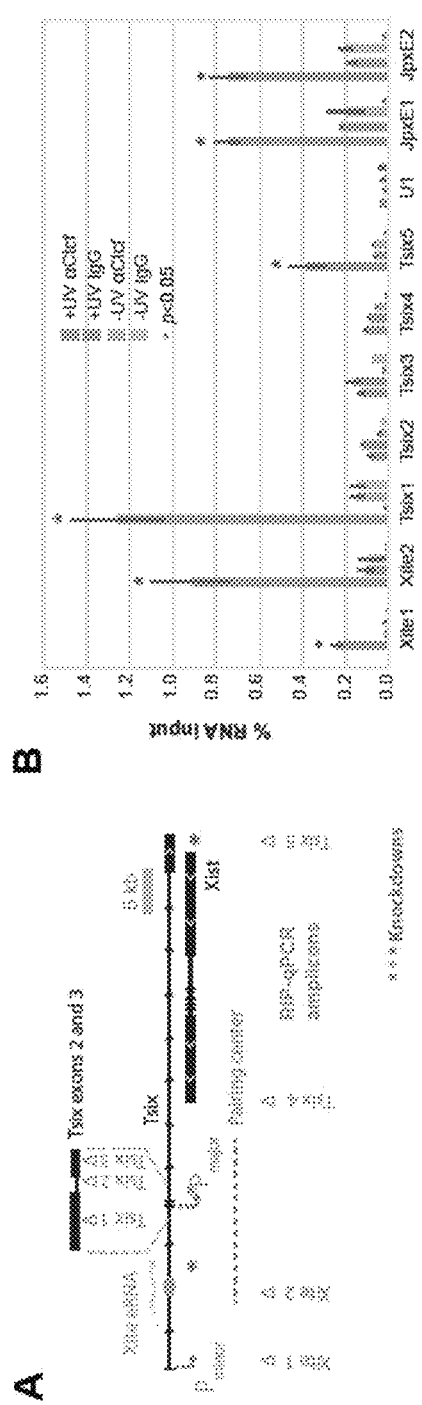
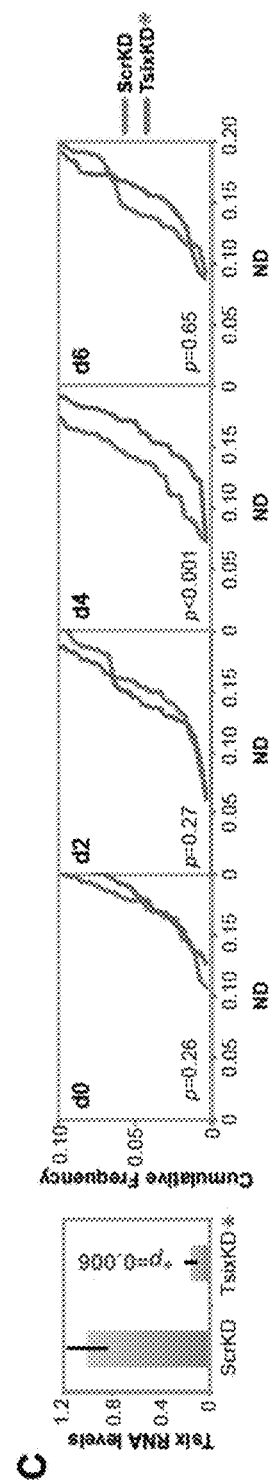
FIGs. 5E-F
FIGs. 6A-C

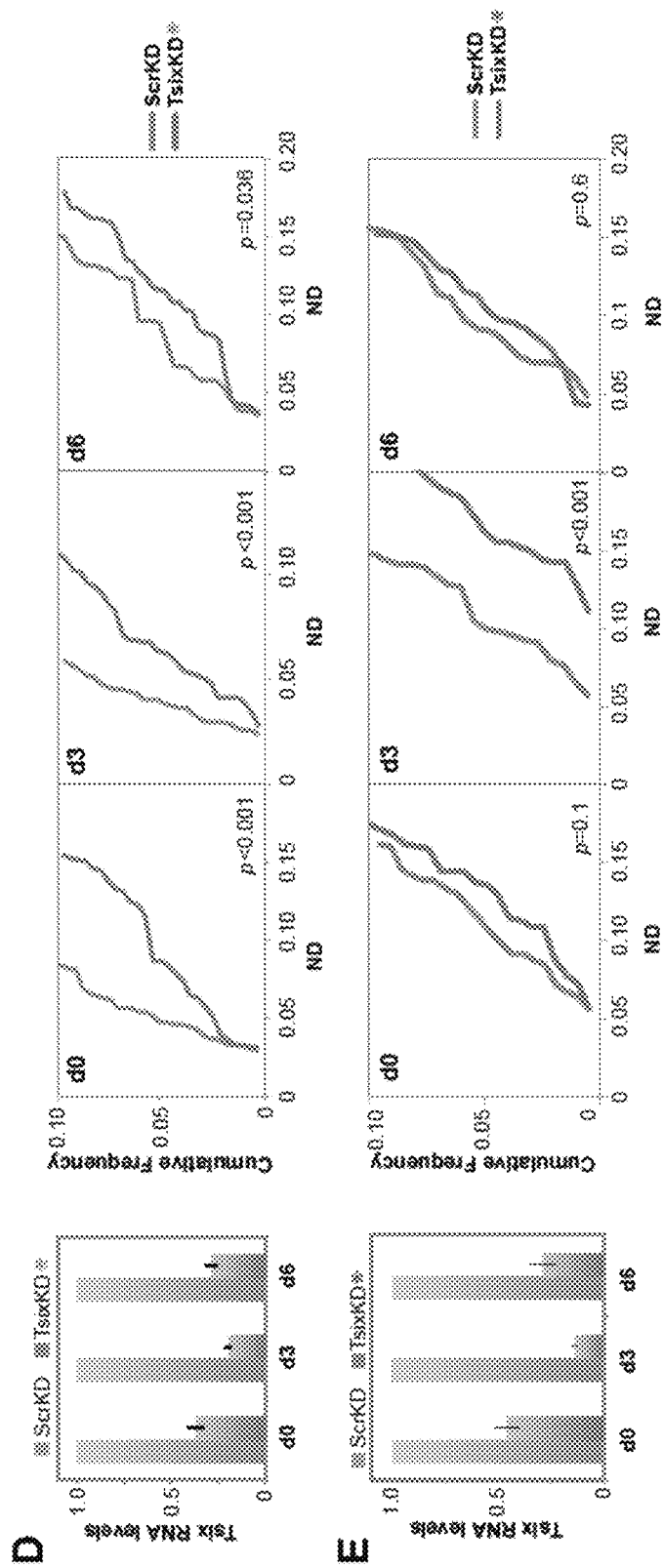
FIGs. 6D-E

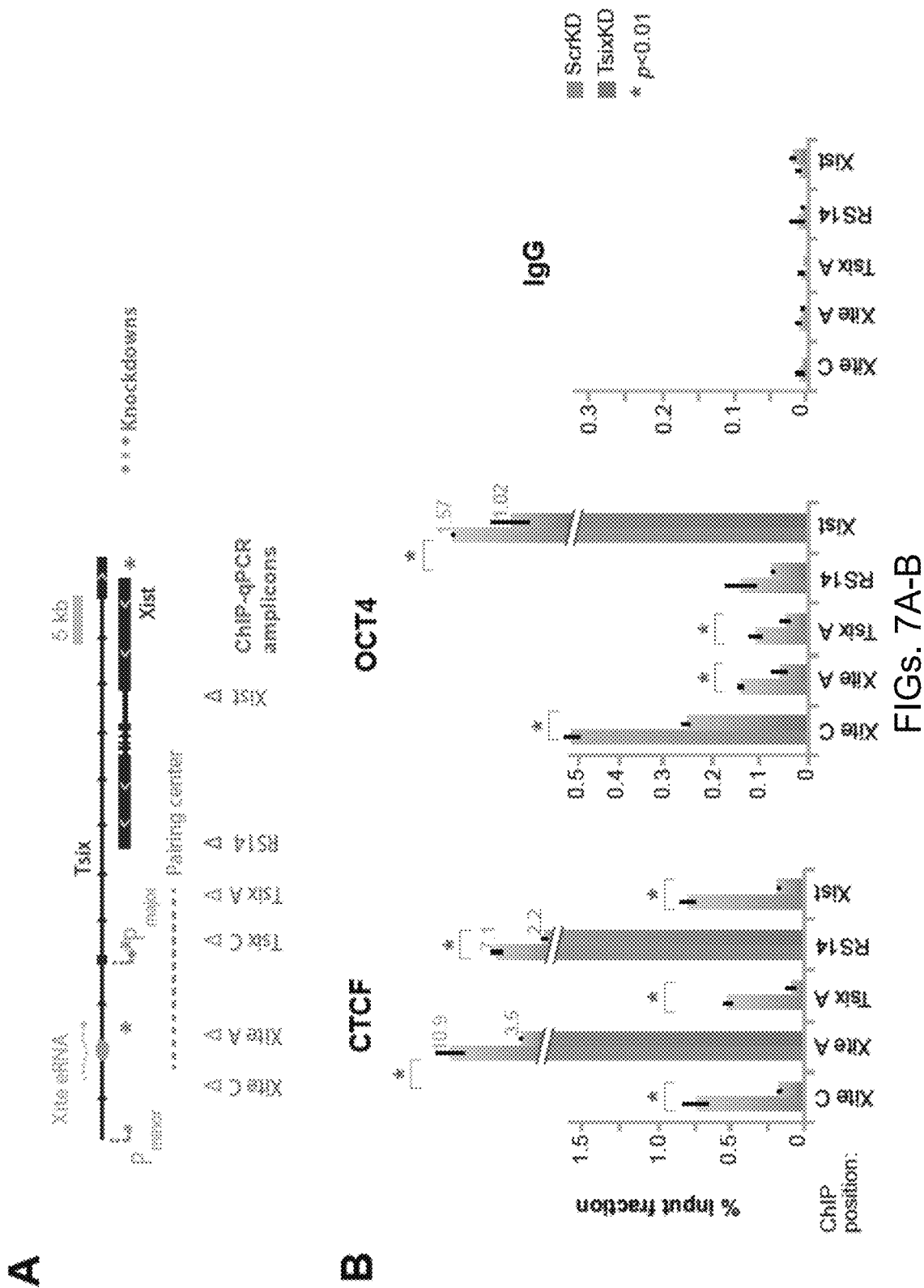
FIGs. 7A-B

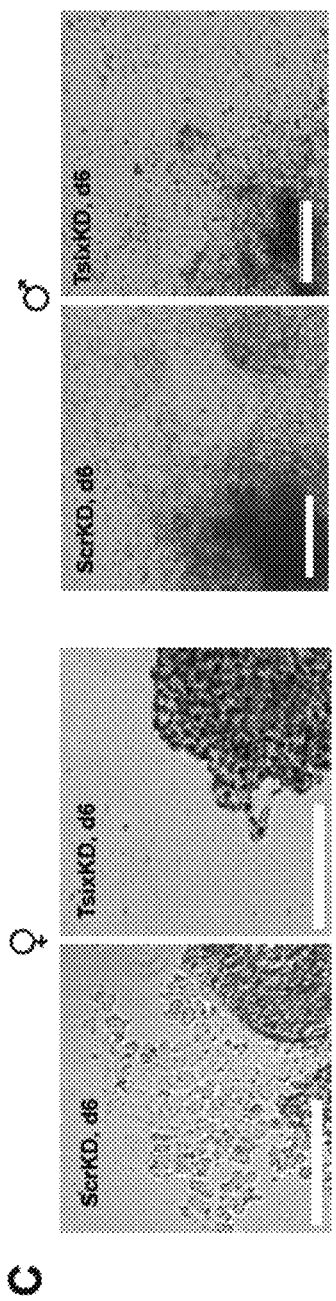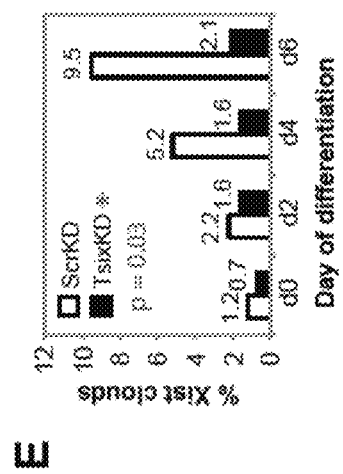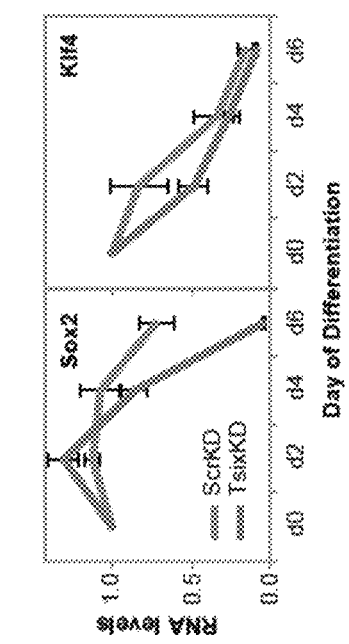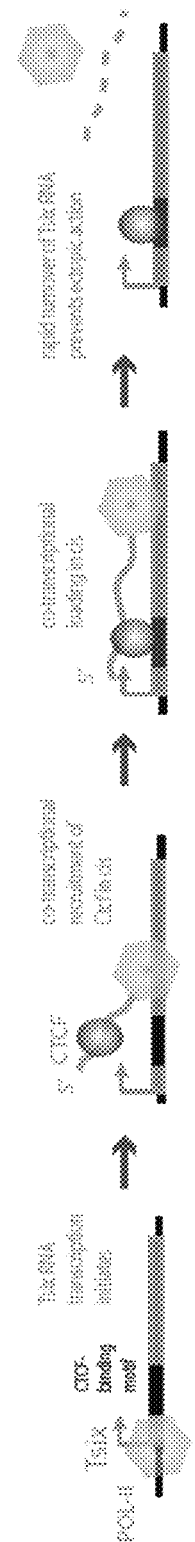
FIGs. 7C-F

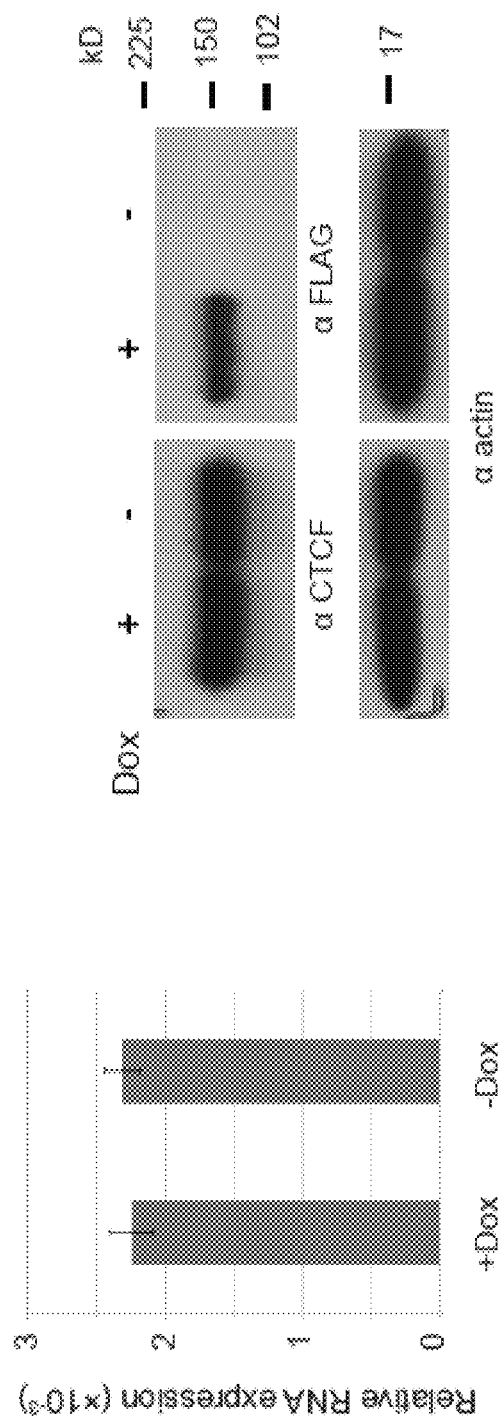

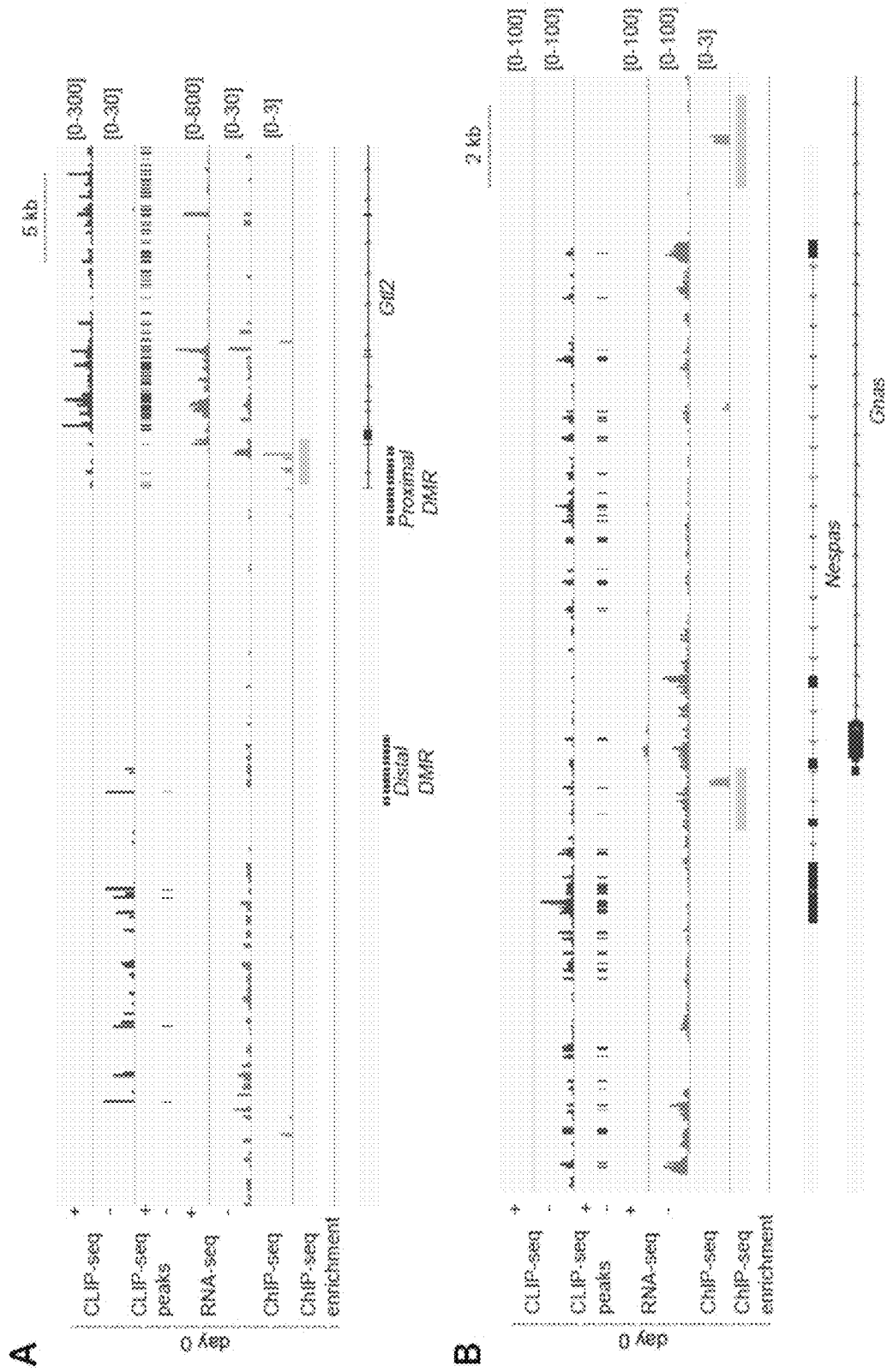
FIGs. 10A-B

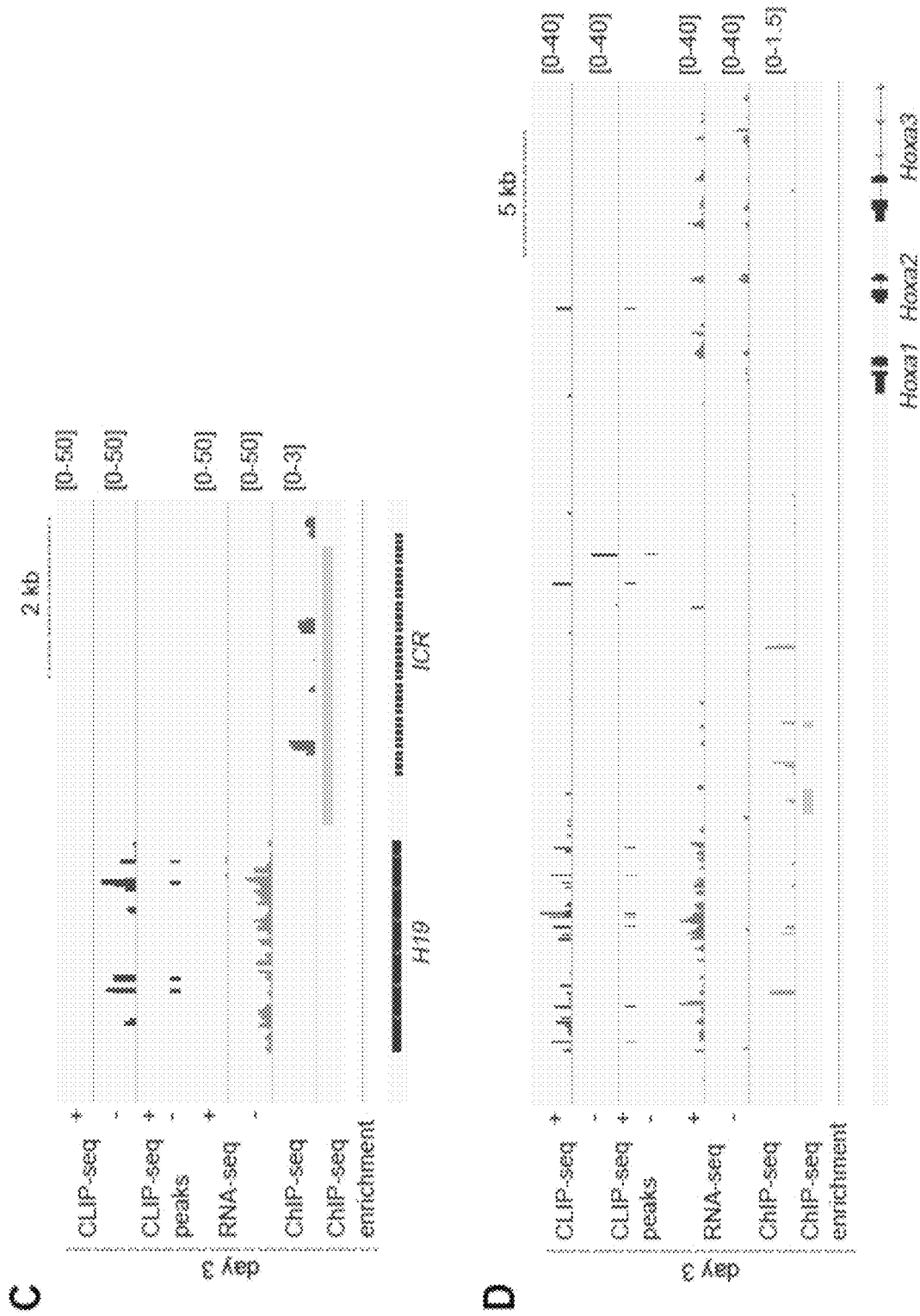
FIGs. 10C-D

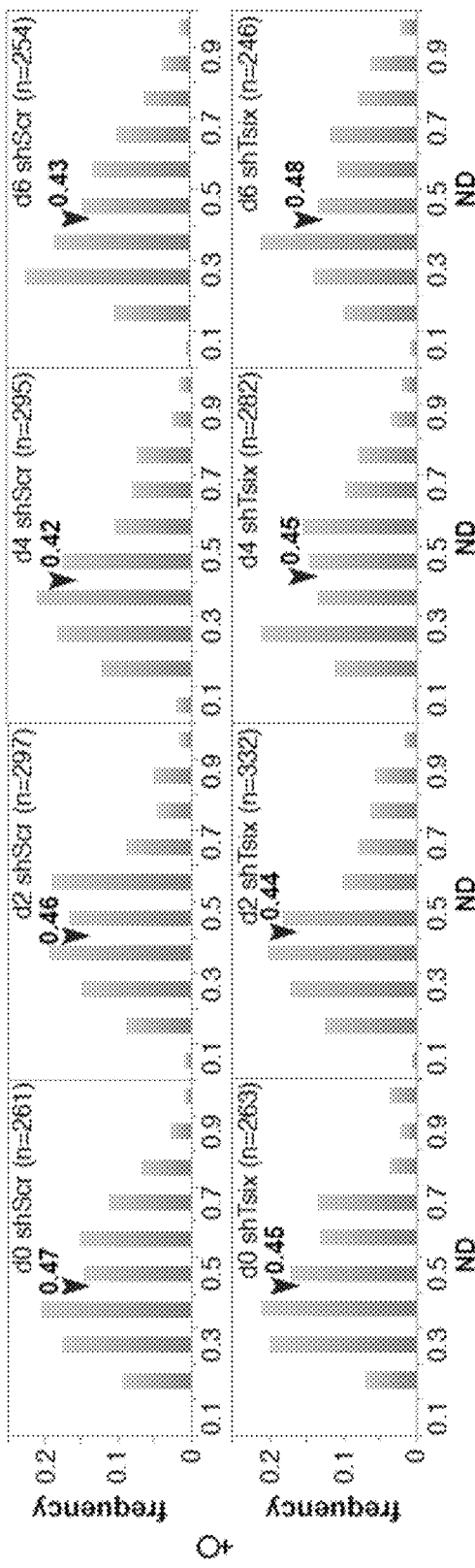
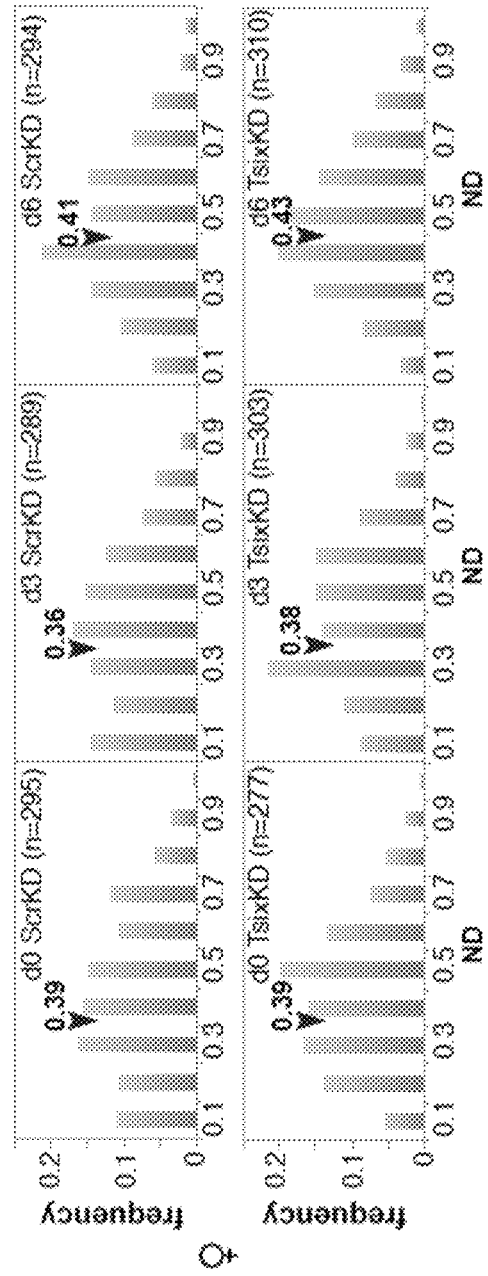
FIG. 11A
FIG. 11B

CCCTC-BINDING FACTOR (CTCF) RNA INTERACTOME

CLAIM OF PRIORITY

This application is a continuation of U.S. patent application Ser. No. 14/735,930, filed Jun. 10, 2015, which claims the benefit of U.S. Provisional Patent Application Ser. No. 62/010,342, filed on Jun. 10, 2014. The entire contents of the foregoing are hereby incorporated by reference.

FEDERALLY SPONSORED RESEARCH OR DEVELOPMENT

This invention was made with Government support under Grant No. GM58839 awarded by the National Institutes of Health. The Government has certain rights in the invention.

TECHNICAL FIELD

This invention relates to methods and compositions for selectively reactivating or repressing certain genes, e.g., genes regulated by zinc-finger protein CCCTC-binding factor (CTCF). On the inactive X chromosome (Xi), e.g., genes associated with X-linked diseases, e.g., Rett Syndrome, Factor VIII or IX deficiency, Fragile X Syndrome, Duchenne muscular dystrophy, and PNH, in heterozygous females carrying a mutated allele, in addition to a functional wildtype or hypomorphic allele.

BACKGROUND

The zinc-finger protein CCCTC-binding factor, CTCF, is a ubiquitous gene regulator that is frequently mutated or aberrantly expressed in cancer and other human diseases (Lobanenkov et al., 1990; Ohlsson et al., 2001; Kim et al., 2007; Ohlsson et al., 2010; Chen et al., 2012; Nakahashi et al., 2013). CTCF binds throughout the genome via combinatorial subsets of its 11 zinc fingers, serving as chromatin insulator, activator, or repressor depending on the epigenetic context (Filippova, 2008; Ong and Corces, 2014). One mechanism by which CTCF exercises its gene regulatory function occurs through mediation of long-range intra- and inter-chromosomal interactions that bring distant genetic elements into close proximity. In the case of intra-chromosome interactions, formation of "active chromatin hubs" (ACH)(Palstra et al., 2003; Splinter et al., 2006) results in "loop-outs" of regions that are excluded from expression.

Some of the best-studied cases of intra-chromosomal regulation by CTCF can be found in the imprinted gene cluster, H19-Igf2, where CTCF binds to an imprint control region (ICR) on the maternal allele to block the enhancer from engaging the Igf2 allele in cis, involving the formation of intrachromosomal loops between the ICR and Igf2 promoter (Bell and Felsenfeld, 2000; Hark et al., 2000; Kanduri et al., 2002; Li et al., 2008; Wan and Bartolomei, 2008; Zhang et al., 2011). Genome-wide chromosome interaction studies indicate that CTCF is often enriched at interaction boundaries at sites between genes and their distal regulatory elements (Handoko et al., 2011; Dixon et al., 2012; Sanyal et al., 2012; Shen et al., 2012; DeMare et al., 2013; Phillips-Cremins et al., 2013). CTCF may also aid inter-chromosomal associations between maternal H19-Igf2 ICR (Chr. 7) and paternal Wsb1-Nf1 (Chr. 11)(Ling et al., 2006), though the function of this interaction is unclear.

CTCF's role in epigenetic regulation has also been studied intensively for X-chromosome inactivation (XCI), the dosage compensation mechanism in mammals in which one of the two Xs in females is heterochromatinized and silenced early in development by the long noncoding Xist RNA (Heard and Disteche, 2006; Starmer and Magnuson, 2009; Wutz, 2011; Disteche, 2012; Lee and Bartolomei, 2013). During XCI, CTCF plays a number of different roles and binds a large number of sites within concentrated regions of the X-inactivation center. Here CTCF acts both in cis and in trans. In trans, CTCF-mediated inter-chromosomal interactions play a role in X-chromosome pairing, a process that has been proposed to ensure mutually exclusive choice of active versus inactive X chromosomes (Bacher et al., 2006; Xu et al., 2006; Xu et al., 2007; Donohoe et al., 2009; Masui et al., 2011). In cis, CTCF-binding sites have been correlated with intra-chromosomal interactions (Tsai et al., 2008; Spencer et al., 2011) and topologically associated domains (Nora et al., 2012) around the X-inactivation center. For example, CTCF binds the RS14 element between Xist and its antisense repressor, Tsix, to form a presumptive border between two ACH's, with one ACH involving physical interactions between promoter regions of Xist and its activator, Jpx, for the inactive X, and the other ACH centering on interactions between Tsix and its enhancer, Xite, for the active X.

SUMMARY

As described herein, crosslinking immunoprecipitation (CLIP) coupled with high-throughput sequencing (CLIP-seq) analysis was used to define an RNA interactome for CTCF in mouse embryonic stem cells (mESC) and human HEK293 kidney cells; in parallel, chromatin immunoprecipitation (ChIP) followed by high-throughput DNA sequencing (ChIP-seq) was performed to investigate the epigenomic landscape relative to interacting transcripts in the mESC. The genome-wide datasets reported here provide a useful resource for modulating CTCF's role in epigenomic regulation.

Thus, in a first aspect, the invention provides methods for activating an inactive X-linked allele in a cell, preferably a cell of a female heterozygous subject. The methods include administering to the cell an inhibitory oligonucleotide targeting a sequence within 500 nucleotides of a CTCF binding site on a CTCF-interacting RNA, i.e., complementary or identical to a region within 500 nts of a CTCF binding site, i.e., within a sequence as listed in Tables 1-2 (each of which shows a binding site sequence +500 flanking nucleotides on both sides). In some embodiments, the inactive X-linked allele is associated with an X-linked disorder, and the oligonucleotide is administered in a therapeutically effective amount.

In another aspect, the invention provides methods for activating a repressed autosomal gene in a cell. The methods include administering to the cell an inhibitory oligonucleotide targeting a sequence within 500 nucleotides of a CTCF binding site on a CTCF-interacting RNA that represses the autosome or the autosomal gene, i.e., complementary or identical to a region within 500 nts of a CTCF binding site on the RNA, i.e., within a sequence as listed in Tables 1-2 (each of which shows a binding site sequence +500 flanking nucleotides on both sides). In some embodiments, the repressed gene is associated with a disorder, and the oligonucleotide is administered in a therapeutically effective amount.

In another aspect, the invention provides methods for downregulating an X-linked escapee gene in a cell. The methods include administering to the cell an inhibitory oligonucleotide targeting a sequence within 500 nucleotides of a CTCF binding site on a CTCF-interacting RNA that increases expression of the X-linked escapee gene, i.e., complementary or identical to a region within 500 nts of a CTCF binding site on the RNA, i.e., within a sequence as listed in Tables 1-2 (each of which shows a binding site sequence +500 flanking nucleotides on both sides). In some embodiments, the X-linked escapee gene is associated with a disorder, and the oligonucleotide is administered in a therapeutically effective amount.

In another aspect, the invention provides methods for repressing an autosomal gene in a cell. The methods include administering to the cell an inhibitory oligonucleotide targeting a sequence within 500 nucleotides of a CTCF binding site on a CTCF-interacting RNA that increases expression of the autosomal gene, i.e., complementary or identical to a region within 500 nts of a CTCF binding site on the RNA, i.e., within a sequence as listed in Tables 1-2 (each of which shows a binding site sequence +500 flanking nucleotides on both sides). In some embodiments, the autosomal gene is associated with a disorder, and the oligonucleotide is administered in a therapeutically effective amount.

In a further aspect, the invention provides methods for increasing expression of a selected gene listed in Tables 1 or 2 in a cell; the methods include contacting the cell with a nucleic acid triplex-forming oligonucleotide (TFO) that binds specifically to a CTCF localization sequence or binding site associated with the selected gene.

In some embodiments, the cell is in a living subject, e.g., a human, and the oligonucleotide is optionally administered in a therapeutically effective amount.

In some embodiments, the inhibitory oligonucleotide is identical or complementary to at least 8 consecutive nucleotides of a strong or moderate binding site nucleotide sequence as set forth in Tables 1-2, or complementary to at least 8 consecutive nucleotides of a caRNA as set forth in Tables 1-2.

In another aspect, the invention provides inhibitory oligonucleotides that are complementary or identical to at least 8 consecutive nucleotides of a CTCF binding site nucleotide sequence as set forth in Tables 1-2.

In some embodiments, the oligonucleotide does not comprise three or more consecutive guanosine nucleotides.

In some embodiments, the oligonucleotide does not comprise four or more consecutive guanosine nucleotides.

In some embodiments, the oligonucleotide is 8 to 30 nucleotides in length.

In some embodiments, at least one nucleotide of the oligonucleotide is a nucleotide analogue.

In some embodiments, at least one nucleotide of the oligonucleotide comprises a 2' O-methyl. In some embodiments, each nucleotide of the oligonucleotide comprises a 2' O-methyl.

In some embodiments, the oligonucleotide comprises at least one ribonucleotide, at least one deoxyribonucleotide, or at least one bridged nucleotide.

In some embodiments, the bridged nucleotide is a LNA nucleotide, a cEt nucleotide or a ENA modified nucleotide.

In some embodiments, each nucleotide of the oligonucleotide is a LNA nucleotide.

In some embodiments, one or more of the nucleotides of the oligonucleotide comprise 2'-fluoro-deoxyribonucleotides.

In some embodiments, one or more of the nucleotides of the oligonucleotide comprise 2'-O-methyl nucleotides.

In some embodiments, one or more of the nucleotides of the oligonucleotide comprise ENA nucleotide analogues.

In some embodiments, one or more of the nucleotides of the oligonucleotide comprise LNA nucleotides.

In some embodiments, the nucleotides of the oligonucleotide comprise comprising phosphorothioate internucleotide linkages between at least two nucleotides.

In some embodiments, the nucleotides of the oligonucleotide comprise phosphorothioate internucleotide linkages between all nucleotides.

In some embodiments, the oligonucleotide is a gapmer or a mixmer.

In some embodiments of the methods described herein, the TFO comprises one or more of DNA, RNA, PNA, HNA, MNA, ANA, LNA, CAN, INA, CeNA, TNA, (2'-NH)-TNA, (3'-NH)-TNA, alpha-L-Ribo-LNA, alpha-L-Xylo-LNA, beta-D-Ribo-LNA, beta-D-Xylo-LNA, [3.2.1]-LNA, Bicyclo-DNA, 6-Amino-Bicyclo-DNA, 5-epi-Bicyclo-DNA, alpha-Bicyclo-DNA, Tricyclo-DNA, Bicyclo[4.3.0]-DNA, Bicyclo[3.2.1]-DNA, Bicyclo[4.3.0]amide-DNA, beta-D-Ribopyranosyl-NA, alpha-L-Lyxopyranosyl-NA, 2'-R-RNA, 2'-OR-RNA, 2'-AE-RNA, alpha-L-RNA, and beta-D-RNA.

In some embodiments of the methods described herein, the TFO includes one or more modifications described herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

REFERENCE TO SEQUENCE LISTING SUBMITTED ON A COMPACT DISC

This application includes a sequence listing submitted on compact disc. The sequence listing is identified on the compact disc as follows.

| File Name | Date of Creation | Size |
| --- | --- | --- |
| 29539-0115002 SEQ LIST.txt | Apr. 13, 2018 | 238,862 KB |

The entire content of this file is hereby incorporated by reference.

DESCRIPTION OF DRAWINGS

The patent or application file contains at least one drawing executed in color. Copies of this patent or patent application publication with color drawing(s) will be provided by the Office upon request and payment of the necessary fee.

FIGS. 1A-E. CLIP-seq identifies a large CTCF-RNA interactome.

(A) Schematic for modified CLIP-seq protocol.

(B) Autoradiographs ($^{32}$P, top) and α-FLAG Western blots (bottom) for CLIP, performed in CTCF-3xFLAG expressing d0 and d3 mESC with or without UV (256 nm)

irradiation. Location of FLAG-CTCF-bound RNA indicated with bracket on autoradiograph. Red boxes indicate regions of membrane excised for RNA isolation and library synthesis.

(C) Agilent Bioanalyzer profiles of membrane-isolated RNA (top) and corresponding CLIP-seq library (bottom) from d0 experiments. ±UV, with or without UV irradiation. Spike at 25 nt (for RNA) or 35 bp (for DNA) are the lower markers for Bioanalyzer runs.

(D) Scatterplot comparing +UV and −UV library reads. Fragments per kilobase per million reads (FPKM) were calculated from both libraries over transcripts that were assembled from RNA-seq data. Loge values of FPKM were plotted; d0 data shown. Red line is x=y diagonal. Pearson's correlation (R)=0.773, p<<0.0001.

(E) Enrichment of total, sense and antisense CTCF CLIP peaks, from day 0 mESC, in various genomic regions as compared to reference mouse genome.

FIGS. 2A-E. Characterization of the CTCF RNA interactome.

(A) Average CLIP peaks profile over a 3-kb metagene, as well as 1 kb up- or down-stream, for d0 CLIP peaks that are sense or antisense to RefSeq annotated genes.

(B) Average profile of d0 CLIP peaks between 0-4 kb up- or downstream of transcription start site (TSS) or transcription termination site (TTS).

(C) Scatterplot comparing CLIP-seq and RNA-seq coverage. Fragments per kilobase per million reads (FPKM) were calculated for both libraries, and their loge values were plotted against each other; d3 data shown. Transcripts were assembled from RNA-seq data. For CLIP-seq, coverage under all peaks within each transcript was summed for division over the transcript length. Red line is x=y diagonal. Position of various RNAs of interest indicated. Pearson's correlation (R)=0.287, p=2.94×10$^{-178}$.

(D) Metagene profiles comparing d3 CTCF CLIP (red) and ChIP (blue) peaks.

(E) Average profile of d3 ChIP peaks relative to CLIP peaks. CLIP-seq peak is centered at bp 0 on the x-axis.

FIGS. 3A-E. The RNA interactome and epigenomic landscape of CTCF.

Normalized CTCF CLIP-seq, ChIP-seq and RNA-seq signals for (A) Sox2, (B) Sra1, (C) Jpx, (D) 5' end of Xist, and (E) Xite and 5' end of Tsix. Below each CLIP and ChIP tracks are corresponding "peaks", defined as statistically significant CLIP and ChIP enriched segments. Regions of interest within Xist and Tsix indicated by red dashed bar. RNA data are divided into strand-specific tracks, with + strand being the Watson strand.

Figure 4A:
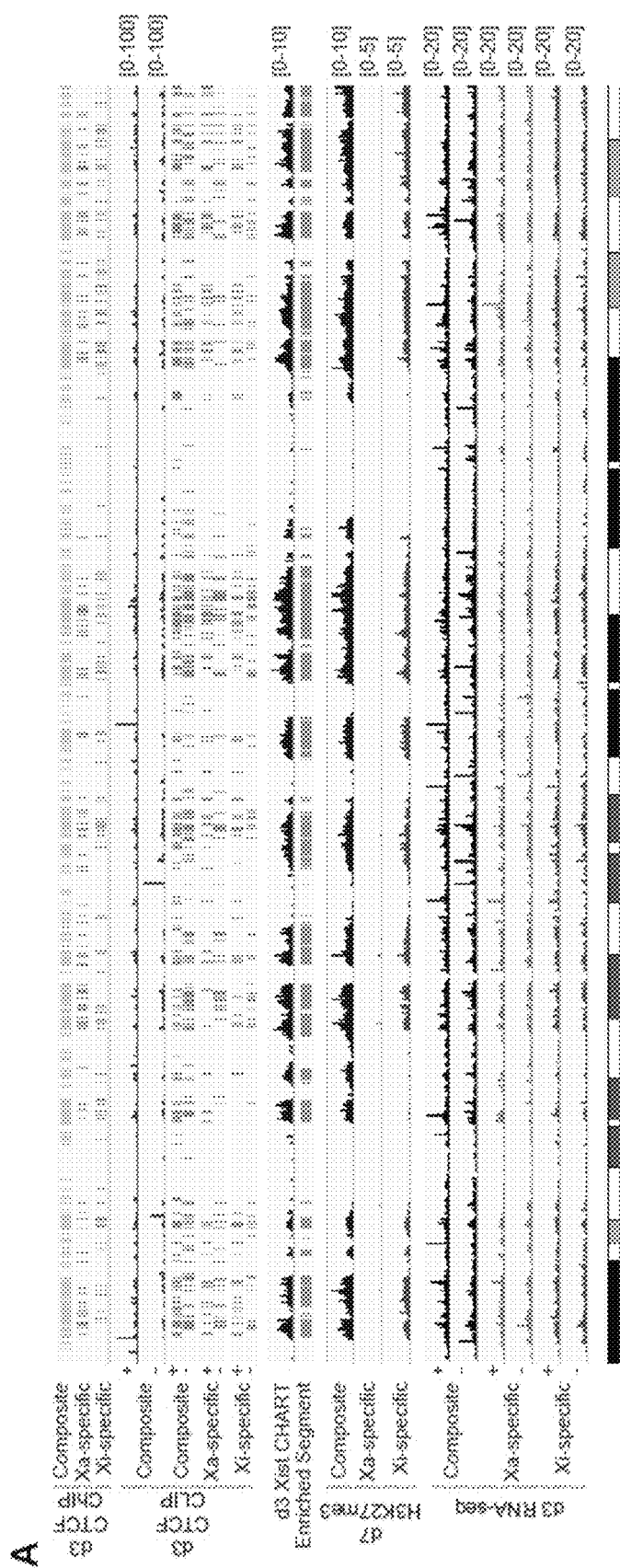
Figure 4B:
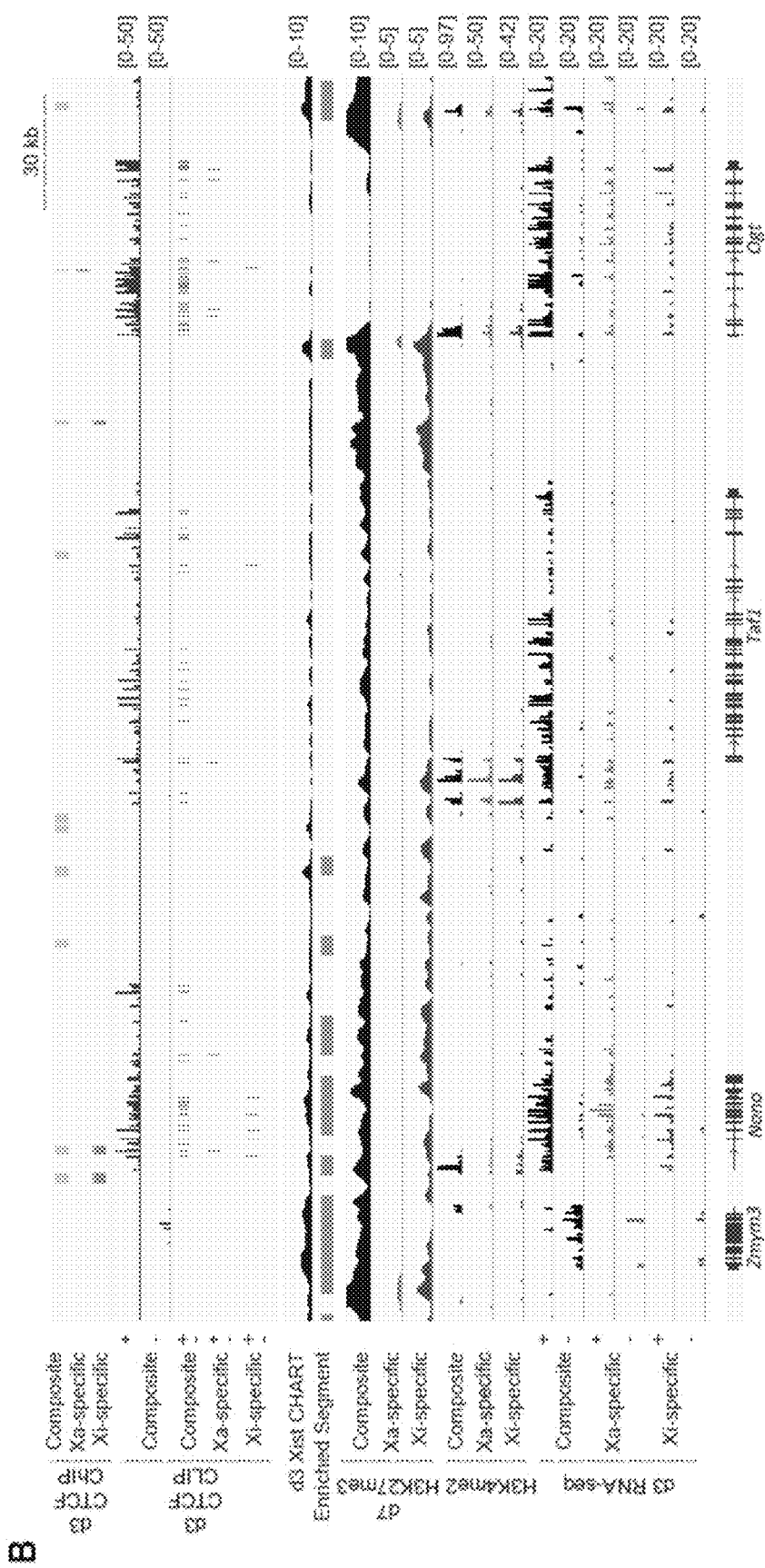
Figure 4C:
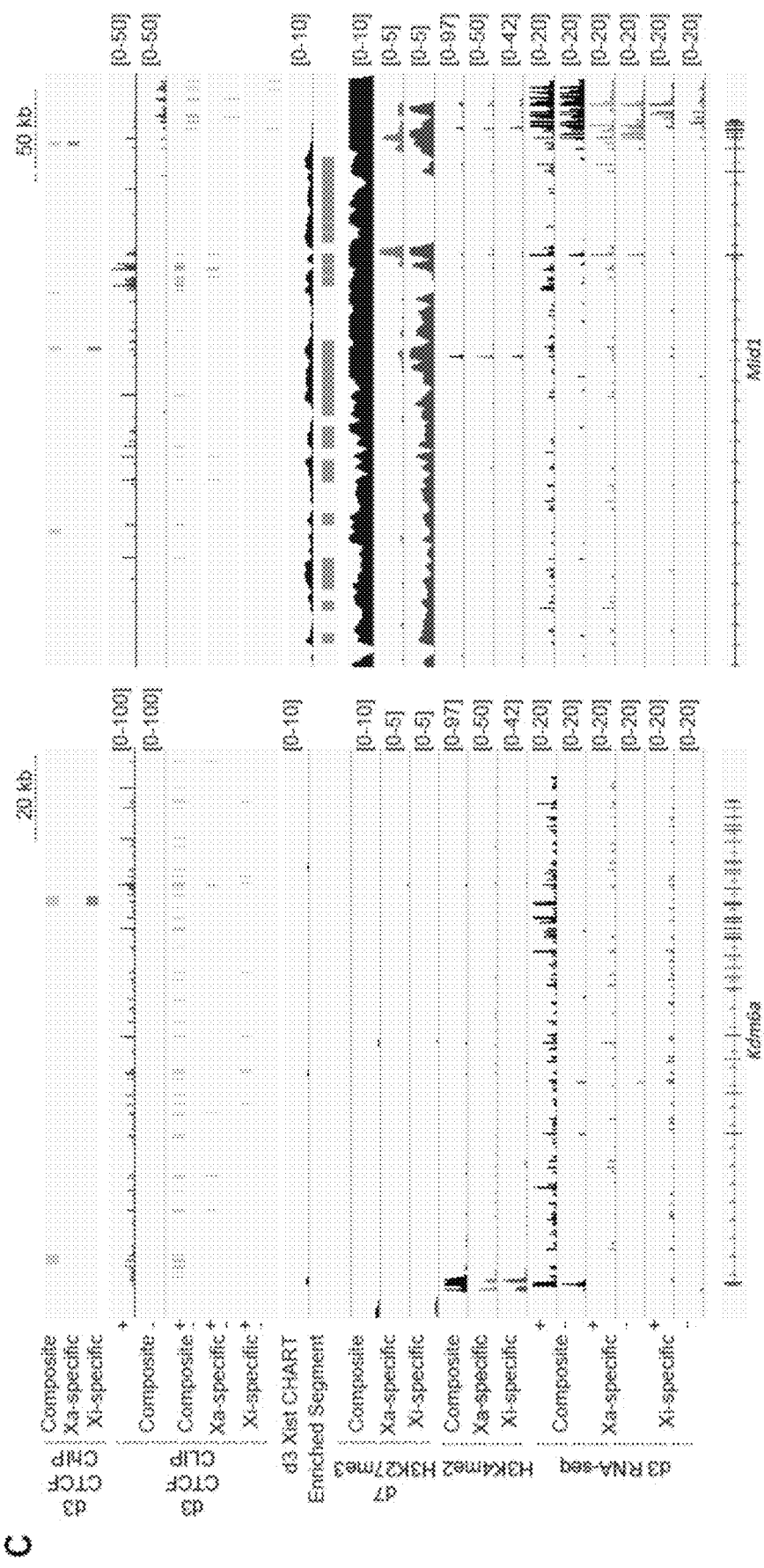

FIGS. 4A-C. Allele-specific binding of CTCF on the X-chromosome.

Day 3 CTCF ChIP peaks, CLIP peaks, and RNA-seq signal over (A) entire X chromosome, (B) Zmym-Nono-Taf1-Ogt region, (C) Kdm6a (left) and Mid1 (right). Only statistically significant ChIP and CLIP peaks are shown. Composite=sum of all peaks (cas, mus, and neutral). Xa-specific=enriched on cas chromosome. Xi-specific=enriched on mus chromosome. Day 3 ES composite Xist CHART, day 7 ES allelic H3K27me3 ChIP (Simon et al., 2013), and mouse embryonic fibroblast allelic H3K4me3 ChIP (Yildirim et al., 2012) data also included for comparison.

FIGS. 5A-F. CTCF binds RNA with high affinity and specificity.

(A) qRT-PCR for in vitro RNA pulldown with FLAG-CTCF, FLAG-GFP and mock pulldown. Results are expressed as percent of RNA in input sample. Representative results from four biological replicates shown. Means±1 SD shown. *, p<0.05, as determined by unpaired two-tailed Student's t-test comparing each amplicon to Ppia. RepA, RepF, RepC: Xist Repeats A, F and C. Ppia and Gtl2-as are negative controls.

(B) UV-RIP qRT-PCR, comparing αCTCF and IgG immunoprecipitation performed on UV-crosslinked or uncrosslinked day 3 ES cells. Results are expressed as percent of RNA in input sample. Representative results from three biological replicates shown. Means±1 SD shown. *, significant enrichment (p<0.05, determined by unpaired two-tailed Student's t-test) of +UV αCTCF pulldown over +UV IgG pulldown; †, significant enrichment of +UV αCTCF pulldown over −UV αCTCF pulldown. Ppia, Gapdh and Gtl2-as are negative controls.

(C) Coomassie staining of FLAG-CTCF and FLAG-GFP on an SDS-PAGE.

(D) RNA EMSA using 1.5 pmol of purified recombinant FLAG-CTCF or FLAG-GFP and 0.5 pmol of various in vitro-transcribed, end-labelled RNA probes. Comp, unlabelled competitors at 40× molar excess. *, CTCF-RNA shift. Jpx is positive control, Gapdh is negative control. Map of Xite/Tsix and EMSA probes are shown above the gels.

(E) RNA EMSA using 1.5 pmol of purified recombinant FLAG-CTCF or FLAG-GFP and 0.5 pmol of various Tsix RNA fragments (as shown in map in panel D). Comp, unlabelled competitors at 40× molar excess. *, CTCF-RNA shift.

(F) RNA EMSA with 0.5 pmol of purified Tsix probe d and 1.5 pmol of recombinant, purified CTCF full-length protein (FL), GST-CTCF fragments: N, N-terminal domain (aa 1-284); Zn, zinc-finger domain (aa 284-583); C, C-terminal domain (aa 583-727); or GST alone. Comp, unlabelled competitors at 40× molar excess. *, CTCF-RNA shift.

FIGS. 6A-E. Tsix RNA is Required for X-X Pairing (A) Map of Xic and pairing center, with positions for RIP qPCR primers and EMSA probes (arrowheads). Tsix antagomirs (asterisks): blue, shRNA; green, LNA; red, LNA. The Tsix major promoter accounts for 90% of Tsix transcripts. Position of the Tsix$^{TST}$ truncation allele is shown. Xite enhancer expresses an eRNA.

(B) RIP-RT-qPCR, + or −UV, on d3 female ES cells at various RNA domains with Tsix and Xite, with Jpx as positive control and U1 snRNA as negative control. qPCR positions shown in panel A. Representative results from two biological replicates shown. All values normalized to 1% of input RNA. Means±1 s. d. shown. p, determined by unpaired two-tailed Student t-tests comparing CTCF to IgG pull-downs in the +UV samples.

(C) Effect of TsixKD on pairing in female clones stably expressing shTsix versus shScr. DNA FISH using a two-probe combination of RP24 (centromeric) and pSx9 (Xist/Tsix) was performed. To exclude XO artifacts, only nuclei with two RP24 signals were scored. Cumulative frequency curves shown for decile with closest X-X distances. Whole distributions shown in FIG. 11A-C. The significance of the difference, p, in pairwise comparisons between ScrKD and TsixKD on various differentiation days is determined using unpaired two-tailed Student t-tests. Representative results shown for two independent biological replicates. Sample sizes, n: ScrKD: 261 (d0), 297 (d2), 295 (d4), 254 (d6); TsixKD: 263 (d0), 332 (d2), 282 (d4), 246 (d6).

(D,E) Quantitation of Tsix RNA after ScrKD versus TsixKD using two LNAs. Pairing analysis performed as in panel C. Whole distributions shown in FIG. 11A-C. Representative results shown from 2-3 independent biological replicates. D, sample sizes: ScrKD: 295 (d0), 289 (d3), 294

(d6); TsixKD: 277 (d0), 303 (d3), 310 (d6). E, sample sizes: ScrKD: 212 (d0), 186 (d3), 171 (d6); TsixKD, 205 (d0), 202 (d3), 186 (d6).

FIGS. 7A-F. Tsix RNA Recruits CTCF to Binding Sites in Xic (A) Map of Xic and pairing center, with positions for ChIP primers. Tsix antagomirs (asterisks) as in FIG. 6A.

(B) ChIP-qPCR in stable shTsix or shScr KD clones. Representative results from four biological replicates shown. Means±1 SD shown. p determined by unpaired two-tailed t-tests.

(C) EB outgrowth of shTsix KD ES cells was severely compromised. Scale bar, 100 μm.

(D) Pluripotency markers are appropriately downregulated in female shTsix KD cells, suggesting proper cell differentiation. Means±1 SD shown.

(E) Xist RNA FISH in shRNA TsixKD versus ScrKD during differentiation. P, determined by $x^2$ test comparing the distribution of Xist+ cells for ScrKD versus TsixKD from d0, d2, d4, and d6; [(observed-expected)$^2$/expected], degrees of freedom=3.

(F) Site-specific action of Tsix RNA facilitates locus-specific targeting of CTCF. POL-II transcribes Tsix RNA, which remains tethered to the site of synthesis as the RNA recruits CTCF to the locus. Co-transcriptional tethering, coupled to rapid turnover of Tsix ($t_{1/2}$, 30-60 min), enables the RNA to act in cis and in a locus-specific manner.

FIGS. 8A-B. CTCF is expressed at physiological levels in the inducible FLAG-CTCF mESC line.

(A) qRT-PCR of CTCF RNA level, normalized to GAPDH RNA level, with or without 24-hr induction with 1 μg/mL of doxycycline (Dox) induction.

(B) Immunoblot of nuclear lysate, with or without Dox induction, with a CTCF, a FLAG and a actin antibodies.

Figure 9A:
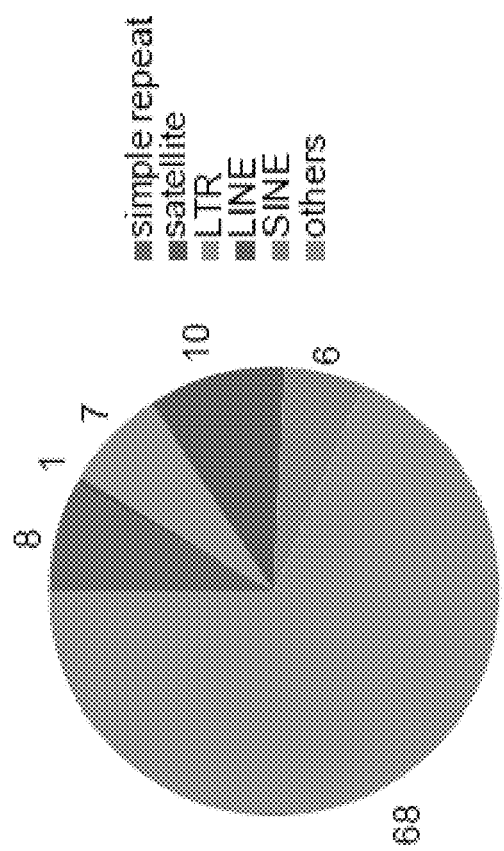
Figure 9B:
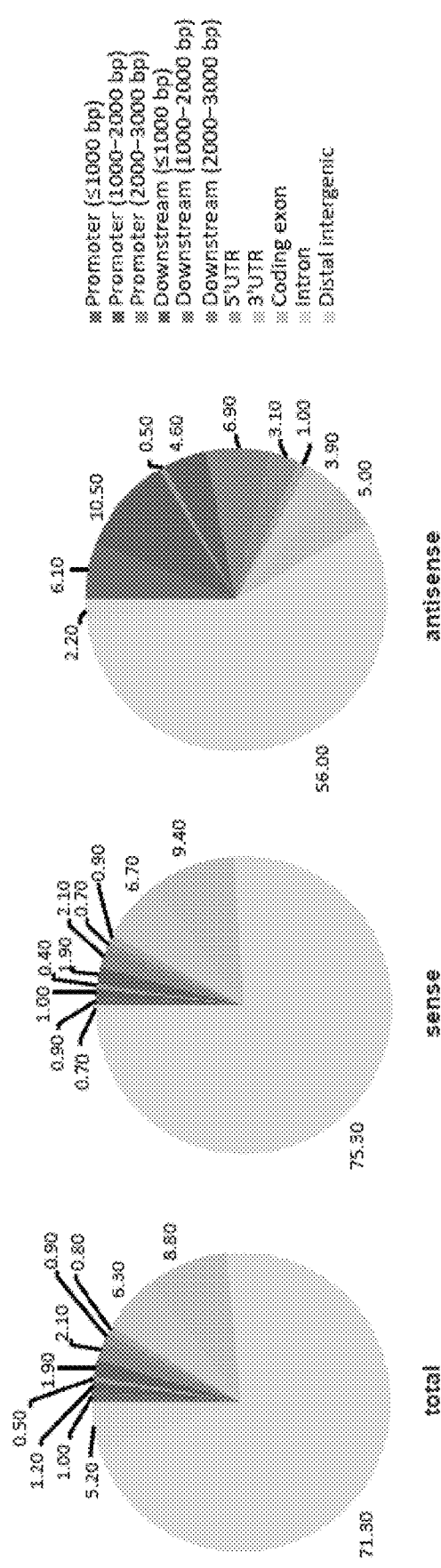
Figure 9C:
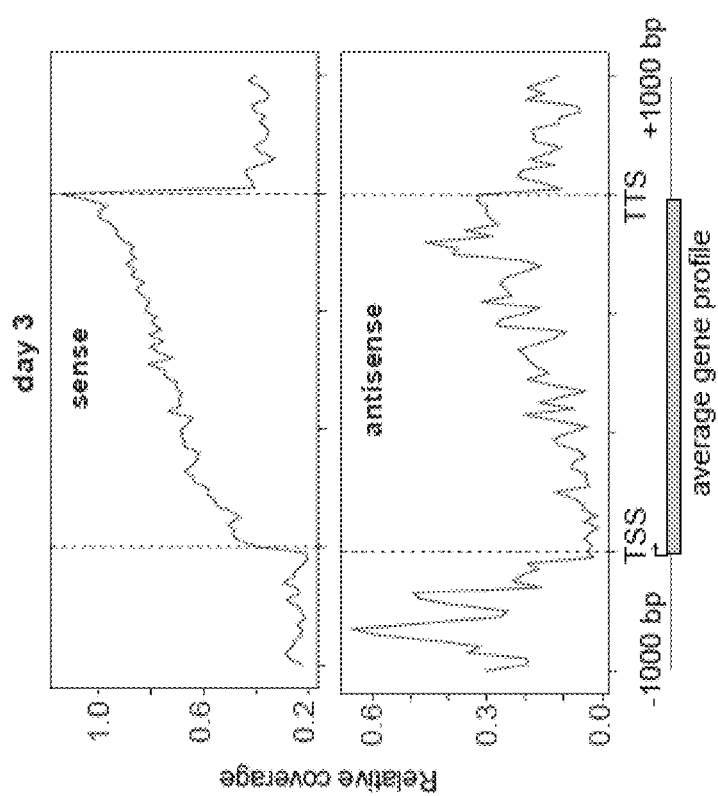

FIGS. 9A-C. Metagene analysis of CLIP-seq peaks in day 3 mESC.

(A) Percentage of multiple-mapping reads in d0+UV library that are in various classes of repetitive elements.

(B) Percentage of total, sense and antisense CTCF CLIP peaks, from d3 mESCs, in various genomic regions.

(C) Average CLIP peaks profile over a 3-kb metagene, as well as 1 kb up- or downstream, for d3 CLIP peaks that are sense or antisense to RefSeq annotated genes.

FIGS. 10A-D. The CTCF RNA interactome and epigenomic landscape at additional loci.

(A) 5' end of Gtl2 and upstream sequence. DMR, differentially methylated region.

(B) Nespas-Gnas cluster.

(C) H19. ICR, imprinting control region.

(D) Hoxa1, -2, -3, and upstream sequence.

Figure 11C:
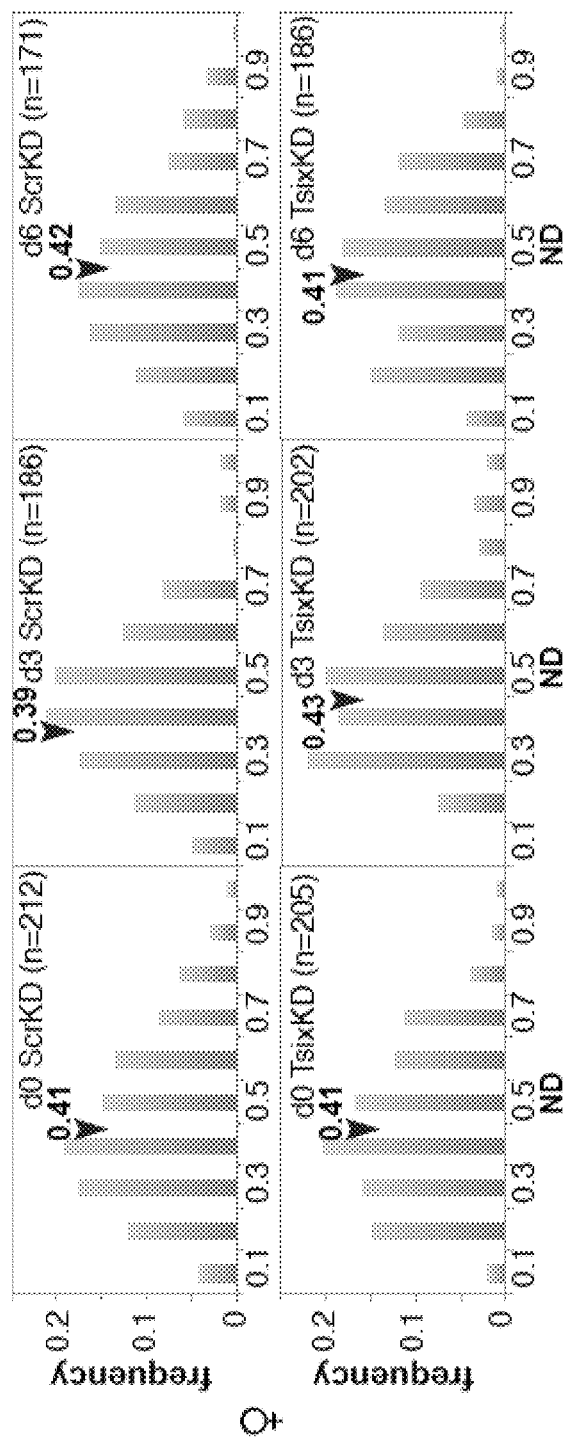

FIGS. 11A-C. Distribution of inter-Xic distances in control and Tsix-knockdown mESCs.

(A) Normalized distance (ND) distribution profiles of shScr and shTsix, corresponding to cumulative frequency (CF) curves in FIG. 6C. Arrowheads, Mean of ND. ND=X-X distance/d, where d=2*(nuclear area/π)$^{0.5}$. ND ranges from 0 to 1. Samples sizes are indicated in parentheses.

(B,C) ND distribution profiles of ScrKD and TsixKD, corresponding to CF curves in FIG. 6D,E. Arrowheads, Mean of ND. Representative results from three independent biological replicates.

Figure 12A:
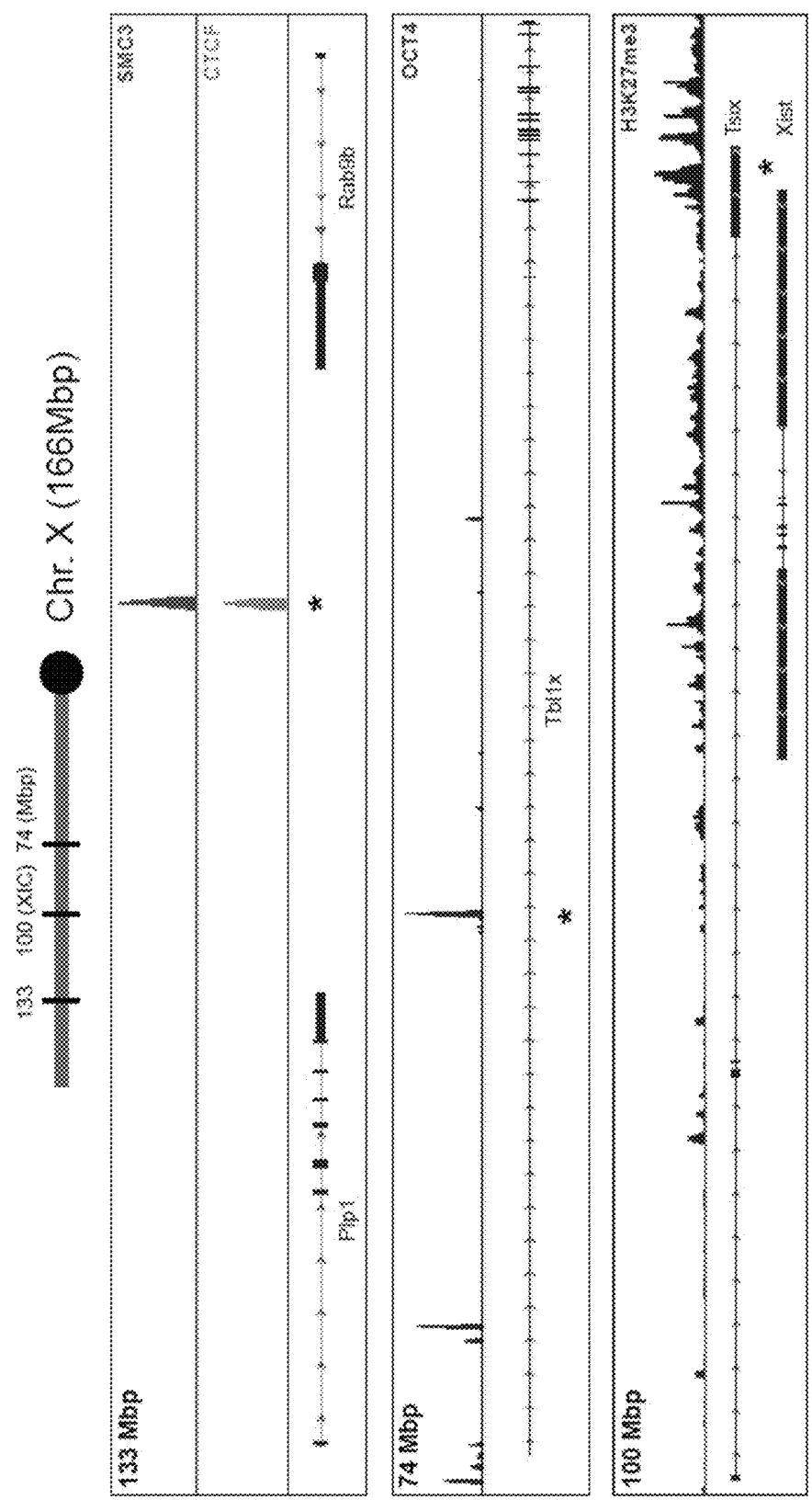
Figure 12B:
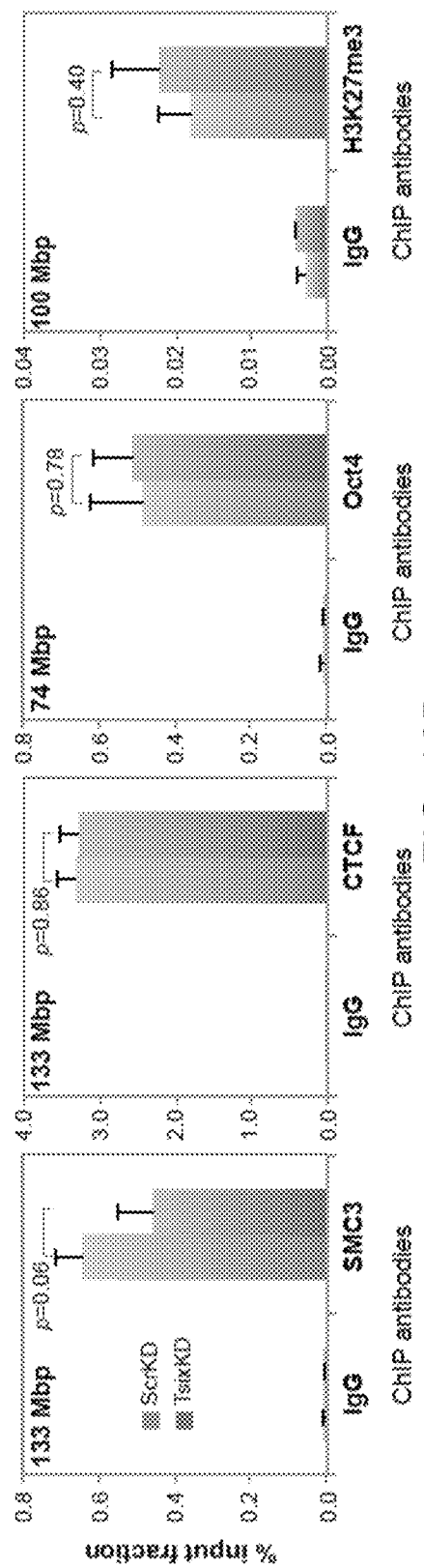

FIG. 12A-B. Occupancies of CTCF and OCT4 are not significantly affected in the regions outside of the pairing center (A) ChIP-seq analysis of SMC3, CTCF, OCT4, and H3K27me3 on X chromosome.

(B) ChIP-qPCR in shScr and shTsix at indicated sites of X chromosome. Means±1 S.D. shown. Three independent biological replicates shown.

Table 1. Human CTCF Binding Sites. Coordinates for the genomic equivalents of the sequences of the empirically determined human peaks plus 500 nucleotides of flanking sequence; the sequences coordinates are with reference to human genome build 19. Imp'd, imprinted; Onco, oncogene; T-supp., tumor suppressor.

Table 2. Human CTCF Binding Sites. Coordinates for the genomic equivalents of the sequences of the human Lift-Over peaks plus 500 nucleotides of flanking sequence; the sequences coordinates are with reference to human genome build 19. Imp'd, imprinted; Onco, oncogene; T-supp., tumor suppressor.

DETAILED DESCRIPTION

CTCF is a master regulator of the genome and a fastener that holds together higher-order genomic architecture. In light of recent advances that have uncovered roles for RNA in chromosome looping (Lai et al., 2013a; Li et al., 2013), it is tempting to speculate that RNA may play a general role in aiding CTCF weave genomic architecture. Thus, we speculated that CTCF might interact with RNA on a larger scale. Given that enhancer-directed chromosomal looping involves RNA-mediated interactions (Kung et al., 2013; Lai et al., 2013b), the present inventors set out to determine whether RNA may bind CTCF on a global scale and aid long-range chromatin interactions in some contexts. As described herein, CLIP-seq analysis was used to define an RNA interactome for CTCF in mESC and, in parallel, ChIP-seq was performed to investigate the epigenomic landscape relative to interacting transcripts. One novel function of CTCF-RNA interactions described herein is the in cis locus-specific targeting of CTCF to chromatin. Because Tsix remains tethered to the site of transcription, it serves as an allele-specific tether for CTCF and ensures locus-specific recruitment of an otherwise ubiquitous factor (FIG. 7F). By targeting CTCF to the pairing center, Tsix and Xite RNAs promote long-range chromosomal interaction. Because many imprinted noncoding RNAs such as H19, Nespas, and Gtl2 are cis-acting (Lee and Bartolomei, 2013) and interact directly with CTCF (FIG. 10A-D), CTCF may be recruited to nearby imprinting control regions via a similar RNA-mediated mechanism. CTCF-RNA interactions elsewhere may similarly mediate long-range interactions to form inter- and intra-chromosomal structures—structures that are now increasingly associated with CTCF binding activities (Handoko et al., 2011; Dixon et al., 2012; Sanyal et al., 2012; Shen et al., 2012; DeMare et al., 2013; Phillips-Cremins et al., 2013).

Using XCI as a model, the present analysis defines a large RNA interactome and chromosome-specific binding patterns, which together implicate RNAs in the recruitment of CTCF to the X-chromosome pairing center and in inter-chromosomal interactions. Relevant to this, the allele-specific binding patterns of CTCF to the Xi chromatin also merit future consideration (FIG. 4), as CTCF-RNA interactions near escapee genes (FIG. 4) may facilitate the genes' continued expression within facultative heterochromatin (Filippova et al., 2005; Li and Carrel, 2008; Calabrese et al., 2012; Mugford et al., 2014). As shown in the case of Kdm6a and Mid1 genes (FIG. 4C), there are Xi-specific CTCF peaks within/flanking theses escapees, which correlated CTCF-interacting transcripts. We suspect that these transcripts may recruit CTCF to the escapees to mediate escape from XCI.

In general, the CTCF-interacting RNAs may operate both in cis and in trans. For example, Tsix and Xite (FIG. 7) are cis-acting and are required to target CTCF to the pairing center of the X-inactivation center to enable long-range interactions between two X-chromosomes (inter-chromosomal pairing) and the initiation of Xist RNA expression from the future inactive X (FIGS. 6DE; 7AB). Other CTCF-associated RNAs such as Jpx (Sun et al., 2013) and SRA1 (Yao et al., 2010) are trans-acting. In the case of Jpx, interaction between the RNA and CTCF leads to eviction of CTCF from the promoter of Xist, which thereby induces expression of Xist RNA. CTCF may also function as either activator or repression of gene expression. As an example of CTCF-mediated repression, at the X-inactivation center, CTCF is recruited by Tsix and Xite RNA, and binding to Tsix/Xite operates as a transcriptional repressor of Xist (FIG. 6-7). At the H19-imprinted cluster, binding of CTCF to the imprinting control region (ICR) is also repressive for the linked Igf2 gene in cis (Wan and Bartolomei, 2008; Li et al., 2008; Ling et al., 2006; Lee and Bartolomei, 2013). Thus, selective activation such genes as Xist and Igf2 may be achieved by blocking CTCF recruitment to those location, potentially by interfering with the RNA-mediated recruitment of CTCF. As an example of an activator, in the same imprinted cluster H19-Igf2, CTCF binding to the ICR activates H19 in cis (while it represses the Igf2). Thus, CTCF's effect on gene expression is context-dependent and likely mediated by the intra- and inter-chromosomal loops generated by CTCF as its primary function. That is, CTCF is believed to be acting by forming functional chromosomal domains (e.g., intra-chromosomal loops to insulate one gene while repressing or activating a neighboring gene). Thus, this invention leverages the role of RNA in recruiting CTCF to modulate the expression of genes within such higher-order domains.

Provided herein are putative CTCF binding sites within an interacting transcript, against which antisense oligonucleotides could be designed to block CTCF-RNA interactions and thereby interfere with CTCF's chromatin binding and function in a locus-specific manner. A "binding site" is defined as a region on the interacting RNA that makes direct contact with CTCF protein. These binding sites were identified as statistically significant "peaks" in the CLIP-seq data. Listed in Tables 1-2 are the coordinates for the genomic equivalents of the sequences of the peaks of binding PLUS 500 nucleotides of flanking sequence; the sequences are provided in the sequence listing filed herewith. The additional 500 nucleotides are included because designing inhibitory nucleic acids against flanking sequences can be efficacious in targeting RNA-protein interactions (e.g., RepC RNA interaction with YY1—see Sarma et al., 2010; Jeon and Lee, 2011). Mouse-to-human LiftOver analysis and analysis in the UCSC genome browser of syntenic positions indicate the existence of similar transcripts in the human genome; the peaks are set out in Table 2. This process and LiftOver chains are generally described in Kent et al., *Proc. Nat'l Acad. Sci.*, 100(20) 11484-11489 (2003). Similar CTCF-interacting transcripts are believed to occur in the human system given the geographic and sequence similarities between the mouse and human transcripts. The data suggest that many if not all of the mouse CTCF-transcripts have direct counterparts in the human epigenome. Such direct counterparts in other species are termed "orthologous" herein. Empirically identified CTCF binding sites in the X Chromosome, are described herein (see Example 5 and Table 1). These CTCF binding sites may be functionally conserved without being highly conserved at the level of overall nucleotide identity. For example, mouse Xist shows only 76% overall nucleotide identity with human XIST using sliding 21-bp windows, or an overall sequence identity of only 60%. However, within specific functional domains, such as Repeat A of XIST, the degree of conservation can be >70% between different mammalian species. The crucial motif in Repeat A is the secondary structures formed by the repeat. A CTCF binding site interacting with CTCF may therefore be similarly low in overall conservation but still have conservation in secondary structure within specific domains of the RNA, and thereby demonstrate functional conservation with respect to recruitment of CTCF. Calculations of homology or sequence identity between sequences (the terms are used interchangeably herein) are performed as follows.

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences.

For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

There are several potential uses for the CTCF binding sites described herein in the expanded CTCF transcriptome: The CTCF binding sites themselves, or antagomirs and small molecules designed against them, can be utilized to modulate expression (either up or down) of CTCF target genes. In addition, the CTCF binding sites can be used to design and/or test inhibitory nucleic acids as described herein.

Methods of Treatment

The present disclosure provides therapeutics, useful in treating a number of conditions including but not limited to various autosomal imprinting disorders, cancer, and X-linked diseases, that are formulated by designing inhibitory nucleic acids, e.g., oligonucleotides, or TFOs that bind to the CTCF binding sites as described herein (e.g., in Tables 1-2). In some embodiments, the oligo is targeted to anywhere in the binding site sequence; in some embodiments, it is targeted to a sequence within a region that starts at nt+501 from the 5' end of a sequence in Tables 1-2, and ends at nt−501 from the 3' end. We envision that this approach could be used to (1) disrupt silencing of X-linked and autosomal genes controlled repressively by CTCF sites (e.g., all of the genes within a cluster), or to disrupt silencing of one specific gene; to (2) prevent the activation of X-linked and autosomal genes that are turned on by CTCF, as targeting the CTCF binding sites would enable repression of the disease gene of interest; and to (3) turn off escapee genes on the X-chromosome.

Treating X-Linked Disorders

This methodology is useful particularly in X-linked disorders, e.g., in heterozygous women who retain a wildtype copy of a gene on the Xi (See, e.g., Lyon, Acta Paediatr Suppl. 2002; 91(439):107-12; Carrell and Willard, Nature. 434(7031):400-4 (2005); den Vey ver, Semin Reprod Med. 19(2):183-91 (2001)). Again, without wishing to be bound by theory, administration of an inhibitory nucleic acid (e.g., oligonucleotide) targeting a strong or moderate binding site is expected to prevent CTCF recruitment to a specific X-linked gene cluster or to a specific gene on the inactive X, thereby reactivating the "good" or hypomorphic copy of the X-linked gene.

As a result of X-inactivation, heterozygous females are mosaic for X-linked gene expression; some cells express genes from the maternal X and other cells express genes from the paternal X. The relative ratio of these two cell populations in a given female is frequently referred to as the "X-inactivation pattern." One cell population may be at a selective growth disadvantage, resulting in clonal outgrowth of cells with one or the other parental X chromosome active; this can cause significant deviation or skewing from an expected mean X-inactivation pattern (i.e., 50:50). See, e.g., Plenge et al., Am. J. Hum. Genet. 71:168-173 (2002) and references cited therein.

In some embodiments, the present methods include targeting RNAs that recruit CTCF for either gene upregulation or downregulation. In this manner, specific genes of interest on the inactive X could be reactivated to treat X-linked diseases, when the inactivated X chromosome bears a functional or hypomorphic copy of the gene. In this manner, specific autosomal genes such as Igf2 could be reactivated. To downregulate genes, ASOs could be targeted to CTCF to silence H19, for example. The example of FIG. 6-7 shows that knocking down Tsix and Xite prevented CTCF recruitment, which in turn prevent inter-chromosomal pairing and the ability to induce Xist RNA. In another embodiment, targeting the CTCF binding sites could block the expression of disease genes that "escape" from XCI. Thus, the present methods can be used to treat disorders associated with X-inactivation, which includes those listed in Table A.

TABLE A

| Disorder | OMIM # | Locus | Gene |
| --- | --- | --- | --- |
| Dent's disease 1 | 300009 | Xp11.22 | CLCN5 |
| Testicular feminization syndrome | 300068 | Xq11-q12 | AR |
| Addison's disease with cerebral sclerosis | 300100 | Xq28 | ABCD1 |
| Adrenal hypoplasia | 300200 | XP21.3-p21.2 | DAX1 |
| siderius X-linked mental retardation syndrome | 300263 | Xp11.22 | PHF8 |
| Agammaglobulinaemia, Bruton type | 300300 | Xq21.3-q22 | BTK |
| Choroidoretinal degeneration | 300389 | Xp21.1 | RPGR |
| Choroidaemia | 300390 | Xq21.2 | CHM |
| Albinism, ocular | 300500 | Xp22.3 | OA1 |
| Dent's disease 2 | 300555 | Xq25-q26 | OCRL |
| fragile X syndrome | 300624 | Xq27.3 | FMR1 |
| Rett/Epileptic encephalopathy, early infantile, 2 | 300672 | Xp22.13 | CDKL5 |
| Albinism-deafness syndrome | 300700 | Xq26.3-q27.1 | ADFN |
| paroxysmal nocturnal hemoglobinuria | 300818 | Xp22.2 | PIGA |

TABLE A-continued

| Disorder | OMIM # | Locus | Gene |
| --- | --- | --- | --- |
| Aldrich syndrome | 301000 | Xp11.23-p11.22 | WAS |
| Alport syndrome | 301050 | Xq22.3 | COL4A5 |
| Anaemia, hereditary hypochromic | 301300 | Xp11.21 | ALAS2 |
| Anemia, sideroblastic, with ataxia | 301310 | Xq13.3 | ABCB7 |
| Fabry disease | 301500 | Xq22 | GLA |
| Spinal muscular atrophy 2 | 301830 | Xp11.23 | UBA1 |
| Cataract, congenital | 302200 | Xp | CCT |
| Charcot-Marie-Tooth, peroneal | 302800 | Xq13.1 | GJB1 |
| Spastic paraplegia | 303350 | Xq28 | L1CAM |
| Colour blindness | 303800 | Xq28 | OPN1MW |
| Diabetes insipidus, nephrogenic | 304800 | Xq28 | AVPR2 |
| Dyskeratosis congenita | 305000 | Xq28 | DKC1 |
| Ectodermal dysplasia, anhidrotic | 305100 | Xq12-q13.1 | ED1 |
| Faciogenital dysplasia (Aarskog syndrome) | 305400 | Xp11.21 | FGD1 |
| Glucose-6-phosphate dehydrogenase deficiency | 305900 | Xq28 | G6PD |
| Glycogen storage disease type VIII | 306000 | Xp22.2-p22.1 | PHKA2 |
| Gonadal dysgenesis (XY female type) | 306100 | Xp22.11-p21.2 | GDXY |
| Granulomatous disease (chronic) | 306400 | Xp21.1 | CYBB |
| Haemophilia A | 306700 | Xq28 | F8 |
| Haemophilia B | 306900 | Xq27.1-q27.2 | F9 |
| Hydrocephalus (aqueduct stenosis) | 307000 | Xq28 | L1CAM |
| Hypophosphataemic rickets | 307800 | Xp22.2-p22.1 | PHEX |
| Lesch-Nyhan syndrome (hypoxanthine-guanine-phospho-ribosyl transferase deficiency) | 308000 | Xq26-q27.2 | HPRT1 |
| Incontinentia pigmenti | 308300 | Xq28 | IKBKG |
| Kallmann syndrome | 308700 | Xp22.3 | KAL1 |
| Keratosis follicularis spinulosa | 308800 | Xp22.1 | SAT |
| Lowe (oculocerebrorenal) syndrome | 309000 | Xq26.1 | OCRL |
| Menkes syndrome | 309400 | Xq12-q13 | ATP7A |
| Renpenning Syndrome | 309500 | Xp11.23 | PQBP1 |
| Mental retardation, with or without fragile site (numerous specific types) | 309530 | Xp11.3-q21.1 | MRX1 |
| Coffin-Lowry syndrome | 309580 | Xq13 | ATRX |
| Microphthalmia with multiple anomalies (Lenz syndrome) | 309800 | Xq27-q28 | MAA |
| Muscular dystrophy (Becker, Duchenne and Emery-Dreifuss types) | 310300 | Xq28 | EMD |
| Myotubular myopathy | 310400 | Xq28 | MTM1 |
| Night blindness, congenital stationary | 310500 | Xp11.4 | CSNB1 |
| Norrie's disease (pseudoglioma) | 310600 | Xp11.4 | NDP |
| Nystagmus, oculomotor or 'jerky' | 310700 | Xq26-q27 | NYS1 |
| Orofaciodigital syndrome (type I) | 311200 | Xp22.3-p22.2 | OFD1 |
| Ornithine transcarbamylase deficiency (type I hyperammonaemia) | 311250 | Xp21.1 | OTC |
| Phosphoglycerate kinase deficiency | 311800 | Xq13 | PGK1 |
| Phosphoribosylpyrophosphate synthetase deficiency | 311850 | Xq22-q24 | PRPS1 |
| Retinitis pigmentosa | 312610 | Xp21.1 | RPGR |
| Retinoschisis | 312700 | Xp22.2-p22.1 | RS1 |
| Rett syndrome | 312750 | Xq28, Xp22 | MECP2 |
| Muscular atrophy/Dihydro-testosterone receptor deficiency | 313200 | Xq11-q12 | AR |
| Spinal muscular atrophy | 313200 | Xq11-q12 | AR |
| Spondyloepiphyseal dysplasia tarda | 313400 | Xp22.2-p22.1 | SEDL |
| Thrombocytopenia, hereditary | 313900 | Xp11.23-p11.22 | WAS |
| Thyroxine-binding globulin, absence | 314200 | Xq22.2 | TBG |
| McLeod syndrome | 314850 | Xp21.1 | XK |

Table A was adapted in part from Germain, "Chapter 7: General aspects of X-linked diseases" in Fabry Disease: Perspectives from 5 Years of FOS. Mehta A, Beck M, Sunder-Plassmann G, editors. (Oxford: Oxford PharmaGenesis; 2006).

Treating Cancer

The methods described herein can also be used to treat a cancer in a subject by administering to the subject a composition (e.g., as described herein) comprising an inhibitory nucleic acid or TFO that binds to a CTCF binding site associated with a tumor suppressor, or cancer-suppressing gene, or imprinted gene and/or other growth-suppressing genes in any of Tables 1-2. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease. With respect to cancer, treating includes inhibiting tumor cell proliferation, increasing tumor cell death or killing, inhibiting rate of tumor cell growth or metastasis, reducing size of tumors, reducing number of tumors, reducing number of metastases, increasing 1-year or 5-year survival rate.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung (e.g., small cell, non-small cell, squamous, adenocarcinoma), breast, thyroid, lymphoid, gastrointestinal, genito-urinary tract, kidney, bladder, liver (e.g. hepatocellular cancer), pancreas, ovary, cervix, endometrium, uterine, prostate, brain, as well as adenocarcinomas which include malignancies such as most colon cancers, colorectal cancer, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

Additional examples of proliferative disorders include hematopoietic neoplastic disorders.

As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In some embodiments, specific cancers that can be treated using the methods described herein are listed in the categories herein, for example, and include, but are not limited to: breast, lung, prostate, CNS (e.g., glioma), salivary gland, prostate, ovarian, and leukemias (e.g., ALL, CML, or AML). Associations of these genes with a particular cancer are known in the art, e.g., as described in Futreal et al., Nat Rev Cancer. 2004; 4:177-83; and The COSMIC (Catalogue of Somatic Mutations in Cancer) database and website, Bamford et al., Br J Cancer. 2004; 91:355-8; see also Forbes et al., Curr Protoc Hum Genet. 2008; Chapter 10; Unit 10.11, and the COSMIC database, e.g., v. 50 (Nov. 30, 2010). It is understood that reference to any particular type of cancer herein means that patients with other types of cancer, i.e., cancer in general, may be treated.

In addition, the methods described herein can be used for modulating (e.g., enhancing or decreasing) pluripotency of a stem cell and to direct stem cells down specific differentiation pathways to make endoderm, mesoderm, ectoderm, and their developmental derivatives. To modulate, e.g., decrease, increase, maintain, or enhance pluripotency, the methods include introducing into the cell an inhibitory nucleic acid that specifically binds to, or is complementary to, a CTCF-binding RNA or RNA domain as set forth herein. Stem cells useful in the methods described herein include adult stem cells (e.g., adult stem cells obtained from the inner ear, bone marrow, mesenchyme, skin, fat, liver, muscle, or blood of a subject, e.g., the subject to be treated); embryonic stem cells, or stem cells obtained from a placenta or umbilical cord; progenitor cells (e.g., progenitor cells derived from the inner ear, bone marrow, mesenchyme, skin, fat, liver, muscle, or blood); and induced pluripotent stem cells (e.g., iPS cells).

Methods of Targeting Genes Modulated by CTCF

The methods described herein can be used to specifically re-activate or repress one or more genes suppressed by CTCF, by targeting CTCF binding sites (i.e., within 500 nts of a peak sequence) as described herein, to disrupt RNA-mediated silencing or enhancement in cis on the inactive X-chromosome. The CTCF-binding RNAs can be noncoding (long noncoding RNA, lncRNA) or occasionally part of a coding mRNA; for simplicity, we will refer to them together as CTCF-associated RNAs (caRNAs) henceforth.

In the present methods, inhibitory nucleic acids targeting the CTCF binding sites, or complementary or identical to a CTCF binding site in the genome, are used to modulate gene expression in a cell, e.g., a cancer cell, a stem cell, or other normal cell types for gene or epigenetic therapy. The nucleic acids used in the methods described herein are termed "inhibitory" because they inhibit the CTCF-mediated repression or enhancement of a specified gene, by binding to a CTCF-binding sequence on the caRNA itself (e.g., an antisense oligo that is complementary to the CTCF-binding region of the caRNA) or by binding to a CTCF binding site as described herein in the genome, and (without wishing to be bound by theory) preventing binding or recruitment of CTCF to the binding site and thus disrupting CTCF-mediated silencing or enhancement in the region of the binding site. The cells can be in vitro, including ex vivo, or in vivo (e.g., in a subject who has cancer, e.g., a tumor). In some embodiments, the methods include introducing into the cell an inhibitory nucleic acid that is modified in some way, e.g., that differs from the endogenous caRNA or CTCF binding site by including one or more modifications to the backbone or bases as described herein for inhibitory nucleic acids. Such modified oligos are also within the scope of the present invention.

In some embodiments, the methods include introducing into the cell an inhibitory nucleic acid that specifically binds, or is complementary, to a strong or moderate binding site or a long non-coding RNA described herein. A nucleic acid that binds "specifically" binds primarily to the target, i.e., to the CTCF binding site to inhibit regulatory function or binding of CTCF to the caRNA or DNA but not to other non-target RNAs. The specificity of the nucleic acid interaction thus refers to its function (e.g., inhibiting the CTCF-associated repression or enhancement of gene expression) rather than its hybridization capacity. Inhibitory nucleic acids may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects. These methods can be used to treat a subject, e.g., a subject with an X-linked condition or cancer, by administering to the subject a composition (e.g., as described herein) comprising an inhibitory nucleic acid that binds to a long non-coding RNA (e.g., an inhibitory nucleic acid that binds to a CTCF binding site described herein, e.g., as described in Tables 1-2) that is associated with a disease gene. Examples of genes involved in X-linked diseases are shown in Table A.; examples of oncogenes, tumor suppressors, and imprinted genes are shown in Tables 1-2.

The methods described herein can be used for modulating expression of oncogenes and tumor suppressors in cells, e.g., cancer cells. For example, to decrease expression of an oncogene in a cell, the methods include introducing into the cell an inhibitory nucleic acid that binds to a CTCF-binding region of a CTCF associated RNA or DNA as described herein, that regulates the genes, e.g., the tumor suppressors, oncogenes, and/or other growth-promoting genes in Tables 1-2.

As another example, to increase expression of a tumor suppressor in a cell, the methods include introducing into the cell an inhibitory nucleic acid or small molecule that specifically binds, or is complementary, to a CTCF-associated RNA targeting a tumor suppressor as set forth in Tables 1-2, e.g., in subjects with cancer, e.g., lung adenocarcinoma patients. In some embodiments, the methods include introducing into the cell an inhibitory nucleic acid that specifically binds, or is complementary, to a CTCF-associated RNA targeting an imprinted gene as set forth in Tables 1-2, or an X-linked gene as listed in Table A. A nucleic acid that binds "specifically" binds primarily to the target lncRNA or related lncRNAs to inhibit regulatory function of the lncRNA but not of other non-target RNAs. The specificity of the nucleic acid interaction thus refers to its function (e.g. inhibiting the CTCF-associated repression of gene expression) rather than its hybridization capacity. Inhibitory nucleic acids may exhibit nonspecific binding to other sites in the genome or other mRNAs, without interfering with binding of other regulatory proteins and without causing degradation of the non-specifically-bound RNA. Thus this nonspecific binding does not significantly affect function of other non-target RNAs and results in no significant adverse effects.

As used herein, treating includes "prophylactic treatment" which means reducing the incidence of or preventing (or reducing risk of) a sign or symptom of a disease in a patient at risk for the disease, and "therapeutic treatment", which means reducing signs or symptoms of a disease, reducing progression of a disease, reducing severity of a disease, in a patient diagnosed with the disease.

In some embodiments, the methods described herein include administering a composition, e.g., a sterile composition, comprising an inhibitory nucleic acid that is complementary to a CTCF binding site described herein. Inhibitory nucleic acids for use in practicing the methods described herein can be an antisense or small interfering RNA, including but not limited to an shRNA or siRNA. In some embodiments, the inhibitory nucleic acid is a modified nucleic acid polymer (e.g., a locked nucleic acid (LNA) molecule).

Inhibitory nucleic acids have been employed as therapeutic moieties in the treatment of disease states in animals, including humans. Inhibitory nucleic acids can be useful therapeutic modalities that can be configured to be useful in treatment regimens for the treatment of cells, tissues and animals, especially humans.

For therapeutics, an animal, preferably a human, suspected of having cancer is treated by administering an inhibitory nucleic acid in accordance with this invention. For example, in one non-limiting embodiment, the methods comprise the step of administering to the animal in need of treatment, a therapeutically effective amount of an inhibitory nucleic acid as described herein.

Inhibitory Nucleic Acids

Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, molecules comprising modified bases, locked nucleic acid molecules (LNA molecules), antagomirs, peptide nucleic acid molecules (PNA molecules), and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa);

small activating RNAs (saRNAs), or combinations thereof. See, e.g., WO 2010040112. However, in some embodiments the inhibitory nucleic acid is not an miRNA, an stRNA, an shRNA, an siRNA, an RNAi, or a dsRNA.

In some embodiments, the inhibitory nucleic acids are 10 to 50, 13 to 50, or 13 to 30 nucleotides in length. One having ordinary skill in the art will appreciate that this embodies oligonucleotides having antisense (complementary) portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. It is understood that non-complementary bases may be included in such inhibitory nucleic acids; for example, an inhibitory nucleic acid 30 nucleotides in length may have a portion of 15 bases that is complementary to the targeted RNA. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense (complementary) portions of 12, 13, 14, 15, 16, 17, 18, 19, 20, 21, 22, 23, 24, 25, 26, 27, 28, 29 or 30 nucleotides in length, or any range therewithin.

Preferably the inhibitory nucleic acid comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5, 220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone], $CH_2$—O—N ($CH_3$)—$CH_2$, $CH_2$—N ($CH_3$)—N ($CH_3$)—$CH_2$ and O—N ($CH_3$)—$CH_2$—$CH_2$ backbones, wherein the native phosphodiester backbone is represented as O—P—O—CH,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5, 177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties). Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues.

Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide. PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-O,4'-C-ethylene-bridged nucleic acids.

Examples of LNAs are described in WO 2008/043753 and WO2007031091 and include compounds of the following formula.

Scheme 1

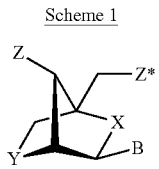

where X and Y are independently selected among the groups —O—, —S—, —N(H)—, N(R)—, —CH2- or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligomer of the invention comprises at least one LNA unit according any of the formulas Scheme 2

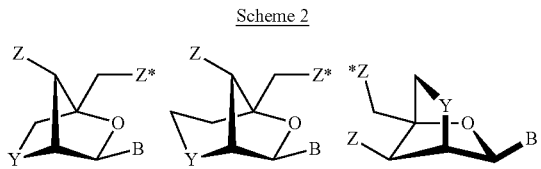

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl. Preferably, the Locked Nucleic Acid (LNA) used in an oligomeric compound, such as an antisense oligonucleotide, as described herein comprises at least one nucleotide comprises a Locked Nucleic Acid (LNA) unit according any of the formulas shown in Scheme 2 of PCT/DK2006/000512 (WO2007031091).

Preferably, the LNA used in the oligomer of the invention comprises internucleoside linkages selected from —O—P(O)$_2$—O—, —O—P(O,S)—O—, —O—P(S)$_2$—O—, —S—P(O)$_2$—O—, —S—P(O,X)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PONR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—O—O—, where R$^H$ is selected from hydrogen and C$_{1-4}$-alkyl.

Specifically preferred LNA units are shown in scheme 3:

Scheme 3

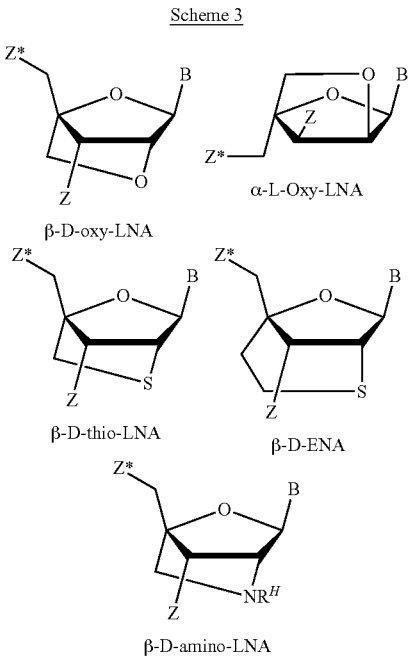

β-D-oxy-LNA

α-L-Oxy-LNA

β-D-thio-LNA

β-D-ENA

β-D-amino-LNA

The term "thio-LNA" comprises a locked nucleotide in which at least one of X or Y in the general formula above is selected from S or —CH2-S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—, Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail below. One or more substituted sugar moieties can also be included, e.g., one of the following at the 2' position: OH, SH, SCH$_3$, F, OCN, OCH$_3$OCH$_3$, OCH$_3$O(CH$_2$)n CH$_3$, O(CH$_2$)n NH$_2$ or O(CH$_2$)n CH$_3$ where n is from 1 to about 10; Ci to C10 lower alkyl, alkoxyalkoxy, substituted lower alkyl, alkaryl or aralkyl; Cl; Br; CN; CF3; OCF3; O—, S—, or N-alkyl; O—, S—, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$Ch$_2$OCH$_3$, also known as 2'-O-(2-methoxyethyl)] (Martin et al, Helv. Chim. Acta, 1995, 78, 486). Other preferred modifications include 2'-methoxy (2'-O-CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2<0>C. (Sanghvi, in Crooke, and Lebleu, eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175, 273; 5, 367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. For example, one or more inhibitory nucleic acids, of the same or different types, can be conjugated to each other; or inhibitory nucleic acids can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxy-cholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552, 538; 5,578,717, 5,580,731; 5,580,731; 5,591,584; 5,109,124; 5,118,802; 5,138,045; 5,414,077; 5,486, 603; 5,512,439; 5,578,718; 5,608,046; 4,587,044; 4,605,735; 4,667,025; 4,762, 779; 4,789,737; 4,824,941; 4,835,263; 4,876,335; 4,904,582; 4,958,013; 5,082, 830; 5,112,963; 5,214,136; 5,082,830; 5,112,963; 5,214,136; 5, 245,022; 5,254,469; 5,258,506; 5,262,536; 5,272,250; 5,292,873; 5,317,098; 5,371,241, 5,391, 723; 5,416,203, 5,451,463; 5,510,475; 5,512,667; 5,514,785; 5, 565,552; 5,567,810; 5,574,142; 5,585,481; 5,587,371; 5,595,726; 5,597,696; 5,599,923; 5,599, 928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target a CTCF binding site, e.g., hybridize sufficiently well and with sufficient biological functional specificity, to give the desired effect. "Complementary" refers to the capacity for pairing, through base stacking and specific hydrogen bonding, between two sequences comprising naturally or non-naturally occurring (e.g., modified as described above) bases (nucleosides) or analogs thereof. For example, if a base at one position of an inhibitory nucleic acid is capable of hydrogen bonding with a base at the corresponding position of a CTCF binding site, then the bases are considered to be complementary to each other at that position. 100% complementarity is not required. As noted above, inhibitory nucleic acids can comprise universal bases, or inert abasic spacers that provide no positive or negative contribution to hydrogen bonding. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as such as 3-nitropyrrole or 5-nitroindole can hybridize to and are considered complementary to any A, C, U, or T. Nichols et al., Nature, 1994; 369:492-493 and Loakes et al., Nucleic Acids Res., 1994; 22:4039-4043. Inosine (I) has also been considered in the art to be a universal base and is considered complementary to any A, C, U, or T. See Watkins and SantaLucia, Nucl. Acids Research, 2005; 33 (19): 6258-6267. In some embodiments, the location on a target CTCF binding site to which an inhibitory nucleic acid hybridizes is a region to which a protein binding partner binds. The identification of these binding sites is described in the Examples below. Routine methods can be used to design an inhibitory nucleic acid that binds to a selected strong or moderate binding site sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid. For example, methods of designing oligonucleotides similar to the inhibitory nucleic acids described herein, and various options for modified chemistries or formats, are exemplified in Lennox and Behlke, Gene Therapy (2011) 18: 1111-1120, which is incorporated herein by reference in its entirety, with the understanding that the inhibitory oligonucleotides of the present disclosure do not target miRNA 'seed regions'.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same CTCF binding site beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target with complementary inhibitory nucleic acids.

In the context of the present disclosure, hybridization means base stacking and hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as the term is used in the art, refers to the capacity for precise pairing between two nucleotides. For example, if a nucleotide at a certain position of an oligonucleotide is capable of hydrogen bonding with a nucleotide at the same position of a CTCF binding site molecule, then the inhibitory nucleic acid and the CTCF binding site are considered to be complementary to each other at that position. The inhibitory nucleic acids and the CTCF binding site are complementary to each other when a sufficient number of corresponding positions in each molecule are occupied by nucleotides that can hydrogen bond with each other through their bases. Thus, "specifically hybridizable" and "complementary" are terms which are used to indicate a sufficient degree of complementarity or precise pairing such that stable and specific binding occurs between the inhibitory nucleic acid and the CTCF binding site target. For example, if a base at one position of an inhibitory nucleic acid is capable of hydrogen bonding with a base at the corresponding position of a CTCF binding site, then the bases are considered to be complementary to each other at that position. 100% complementarity is not required. It is understood in the art that a complementary nucleic acid sequence need not be 100% complementary to that of its target nucleic acid to be specifically hybridizable. A complementary nucleic acid sequence for purposes of the present methods is specifically hybridizable when binding of the sequence to the target CTCF binding site molecule interferes with the normal function of the target CTCF binding site to cause a loss of activity (e.g., inhibiting CTCF-associated repression with consequent up-regulation of gene expression) and there is a sufficient degree of complementarity to avoid non-specific binding of the sequence to non-target CTCF binding site sequences under conditions in which avoidance of the non-specific binding is desired, e.g., under physiological conditions in the case of in vivo assays or therapeutic treatment, and in the case of in vitro assays, under conditions in which the assays are performed under suitable conditions of stringency.

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS.

Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, N.Y.

In general, the inhibitory nucleic acids useful in the methods described herein have at least 80% sequence complementarity to a target region within the target nucleic acid, e.g., 90%, 95%, or 100% sequence complementarity to the target region within a CTCF binding site.

For example, an antisense compound in which 18 of 20 nucleobases of the antisense oligonucleotide are complementary, and would therefore specifically hybridize, to a target region would represent 90 percent complementarity. Percent complementarity of an inhibitory nucleic acid with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention that hybridize to a CTCF binding site are identified through routine experimentation. In general the inhibitory nucleic acids must retain specificity for their target, i.e., either do not directly bind to, or do not directly significantly affect expression levels of, transcripts other than the intended target.

Target-specific effects, with corresponding target-specific functional biological effects, are possible even when the inhibitory nucleic acid exhibits non-specific binding to a large number of non-target RNAs. For example, short 8 base long inhibitory nucleic acids that are fully complementary to a CTCF binding site may have multiple 100% matches to hundreds of sequences in the genome, yet may produce target-specific effects, e.g. upregulation of a specific target gene through inhibition of CTCF activity. 8-base inhibitory nucleic acids have been reported to prevent exon skipping with with a high degree of specificity and reduced off-target effect. See Singh et al., RNA Biol., 2009; 6(3): 341-350. 8-base inhibitory nucleic acids have been reported to interfere with miRNA activity without significant off-target effects. See Obad et al., Nature Genetics, 2011; 43: 371-378. For further disclosure regarding inhibitory nucleic acids, please see US2010/0317718 (antisense oligos); US2010/0249052 (double-stranded ribonucleic acid (dsRNA)); US2009/0181914 and US2010/0234451 (LNA molecules); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides.

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to a CTCF binding site in vitro, and are expected to inhibit the activity of CTCF in vivo. Thus, oligonucleotides are chosen that are sufficiently complementary to the target, i.e., that hybridize sufficiently well and with sufficient biological functional specificity, to give the desired effect.

Modified Bases, Including Locked Nucleic Acids (LNAs)

In some embodiments, the inhibitory nucleic acids used in the methods described herein comprise one or more modified bonds or bases. Modified bases include phosphorothioate, methylphosphonate, peptide nucleic acids, or locked nucleic acids (LNAs). Preferably, the modified nucleotides are part of locked nucleic acid molecules, including [alpha]-L-LNAs. LNAs include ribonucleic acid analogues wherein the ribose ring is "locked" by a methylene bridge between the 2'-oxygen and the 4'-carbon—i.e., oligonucleotides containing at least one LNA monomer, that is, one 2'-O,4'-C-methylene-β-D-ribofuranosyl nucleotide. LNA bases form standard Watson-Crick base pairs but the locked configuration increases the rate and stability of the basepairing reaction (Jepsen et al., Oligonucleotides, 14, 130-146 (2004)). LNAs also have increased affinity to base pair with RNA as compared to DNA. These properties render LNAs especially useful as probes for fluorescence in situ hybridization (FISH) and comparative genomic hybridization, as knockdown tools for miRNAs, and as antisense oligonucleotides to target mRNAs or other RNAs, e.g., CTCF binding sites as described herien.

The modified base/LNA molecules can include molecules comprising, e.g., 10-30, e.g., 12-24, e.g., 12, 13, 14, 15, 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the CTCF binding site. The modified base/LNA molecules can be chemically synthesized using methods known in the art.

The modified base/LNA molecules can be designed using any method known in the art; a number of algorithms are known, and are commercially available (e.g., on the internet, for example at exiqon.com). See, e.g., You et al., Nuc. Acids. Res. 34:e60 (2006); McTigue et al., Biochemistry 43:5388-405 (2004); and Levin et al., Nuc. Acids. Res. 34:e142 (2006).

For example, "gene walk" methods, similar to those used to design antisense oligos, can be used to optimize the inhibitory activity of a modified base/LNA molecule; for example, a series of oligonucleotides of 10-30 nucleotides spanning the length of a target CTCF binding site can be prepared, followed by testing for activity. Optionally, gaps, e.g., of 5-10 nucleotides or more, can be left between the LNAs to reduce the number of oligonucleotides synthesized and tested. GC content is preferably between about 30-60%. General guidelines for designing modified base/LNA molecules are known in the art; for example, LNA sequences will bind very tightly to other LNA sequences, so it is preferable to avoid significant complementarity within an LNA molecule. Contiguous runs of three or more Gs or Cs, or more than four LNA residues, should be avoided where possible (for example, it may not be possible with very short (e.g., about 9-10 nt) oligonucleotides). In some embodiments, the LNAs are xylo-LNAs.

In some embodiments, the modified base/LNA molecules can be designed to target a specific region of the CTCF binding site. For example, a specific functional region can be targeted, e.g., a region comprising a known RNA localization motif (i.e., a region complementary to the target nucleic acid on which the CTCF binding site acts), or a region comprising a known protein binding region, e.g., a CTCF binding region. Sarma et al., "Locked nucleic acids (LNAs) reveal sequence requirements and kinetics of Xist RNA localization to the X chromosome." PNAS published ahead of print Dec. 6, 2010, doi:10.1073/pnas.1009785107. Alternatively or in addition, highly conserved regions can be targeted, e.g., regions identified by aligning sequences from disparate species such as primate (e.g., human) and rodent (e.g., mouse) and looking for regions with high degrees of identity. Percent identity can be determined routinely using basic local alignment search tools (BLAST programs) (Altschul et al., J. Mol. Biol., 1990, 215, 403-410; Zhang and Madden, Genome Res., 1997, 7, 649-656), e.g., using the default parameters.

For additional information regarding LNA molecules see U.S. Pat. Nos. 6,268,490; 6,734,291; 6,770,748; 6,794,499; 7,034,133; 7,053,207; 7,060,809; 7,084,125; and 7,572,582; and U.S. Pre-Grant Pub. Nos. 20100267018; 20100261175;

and 20100035968; Koshkin et al. Tetrahedron 54, 3607-3630 (1998); Obika et al. Tetrahedron Lett. 39, 5401-5404 (1998); Jepsen et al., Oligonucleotides 14:130-146 (2004); Kauppinen et al., Drug Disc. Today 2(3):287-290 (2005); and Ponting et al., Cell 136(4):629-641 (2009), and references cited therein.

As demonstrated herein, LNA molecules can be used as a valuable tool to manipulate and aid analysis of long nuclear ncRNAs. Advantages offered by an LNA molecule-based system are the relatively low costs, easy delivery, and rapid action. While other inhibitory nucleic acids may exhibit effects after longer periods of time, LNA molecules exhibit effects that are more rapid, e.g., a comparatively early onset of activity, are fully reversible after a recovery period following the synthesis of new CTCF binding site, and occur without causing substantial or substantially complete RNA cleavage or degradation. One or more of these design properties may be desired properties of the inhibitory nucleic acids of the invention. Additionally, LNA molecules make possible the systematic targeting of domains within much longer nuclear transcripts. Although a PNA-based system has been described earlier, the effects on Xi were apparent only after 24 hours (Beletskii et al., Proc Natl Acad Sci USA 98:9215-9220 (2001)). The LNA technology enables high-throughput screens for functional analysis of long non-coding RNAs and also provides a novel tool to manipulate chromatin states in vivo for therapeutic applications.

In various related aspects, the methods described herein include using LNA molecules to target CTCF binding sites for a number of uses, including as a research tool to probe the function of a specific CTCF binding site, e.g., in vitro or in vivo. The methods include selecting one or more desired CTCF binding sites, designing one or more LNA molecules that target the CTCF binding site, providing the designed LNA molecule, and administering the LNA molecule to a cell or animal. The methods can optionally include selecting a region of the CTCF binding site and designing one or more LNA molecules that target that region of the CTCF binding site.

Aberrant imprinted gene expression is implicated in several diseases including Long QT syndrome, Beckwith-Wiedemann, Prader-Willi, and Angelman syndromes, as well as behavioral disorders and carcinogenesis (see, e.g., Falls et al., Am. J. Pathol. 154:635-647 (1999); Lalonde, Annu Rev Genet 30:173-195 (1996); Hall Annu Rev Med. 48:35-44 (1997)). LNA molecules can be created to treat such imprinted diseases. As one example, the long QT Syndrome can be caused by a K+ gated Calcium-channel encoded by Kcnql. This gene is regulated by its antisense counterpart, the long noncoding RNA, Kcnqlotl (Pandey et al., Mol Cell. 2008 Oct. 24; 32(2):232-46). Disease arises when Kcnqlotl is aberrantly expressed. LNA molecules can be created to downregulate Kcnqlotl, thereby restoring expression of Kcnql. As another example, LNA molecules could inhibit caRNA binding to CTCF to reverse the imprinted defect.

From a commercial and clinical perspective, the timepoints between about 1 to 24 hours potentially define a window for epigenetic reprogramming. The advantage of the LNA system is that it works quickly, with a defined half-life, and is therefore reversible upon degradation of LNAs, at the same time that it provides a discrete timeframe during which epigenetic manipulations can be made. By targeting nuclear long ncRNAs, LNA molecules or similar polymers, e.g., xylo-LNAs, might be utilized to manipulate the chromatin state of cells in culture or in vivo, by transiently eliminating the regulatory RNA and associated proteins long enough to alter the underlying locus for therapeutic purposes. In particular, LNA molecules or similar polymers that specifically bind to, or are complementary to, CTCF binding sites can prevent recruitment of CTCF to a specific chromosomal locus, in a gene-specific fashion.

LNA molecules might also be administered in vivo to treat other human diseases, such as but not limited to cancer, neurological disorders, infections, inflammation, and myotonic dystrophy. For example, LNA molecules might be delivered to tumor cells to downregulate the biologic activity of a growth-promoting or oncogenic long nuclear ncRNA (e.g., Gt12 or MALAT1 (Luo et al., Hepatology. 44(4):1012-24 (2006)), a lncRNA associated with metastasis and is frequently unregulated in cancers). Repressive caRNAs downregulating tumor suppressors can also be targeted by LNA molecules to promote reexpression. For example, expression of the INK4b/ARF/INK4a tumor suppressor locus is controlled by Polycomb group proteins including PRC1 and PRC2 and repressed by the antisense noncoding RNA ANRIL (Yap et al., Mol Cell. 2010 Jun. 11; 38(5): 662-74). ANRIL can be targeted by LNA molecules to promote reexpression of the INK4b/ARF/INK4a tumor suppressor. Some CTCF binding sites may be associated with caRNAs that are positive regulators of oncogenes. Such "activating caRNAs" have been described recently (e.g., Jpx (Tian et al., Cell. 143(3):390-403 (2010) and others (Orom et al., Cell. 143(1):46-58 (2010)). Therefore, LNA molecules could be directed at these activating CTCF binding sites to downregulate oncogenes. LNA molecules could also be delivered to inflammatory cells to downregulate regulatory caRNA that modulate the inflammatory or immune response. (e.g., LincRNA-Cox2, see Guttman et al., Nature. 458(7235):223-7. Epub 2009 Feb. 1 (2009)).

In still other related aspects, the LNA molecules targeting CTCF binding sites described herein can be used to create animal or cell models of conditions associated with altered gene expression (e.g., as a result of altered epigenetics).

For example, it was first noticed about half a century ago that X chromosome changes are often seen in female reproductive cancers. Some 70% of breast carcinomas lack a 'Barr body', the cytologic hallmark of the inactive X chromosome (Xi), and instead harbor two or more active Xs (Xa). Additional X's are also a risk factor for men, as XXY men (Klinefelter Syndrome) have a 20- to 50-fold increased risk of breast cancer in a BRCA1 background.

The X is also known to harbor a number of oncogenes. Supernumerary Xa's correlate with a poor prognosis and stand as one of the most common cytogenetic abnormalities not only in reproductive cancers but also in leukemias, lymphomas, and germ cell tumors of both sexes. See, e.g., Liao et al., Cancer Invest 21, 641-58 (2003); Spatz et al., Nat Rev Cancer 4, 617-29 (2004); Barr et al., Proc Can Cancer Conf 2, 3-16 (1957); Borah et al., J Surg Oncol 13, 1-7 (1980); Camargo and Wang, Hum Genet 55, 81-5 (1980); Dutrillaux et al., Int J Cancer 38, 475-9 (1986); Ghosh and Shah, Cancer Genet Cytogenet 4, 269-74 (1981); Ghosh and Shah, Med Hypotheses 7, 1099-104 (1981); Ghosh et al., Acta Cytol 27, 202-3 (1983); Huang et al., Mol Cancer Ther 1, 769-76 (2002); Kawakami et al., Lancet 363, 40-2 (2004); Kawakami et al., J Urol 169, 1546-52 (2003); Kawakami et al., Oncogene 23, 6163-9 (2004); Moore and Barr, Br J Cancer 9, 246-52 (1955); Moore and Barr, Br J Cancer 11, 384-90 (1957); Moore et al., J Exp Zool 135, 101-25 (1957); Rosen et al., Ann Clin Lab Sci 7, 491-9 (1977); Sirchia et al., Cancer Res 65, 2139-46 (2005); Tavares, Lancet 268, 948-9 (1955); Tavares, Medico (Porto) 12, 97-100 (1961); Tavares, Acta Cytol 6, 90-4 (1962); Wang et al., Cancer Genet Cytogenet 46, 271-80 (1990); and Ganesan et al., Cold Spring Harb Symp Quant Biol 70, 93-7 (2005).

See also PCT/US11/60493, which is incorporated by reference herein in its entirety.

Antagomirs

In some embodiments, the inhibitory nucleic acid is an antagomir. Antagomirs are chemically modified antisense oligonucleotides that can target a CTCF binding site. For example, an antagomir for use in the methods described herein can include a nucleotide sequence sufficiently complementary to hybridize to a CTCF binding site target sequence of about 12 to 25 nucleotides, preferably about 15 to 23 nucleotides.

In some embodiments, antagomirs include a cholesterol moiety, e.g., at the 3'-end. In some embodiments, antagomirs have various modifications for RNase protection and pharmacologic properties such as enhanced tissue and cellular uptake. For example, in addition to the modifications discussed above for antisense oligos, an antagomir can have one or more of complete or partial 2'-O-methylation of sugar and/or a phosphorothioate backbone. Phosphorothioate modifications provide protection against RNase or other nuclease activity and their lipophilicity contributes to enhanced tissue uptake. In some embodiments, the antagomir cam include six phosphorothioate backbone modifications; two phosphorothioates are located at the 5'-end and four at the 3'-end, but other patterns of phosphorothioate modification are also commonly employed and effective. See, e.g., Krutzfeldt et al., Nature 438, 685-689 (2005); Czech, N Engl J Med 2006; 354:1194-1195 (2006); Robertson et al., Silence. 1:10 (2010); Marquez and McCaffrey, Hum Gene Ther. 19(1):27-38 (2008); van Rooij et al., Circ Res. 103(9):919-928 (2008); and Liu et al., Int. J. Mol. Sci. 9:978-999 (2008). Krutzfeld et al. (2005) describe chemically engineered oligonucleotides, termed 'antagomirs', that are reported to be efficient and specific silencers of endogenous miRNAs in mice.

In general, the design of an antagomir avoids target RNA degradation due to the modified sugars present in the molecule. The presence of an unbroken string of unmodified sugars supports RNAseH recruitment and enzymatic activity. Thus, typically the design of an antagomir will include bases that contain modified sugar (e.g., LNA), at the ends or interspersed with natural ribose or deoxyribose nucleobases.

Antagomirs useful in the present methods can also be modified with respect to their length or otherwise the number of nucleotides making up the antagomir. In some embodiments, the antagomirs must retain specificity for their target, i.e., must not directly bind to, or directly significantly affect expression levels of, transcripts other than the intended target.

In some embodiments, antagomirs may exhibit nonspecific binding that does not produce significant undesired biologic effect, e.g., the antagomirs do not affect expression levels of non-target transcripts or their association with regulatory proteins or regulatory RNAs.

Interfering RNA, Including siRNA/shRNA

In some embodiments, the inhibitory nucleic acid sequence that is complementary to a CTCF binding site can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof.

Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc NatlAcadSci USA 99:6047-6052, (2002).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

In general the siRNAs must retain specificity for their target, i.e., must not directly bind to, or directly significantly affect expression levels of, transcripts other than the intended target.

Ribozymes

In some embodiments, the inhibitory nucleic acids are ribozymes. Trans-cleaving enzymatic nucleic acid molecules can also be used; they have shown promise as therapeutic agents for human disease (Usman & McSwiggen, 1995 Ann. Rep. Med. Chem. 30, 285-294; Christoffersen and Marr, 1995 J. Med. Chem. 38, 2023-2037). Enzymatic nucleic acid molecules can be designed to cleave specific caRNA targets within the background of cellular RNA. Such a cleavage event renders the caRNA non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, Proc. R. Soc. London, B 205, 435) have been used to evolve new nucleic acid catalysts capable of catalyzing a variety of reactions, such as cleavage and ligation of phosphodiester linkages and amide linkages, (Joyce, 1989, Gene, 82, 83-87; Beaudry et al., 1992, Science 257, 635-641; Joyce, 1992, Scientific American 267, 90-97; Breaker et al, 1994, TIBTECH 12, 268; Bartel et al, 1993, Science 261:1411-1418; Szostak, 1993, TIBS 17, 89-93; Kumar et al, 1995, FASEB J., 9, 1183; Breaker, 1996, Curr. Op. Biotech., 1, 442). The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min$^{-1}$ in the presence of saturating (10 MM) concentrations of Mg$^{2+}$ cofactor. An artificial "RNA ligase" ribozyme has been shown to catalyze the corresponding self-modification reaction with a rate of about 100 min$^{-1}$. In addition, it is known that certain modified hammerhead ribozymes that have substrate binding arms made of DNA catalyze RNA cleavage with multiple turn-over rates that approach 100 min$^{-1}$.

Making and Using Inhibitory Nucleic Acids

The nucleic acid sequences used to practice the methods described herein, whether RNA, cDNA, genomic DNA, vectors, viruses or hybrids thereof, can be isolated from a variety of sources, genetically engineered, amplified, and/or expressed/generated recombinantly. If desired, nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and "RNA Viruses: A Practical Approach" (Alan J. Cann, Ed., Oxford University Press, (2000)).

Preferably, inhibitory nucleic acids of the invention are synthesized chemically. Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066; WO/2008/043753 and WO/2008/049085, and the refences cited therein.

Nucleic acid sequences of the invention can be stabilized against nucleolytic degradation such as by the incorporation of a modification, e.g., a nucleotide modification. For example, nucleic acid sequences of the invention includes a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O-N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom (see, e.g., Kaupinnen et al., Drug Disc. Today 2(3):287-290 (2005); Koshkin et al., J. Am. Chem. Soc., 120(50):13252-13253 (1998)). For additional modifications see US 20100004320, US 20090298916, and US 20090143326.

It is understood that any of the modified chemistries or formats of inhibitory nucleic acids described herein can be combined with each other, and that one, two, three, four, five, or more different types of modifications can be included within the same molecule.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Modification Patterns

In some embodiments, the inhibitory oligonucleotide comprises locked nucleic acids (LNA), ENA modified nucleotides, 2'-O-methyl nucleotides, or 2'-fluoro-deoxyribonucleotides. In some embodiments, the inhibitory oligonucleotide comprises alternating deoxyribonucleotides and 2'-fluoro-deoxyribonucleotides. In some embodiments, the inhibitory oligonucleotide comprises alternating deoxyribonucleotides and 2'-O-methyl nucleotides. In some embodiments, the inhibitory oligonucleotide comprises alternating deoxyribonucleotides and ENA modified nucleotides. In some embodiments, the inhibitory oligonucleotide comprises alternating deoxyribonucleotides and locked nucleic acid nucleotides. In some embodiments, the inhibitory oligonucleotide comprises alternating locked nucleic acid nucleotides and 2'-O-methyl nucleotides.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the inhibitory oligonucleotide comprises phosphorothioate internucleotide linkages. In some embodiments, the single stranded oligonucleotide comprises phosphorothioate internucleotide linkages between at least two nucleotides. In some embodiments, the single stranded oligonucleotide comprises phosphorothioate internucleotide linkages between all nucleotides.

It should be appreciated that the oligonucleotide can have any combination of modifications as described herein.

As an example, the oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)XxxxXX, (X)xXxXXx, (X)xXxxXX, (X)xxXxXX, (X)xXxXxX and (X)XxXxXx, (d) (X)xxXXXX, (X)xXxXXX, (X)xXXxXX, (X)xXXXxX, (X)xXXXXx, (X)XxxXXX, (X)XxXxXX, (X)XxXXxX, (X)XxXXx, (X)XXxxXX, (X)XXxXxX, (X)XXXxxX, (X)XXxXXx, (X)XXXxXx, (X)XXXXxx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

In some embodiments, the oligonucleotide is a gapmer (contain a central stretch (gap) of DNA monomers sufficiently long to induce RNase H cleavage, flanked by blocks of LNA modified nucleotides; see, e.g., Stanton et al., Nucleic Acid Ther. 2012. 22: 344-359; Nowotny et al., Cell, 121:1005-1016, 2005; Kurreck, European Journal of Biochemistry 270: 1628-1644, 2003; FLuiter et al., Mol Biosyst. 5(8):838-43, 2009). In some embodiments, the oligonucleotide is a mixmer (includes alternating short stretches of LNA and DNA; Naguibneva et al., Biomed Pharmacother. 2006 November; 60(9):633-8; from et al., Gene. 2006 May 10; 3720:137-41).

Additional Sequence Structural Information

The inhibitory oligonucleotides described herein may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The inhibitory oligonucleotides have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than the gene of interest. The oligonucleotide is expected to have a reduced likelihood of having off-target effects. The threshold level of sequence identity may be 50%, 60%, 70%, 80%, 85%, 90%, 95%, 99% or 100% sequence identity.

The inhibitory oligonucleotides may have a sequence that is complementary to a region that encodes an RNA that forms a secondary structure comprising at least two single stranded loops. In some embodiments, oligonucleotides that are complementary to a region that encodes an RNA that forms a secondary structure comprising one or more single stranded loops (e.g., at least two single stranded loops) have a greater likelihood of being active (e.g., of being capable of activating or enhancing expression of a target gene) than a randomly selected oligonucleotide. In some cases, the secondary structure may comprise a double stranded stem between the at least two single stranded loops. Accordingly, the area of complementarity between the oligonucleotide and the nucleic acid region may be at a location of the PRC2 associated region that encodes at least a portion of at least one of the loops. In some embodiments, the predicted secondary structure RNA (e.g., of the CTCF binding site) containing the nucleic acid region is determined using RNA secondary structure prediction algorithms, e.g., RNAfold, mfold. In some embodiments, oligonucleotides are designed to target a region of the RNA that forms a secondary structure comprising one or more single stranded loop (e.g., at least two single stranded loops) structures which may comprise a double stranded stem between the at least two single stranded loops.

The inhibitory oligonucleotide may have a sequence that is has greater than 30% G-C content, greater than 40% G-C content, greater than 50% G-C content, greater than 60% G-C content, greater than 70% G-C content, or greater than 80% G-C content. The inhibitory oligonucleotide may have a sequence that has up to 100% G-C content, up to 95% G-C content, up to 90% G-C content, or up to 80% G-C content.

The inhibitory oligonucleotide may be complementary to a chromosome of a different species (e.g., a mouse, rat, rabbit, goat, monkey, etc.) at a position that encompasses or that is in proximity to that species' homolog of the gene of interest. The inhibitory oligonucleotide may be complementary to a human genomic region encompassing or in proximity to the target gene and also be complementary to a mouse genomic region encompassing or in proximity to the mouse homolog of the target gene. Oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the region of complementarity of the inhibitory oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a CTCF binding site disclosed in the tables provided herein. In some embodiments, the region of complementarity is complementary with at least 8, 10, 12, 14, 16, 18, or 20 consecutive nucleotides of a CTCF binding site disclosed in the tables provided herein.

Modulating CTCF Binding to Genomic DNA

As described herein, CTCF localizes/binds to genomic DNA in a sequence-specific manner; the present methods can include inhibiting this localization, in addition to or as an alternative to administering an inhibitory nucleic acid as described herein that binds a CTCF-binding RNA. To inhibit this localization, and thus disrupt CTCF-dependent repression and increase expression of nearby genes, oligonucleotides are used that bind to genomic DNA at or near (e.g., within 100, 50, or 25) nucleotides of a CTCF localization site identified in Tables 1 and 2. Table 1 lists genes corresponding to the CTCF CLIP-seq peaks from human embryonic kidney cells, and Table 2 provides the Human genomic regions determined by LiftOver analysis to correspond to the CTCF CLIP-seq peaks from Mus musculus mouse embryonic fibroblasts. Each table provides the SEQ ID NO: of the peak(s) (i.e., the CTCF localization site(s)) that correspond to each of the listed genes.

In some embodiments, the oligonucleotides are triplex-forming oligonucleotides (TFOs). TFOs are defined as triplex-forming oligonucleotides which bind as third strands to duplex DNA in a sequence specific manner. Triplex-forming oligonucleotides may be comprised of any possible combination of nucleotides and modified nucleotides. Modified nucleotides may contain chemical modifications of the heterocyclic base, sugar moiety or phosphate moiety. TFOs, and methods of making them, are known in the art; see, e.g., Frank-Kamenetskii and Mirkin, Annual Review of Biochemistry, 64:65-95 (1995); Vasquez and Glazer, Quarterly Reviews of Biophysics, 35(01):89-107 (2002); US PGPub Nos. 20070219122; US20110130557; and US20090216003.

In general, the TFO is a single-stranded nucleic acid molecule between 5 and 100 nucleotides in length, preferably between 7 and 40 nucleotides in length, e.g., 10 to 20 or 20 to 30 nucleotides in length. In some embodiments, the base composition is homopurine or homopyrimidine, polypurine or polypyrimidine. The oligonucleotides can be generated using known DNA synthesis procedures.

The nucleotide sequence of the oligonucleotides is selected based on a target sequence of a CTCF localization sequence as provided herein; in addition, the sequence can be determined based on physical constraints imposed by the need to achieve binding of the oligonucleotide within the major groove of the target region, and preferably have a low dissociation constant (Kd) for the oligonucleotide/target sequence. The oligonucleotides should have a base composition that is conducive to triple-helix formation and can be generated based on known structural motifs for third strand binding. The most stable complexes are formed on polypurine:polypyrimidine elements, which are relatively abundant in mammalian genomes. Triplex formation by TFOs can occur with the third strand oriented either parallel or anti-parallel to the purine strand of the duplex. In the anti-parallel, purine motif, the triplets are G.G:C and A.A:T, whereas in the parallel pyrimidine motif, the canonical triplets are $C^+$.G:C and T.A:T. The triplex structures are stabilized by two Hoogsteen hydrogen bonds between the bases in the TFO strand and the purine strand in the duplex. See U.S. Pat. No. 5,422,251 for additional information on base compositions for third strand binding oligonucleotides.

The TFOs can include one or more modifications, e.g., backbone modifications such as incorporation of the flexible basestacking monomers (Bulge insertions of (R)-1-O-[4-(1-pyrenylethynyl)phenylmethyl]glycerol into the middle of homopyrimidine oligodeoxynucleotides (twisted intercalating nucleic acids, TINA)) as described in US PGPub No 20090216003; intercalating nucleic acid monomers as described in WO2006125447A2; intercalator (R)-1-O-[4-(1-pyrenylethynyl)benzyl]-glycerol (see, e.g., Filichev et al., J. Am. Chem. Soc. 127:14849 (2005); Filichev et al., Eur. J. Org. Chem. 17:3960-3968 (2006); Globisch et al., Hely. Chim. Acta, 91:805 (2008)); 2-phenyl or 2-naphth-1-yl-phenanthroimidazole intercalators as described in US20110130557.

In addition or in alternative, modifications can be made to the nucleobases (see, e.g., Roig and Asseline, J. Am. Chem. Soc. 2003, 125, 4416; Hildbrand et al., J. Am. Chem. Soc. 1997, 119, 5499; and Xodo et al., Nucleic Acids Res. 1991, 19, 5625); to the sugar (sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O-(N-(methyl)acetamido) (2'-OMA). 2'-O-aminoethyl sugar moiety substitutions are especially preferred; see, e.g., Carlomagno et al., J. Am. Chem. Soc. 2001, 123, 7364; Cuenoud et al., Angew. Chem. Int. Ed. 1998, 37, 1288; Wengel, Acc. Chem. Res. 1999, 32, 301; Obika et al., Tetrahedron Let. 2000, 41, 8923; Sun et al., Biochemistry, 2004, 43, 4160; Basye et al., Nucleic Acids Res. 2001, 29, 4873); and/or to the phosphate backbone (see, e.g., Michel, et al., Chem Bio Chem. 2005, 6, 1254; Ehrenmann et al., Nucl. Nucl. Nucleic Acids. 2001, 20, 797; Michel et al., J. Biomol. Struct. Dyn. 2003, 21, 435; Tereshko et al., J. Am. Chem. Soc. 1998, 120, 269; Escude et al., Proc. Natl. Acad. Sci. U.S.A. 1996, 93, 4365; Gryaznov et al., Proc. Natl. Acad. Sci. U.S.A. 1995, 92, 5798; Gryaznov and Chen, J. Am. Chem. Soc. 1994, 116, 3143; and Chur et al., Nucleic Acids Res. 1993, 21, 5179). Chemical modifications of heterocyclic bases or heterocyclic base analogs can be used to increase the binding affinity of a nucleotide or its stability in a triplex. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-beta-D-ribofuranosyl)pyridine (2-aminopyridine), and various pyrrolo- and pyrazolopyrimidine derivatives. Substitution of 5-methylcytosine or pseudoisocytosine for cytosine in triplex-forming molecules such as TFOs and PNAs helps to stabilize triplex formation at neutral and/or physiological pH, especially in triplex-forming molecules with isolated cytosines. See, e.g., US20110268810.

For example, each nucleotide monomer can be selected from the group consisting of DNA, RNA, HNA, MNA, ANA, LNA, CAN, INA, CeNA, TNA, (2'-NH)-TNA, (3'-

NH)-TNA, alpha-L-Ribo-LNA, alpha-L-Xylo-LNA, beta-D-Ribo-LNA, beta-D-Xylo-LNA, [3.2.1]-LNA, Bicyclo-DNA, 6-Amino-Bicyclo-DNA, 5-epi-Bicyclo-DNA, alpha-Bicyclo-DNA, Tricyclo-DNA, Bicyclo[4.3.0]-DNA, Bicyclo[3.2.1]-DNA, Bicyclo[4.3.0]amide-DNA, beta-D-Ribopyranosyl-NA, alpha-L-Lyxopyranosyl-NA, 2'-R-RNA, 2'-OR-RNA, 2'-AE-RNA, alpha-L-RNA, and beta-D-RNA, and combinations and modifications thereof; in some embodiments, some or all of the TFO is a peptide nucleic acid (PNA), in which the phosphate backbone of oligonucleotides is replaced in part or in its entirety by repeating N-(2-aminoethyl)-glycine units, and the phosphodiester bonds are replaced by peptide bonds. In addition, the TFO can include one or more of the modifications described in WO2012/065143.

In some embodiments, the TFO includes a "tail" or "tail clamp" added to the Watson-Crick binding portion that binds to target strand outside the triple helix and reduces the requirement for a polypurine:polypyrimidine stretch, increasing the number of potential target sites. Tail clamps added to PNAs (referred to as tcPNAs) have been described by Kaihatsu, et al., Biochemistry, 42(47):13996-4003 (2003); Bentin, et al., Biochemistry, 42(47):13987-95 (2003) Rogers, et al., Proc. Natl. Acad. Sci. USA., 99(26): 16695-700 (2002)), and are known to bind to DNA more efficiently due to low dissociation constants.

The addition of the tail also increases binding specificity and binding stringency of the triplex-forming molecules to the target duplex.

In some embodiments, the TFOs are modified with, or administered with, amidoanthraquinones as described in Fox et al., Proc. Natl. Acad. Sci. USA 92:7887-7891 (1995).

Methods of Treatment Using TFOs

TFOs that target CTCF binding sites associated with disease-related genes can also be used to treat subjects. For example, the DMD gene is a causal factor in Duchenne muscular dystrophy; administration of a TFO that targets a CTCF localization site associated with the XIST gene can be used to treat subjects who have Rett Syndrome. One of skill in the art would be able to identify other disease-related genes from among those listed in Tables 1 and 2. In particular, a TFO that targets a CTCF localization site associated with a human disease-related gene as set forth in Tables 1 or 2 (and/or Table A) can be used to treat a human having the disease to which the gene is related; in some embodiments, the TFOs are used to reactivate a normal gene in a heterozygous individual, i.e., an individual with one normal copy and one affected copy of the gene. The TFO can be administered in a pharmaceutical composition or formulation as known in the art, e.g., as described herein. Subjects having a genetic disease, e.g., a disease related to a gene listed in Table 1 or 2, can be identified using methods known in the art.

Pharmaceutical Compositions

The methods described herein can include the administration of pharmaceutical compositions and formulations comprising inhibitory nucleic acid sequences designed to target a CTCF binding site.

In some embodiments, the compositions are formulated with a pharmaceutically acceptable carrier. The pharmaceutical compositions and formulations can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration of pharmaceuticals are well described in the scientific and patent literature, see, e.g., Remington: The Science and Practice of Pharmacy, 21st ed., 2005. The inhibitory nucleic acids can be administered alone or as a component of a pharmaceutical formulation (composition). The compounds may be formulated for administration, in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions of the invention include those suitable for intradermal, inhalation, oral/nasal, topical, parenteral, rectal, and/or intravaginal administration. The formulations may conveniently be presented in unit dosage form and may be prepared by any methods well known in the art of pharmacy. The amount of active ingredient (e.g., nucleic acid sequences of this invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g., an antigen specific T cell or humoral response.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., nucleic acid sequences of the invention) in admixture with excipients suitable for the manufacture of aqueous suspensions, e.g., for aqueous intradermal injections. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

In some embodiments, oil-based pharmaceuticals are used for administration of nucleic acid sequences of the invention. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102.

Pharmaceutical formulations can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent. In alternative embodiments, these injectable oil-in-water emulsions of the invention comprise a paraffin oil, a sorbitan monooleate, an ethoxylated sorbitan monooleate and/or an ethoxylated sorbitan trioleate.

The pharmaceutical compounds can also be administered by in intranasal, intraocular and intravaginal routes including suppositories, insufflation, powders and aerosol formulations (for examples of steroid inhalants, see e.g., Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In some embodiments, the pharmaceutical compounds can be delivered transdermally, by a topical route, formulated as applicator sticks, solutions, suspensions, emulsions, gels, creams, ointments, pastes, jellies, paints, powders, and aerosols.

In some embodiments, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In some embodiments, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

In some embodiments, the pharmaceutical compounds and formulations can be lyophilized. Stable lyophilized formulations comprising an inhibitory nucleic acid can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. 20040028670.

The compositions and formulations can be delivered by the use of liposomes. By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. As used in the present invention, the term "liposome" means a vesicle composed of amphiphilic lipids arranged in a bilayer or bilayers. Liposomes are unilamellar or multilamellar vesicles that have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes can also include "sterically stabilized" liposomes, i.e., liposomes comprising one or more specialized lipids. When incorporated into liposomes, these specialized lipids result in liposomes with enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The formulations of the invention can be administered for prophylactic and/or therapeutic treatments. In some embodiments, for therapeutic applications, compositions are administered to a subject who is at risk of or has a disorder described herein, in an amount sufficient to cure, alleviate or partially arrest the clinical manifestations of the disorder or its complications; this can be called a therapeutically effective amount.

The amount of pharmaceutical composition adequate to accomplish this is a therapeutically effective dose. The dosage schedule and amounts effective for this use, i.e., the dosing regimen, will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; Remington: The Science and Practice of Pharmacy, 21st ed., 2005). The state of the art allows the clinician to determine the dosage regimen for each individual patient, active agent and disease or condition treated.

Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on for example: the dosage and frequency as required and tolerated by the patient, the degree and amount of therapeutic effect generated after each administration (e.g., effect on tumor size or growth), and the like. The formulations should provide a sufficient quantity of active agent to effectively treat, prevent or ameliorate conditions, diseases or symptoms.

In alternative embodiments, pharmaceutical formulations for oral administration are in a daily amount of between about 1 to 100 or more mg per kilogram of body weight per day. Lower dosages can be used, in contrast to administration orally, into the blood stream, into a body cavity or into a lumen of an organ. Substantially higher dosages can be used in topical or oral administration or administering by powders, spray or inhalation.

In some embodiments, the methods described herein can include co-administration with other drugs or pharmaceuticals, e.g., compositions for providing cholesterol homeostasis. For example, the inhibitory nucleic acids can be co-administered with drugs for treating or reducing risk of a disorder described herein.

EXAMPLES

The invention is further described in the following examples, which do not limit the scope of the invention described in the claims.

Methods

The following methods were used in the examples set forth below.

UV-Crosslinking and Immunoprecipitation of RNA

A modified CLIP protocol based on previously published protocols (Ule et al., 2003; Ule et al., 2005; Jensen and R. B., 2008; Licatalosi et al., 2008; Yeo et al., 2009) was used in this study. $10^8$ mouse ES cells expressing the FLAG-tagged CTCF protein (Sun et al., 2013) were trypsinized and resuspended in PBS. Cells for +UV experiments were cross-linked with 256 nm UV in a 15-cm dish at 250 mJ/cm$^2$ using the Stratalinker 1800 (Stratagene). ±UV cell pellets were resuspended in 1-2 mL Buffer A (10 mM HEPES pH 7.9, 1.5 mM MgCl$_2$, 10 mM KCl, 0.5 mM PMSF) and incubated on ice for 30 min with frequent vortexing. Nuclei were pelleted at 2500×g for 15 min, washed in PBS, resuspended in 500 mL Buffer C (20 mM HEPES pH 7.5, 420 mM NaCl, 15% glycerol, 1.5 mM MgCl$_2$, 0.5 mM PMSF, protease and RNase inhibitors) and incubated at 4° C. for 30 min with rotation. Nuclear lysates were diluted with one volume of 20 mM HEPES pH 7.5 and treated with 40 U TURBO DNase at 37° C. for 30 min to liberate chromatin-associated CTCF-RNA complexes. After quenching the DNase with 10 mM EDTA, 5% was removed and saved for RNA-seq, while the remainder was added with sarkosyl to 0.5% and the RNA was fragmented by sonication with Diagenode Bioruptor XL twice for 20 min each (with 30 s on, 30 s off cycles). Cell debris was pelleted at 16,000×g for 10 min, the lysate was diluted again with 1 volume of 20 mM HEPES and divided into three aliquots. 15 uL of Anti-FLAG M2 Magnetic Beads (Sigma-Aldrich A2220) was added to each aliquot and incubated at 4° C. overnight with rotation. Beads from all aliquots were recombined, washed 3× with high salt Wash Buffer I (20 mM HEPES pH 7.5, 250 mM NaCl, 0.1% SDS, 0.5% sodium deoxycholate, 0.5% Nonident-P40, protease and RNase inhibitors), once with 1× TURBO DNase buffer, then treated with 100 U/mLTURBO DNase at 37° C. for 30 min. Beads were further washed 2× with Wash Buffer I supplemented with 10 mM EDTA, then 2× with low salt Wash Buffer II (50 mM Tris-HCl pH 7.5, 1% NP40, 0.5% sodium deoxycholate, 50 mM NaCl, 10 mM EDTA), and 1× with PNK buffer (50 mM Tris-HCl pH 7.5, 10 mM $MgCl_2$, 0.5% NP40, 5 mM DTT). CLIP-tags on beads were radio-labelled with [$\gamma$-$^{32}$P]ATP using T4 polynucleotide kinase (New England Biolabs) for 20 min at 37° C., and washed 4× with PNK buffer. Beads were resuspended in SDS-PAGE loading buffer at heated for 5 min at 70° C., run on 8% Bis-Tris SDS-PAGE in MOPS buffer (50 mM MOPS, 50 mM Tris, 0.1% SDS, 1 mM EDTA) at 120 V, transferred to nitrocellulose membrane, and exposed to film for autoradiography or used for immunoblot with 1:3000 αFLAG antibodies (Sigma-Aldrich F1804).

Membrane fragments containing CLIP signal, as confirmed by immunoblot, and corresponding positions on control lanes were excised, and RNA was eluted by incubation in prewarmed proteinase K buffer (100 mM Tris-HCl pH 7.5, 50 mM NaCl, 10 mM EDTA, 0.5% SDS, 4 mg/mL proteinase K) for 20 min at 37° C., then incubation for an additional 20 min in proteinase K buffer supplemented with 7 M urea, followed by TRIzol extraction and ethanol precipitation. RNA size and quality was verified using RNA 6000 Pico chips on the Agilent Bioanalyzer.

CLIP-seq library was constructed from CLIP RNA using the NEBNext Small RNA Library Prep set (New England Biolabs E7330), size-selected and cleaned up of primer/adaptor-dimers using Agencourt AMPure XP beads (Beckman Coulter A63880), verified with DNA High Sensitivity chips on the Agilent Bioanalyzer, quantitated using KAPA Biosystems library quantification kit (KK4844), and sequenced with the Illumina HiSeq 2000 system with 50 cycles paired end reads.

RNA-Seq

Nuclear lysate was removed before sonication, and treated with proteinase K and reprecipitated in the same way as CLIP RNA eluted from membrane. RNA was depleted of ribosomal RNA with RiboMinus Eukaryote System (Ambion A15026), treated with TURBO DNase, and cleaned up with RNeasy MinElute columns (Qiagen 74204). RNA was fragmented in Superscript III first strand synthesis buffer for 10 min at 94° C. before being used for first strand cDNA synthesis with the addition of 27.5 ng/μL actinomycin D. Second strand cDNA synthesis was performed with NEBNext mRNA Second Strand Synthesis Module (E6111) in the presence of 1.25 mM dUTP to preserve directionality. Double-stranded cDNA was then used to generate RNA-seq libraries using the NEBNext ChIP-Seq Library Prep Master Mix Set (E6240), and quality-checked and sequenced similarly as the CLIP-seq libraries.

ChIP-Seq

ChIP was performed essentially as described (Jeon and Lee, 2011) using 1.5×10$^7$ TST mouse ES cells (Ogawa and Lee, 2003) and aCTCF antibodies (Cell Signaling 2899). After nuclear lysis, chromatin was sonicated in Covaris S2 ultrasonicator with 5% duty cycle, intensity 6, 200 bursts per 1-min cycle for 8 min, before IP. 15 ng of input or purified ChIP DNA was used for ChIP-seq library construction using the NEBNext ChIP-Seq Library Prep Master Mix Set. Libraries were quality-checked and sequenced similarly as CLIP-seq libraries.

Bioinformatic Analyses

Adaptor sequences were trimmed from libraries with either Trim Galore! v0.3.3 (http://www.bioinformatics.babraham.ac.uk/projects/trim_galore/) (for CLIP-seq and RNA-seq; stringency 15 and allowed error rate 0.2) or Cutadapt v1.0 (Martin, 2011)((for ChIP-seq; allowed error rate 0.2). Identical sequences were removed by custom programs prior to alignment. To account for the *M. mus* (*mus*) *M. castaneus* (*cas*) hybrid character of the ES cell lines, reads were first aligned to custom mus/129 and cas genomes, and then mapped back to the reference mm9 genome (Pinter et al., 2012). RNA was aligned with Tophat (v2.0.8 or greater) (Kim et al., 2013), while DNA was aligned using Novoalign (3.00.03) (www.novocraft.com). Post-processing of mm9 alignments was performed with custom scripts, SAMtools v0.1.18 (Li et al., 2009), and BEDtools v2.17.0 (Quinlan and Hall, 2010). These included accounting, alignment file-type conversion, extracting and sorting uniquely/paired-end reads (SAMtools), and obtaining wig coverage files (DNA: BEDtools genomecov; RNA: SAMtools depth).

For repeats analysis, non-uniquely aligned fragments were put into a "reps" category. mm9 RepeatMasker tracks from UCSC were obtained using the table browser. The first of each non-uniquely aligned fragment was then extracted and intersected with each family of repeat elements using BEDtools intersect with options -s, -c, and the percentage that mapped to each family was counted.

For CLIP-seq, +UV and −UV libraries were scaled according to total number of fragments in each library (determined by SAMtools flagstat combining reads "with itself and mate mapped" and "singletons"). After subtracting −UV hits from +UV single nucleotide hit counts, peaks of CTCF enrichment were called using Piranha v1.2.0 (Uren et al., 2012) based on a zero-truncated Poisson distribution and a p-value cutoff of 0.01. Peaks were categorized into sense, antisense-only and intergenic classes. The sense category was derived by strand-specifically intersecting peaks with 3000-nt enveloped gene bodies. The antisense-only category was derived similarly using an antisense intersection and subtracting out sense genes, while the intergenic category was the result of the complement of intersecting peaks non-strand-specifically with gene bodies.

To assemble RNA transcripts from RNA-seq data, Cufflinks (v2.1.1) (Trapnell et al., 2012) was used on composite d0 and d3 alignments with upper-quartiles-norm normalization, and guided (-g) with mm9 Ensembl transcripts. The resulting transcripts were purged of entries with FPKM=0, converted to bed format, and merged using BEDtools merge with options -nms, -scores mean, -s. To compare CLIP-seq and RNA-seq, CLIP peaks were mapped onto the transcripts using BEDtools map with options -o sum, -s, and FPKM values were obtained by dividing the summed coverage by transcript length/1000. Scatterplots were generated using Excel.

For display purposes, ChIP-seq coverage of uniquely aligned neutral/cas/mus (comp) reads were obtained and normalized to input libraries using in-house software (smoothing parameters: window size 125 and step size 25). ChIP binding positions were identified by intersecting the results of the mirror tag correlation (MTC) and window tag density (WTD) peak-finding methods within the SPP program (Kharchenko et al., 2008). Briefly, both IP and input data had local anomalies removed, then binding positions were identified using the find binding.positions routine (FDR=0.01; default method for WDT, and tag.lwcc for MTC, whs=detection.window.halfsize). Peak regions were extended using the add.broadpeak.regions function (window. size=10$^2$, z.thr=3). Finally these results were intersected to give a final high confidence peak list.

ChIP-seq allelic peak calling was performed to identify an SPP-called region as being on the active (cas) or inactive (mus) chromosome. Under the null hypothesis it was equally likely that a ChIP region would be identified by tags of either cas or mus and thus was treated as if following a binomial distribution (Pinter et al., 2012). p-values associated with cas or mus tag-id counts under an SPP-determined peak were determined from the q-value of the cumulative binomial distribution (p=0.5).

Cis-regulatory Element Annotation System (Shin et al., 2009) was used to determine peak enrichment in genomic regions and to obtain metagene profiles and metasite analyses (including comparison of CLIP peaks to ChIP enrichment). CEAS parameters were span=5000; sizes=1000, 3000,5000; and rel-dist=5000. Metagene profiles were obtained on .wig files generated from the peaks .bed files using a custom perl script. The CEAS-associated program sitepro was used to generate metasite profiles.

Recombinant Protein Cloning and Purification

Mus musculus CTCF cDNA with additional sequence encoding for a C-terminal 6×His tag was cloned into pFLAG-2 (Sigma) using EcoRI and XhoI to generate pBD39. GFP cDNA (pFA6a-GFP(S65T)-kanMX6) was similarly cloned with a C-terminal 6×His tag into pFLAG-2 to generate pBD40. Recombinant FLAG-CTCF-6×His and FLAG-GFP-6×His proteins were purified from Rosetta-Gami B cells (Novagen). Briefly, pBD39 and pBD40 transformed cells were induced with 0.2 mM IPTG at 18° C. (CTCF) or 1 mM IPTG (GFP) at 30° C. FLAG-GFP-6×His expressing cells were lysed at 4° C. with 50 mM sodium phosphate pH 8, 300 mM NaCl, 20 mM imidazole, 0.5% Triton X-100, and protease inhibitors. Following sonication, insoluble material was separated by centrifugation. FLAG-GFP-6×His was purified from the supernatant using Ni-NTA resin (Qiagen). FLAG-CTCF-6×His expressing cells were lysed at 4° C. with 50 mM sodium phosphate pH 8, 300 mM NaCl, 20 mM imidazole, 0.5% Sarkosyl, and protease inhibitors. Triton X-100 was then added to 2% final (v/v). Debris was removed by centrifugation. FLAG-CTCF-6×His was purified from the supernatant using Ni-NTA resin. Both proteins were eluted from Ni-NTA resin with 50 mM sodium phosphate pH 8, 300 mM NaCl, and 250 mM imidazole. Eluates were dialyzed against 10 mM Tris-HCl pH 7.5, 2.5 mM MgCl$_2$, 50 mM KCl, 0.1 mM ZnSO$_4$, mM DTT, 0.1% Tween-20, and 10% glycerol.

GST-fusion proteins of CTCF fragments were previously described (Donohoe et al., 2007).

In Vitro RNA Pulldown Assay

In vitro pulldown was performed as previously reported (Jeon and Lee, 2011). 1.5 µg of purified FLAG-tagged CTCF proteins or equimolar amounts of FLAG-tagged GFP (or no protein, in the case of mock pulldown) was immobilized on 30 µL of Anti-FLAG M2 Magnetic Beads in 400 µL PBS with 1 mM DTT at 4° C. for 2 hr. 15 µg of total RNA from day 3 female ES cells, treated with TURBO DNase and renatured by heating for 10 min 60° C. followed by slow cooling to 4° C., was then incubated with the protein-beads complexes at room temperature for 1 hr in 400 µL of Binding Buffer (1×PBS, 2 mM MgCl$_2$, 0.2 mM ZnCl$_2$, 0.2% NP40, 1 mM DTT, 100 U/ml RNase Inhibitor, 0.1 mg/ml yeast tRNA [Invitrogen], 0.5 mg/mL bovine serum albumin), with 10% of RNA-buffer mixture saved as input. Beads were washed 5× with Wash Buffer (1×PBS supplemented with additional 450 mM NaCl, to a total of 600 mM). RNA was isolated by TRIzol extraction and used in strand-specific qRT-PCR with the following primers:

RepA F:
(SEQ ID NO: 139661)
5'-CGGTTCTTCCGTGGTTTCTC-3'

RepA R:
(SEQ ID NO: 139662)
5'-GGTAAGTCCACCATACACAC-3'

RepF F:
(SEQ ID NO: 139663)
5'-CTCGACAGCCCAATCTTTGTT-3'

RepF R:
(SEQ ID NO: 139664)
5'-ACCAACACTTCCACTTAGCC-3'

RepC F:
(SEQ ID NO: 139665)
5'-ACTTTGCATACAGTCCTACTTTACTT-3'

RepC R:
(SEQ ID NO: 139666)
5'-GGAAAGGAGACTTGAGAGATGATAC-3'

Tsix F:
(SEQ ID NO: 139667)
5'-AATGCTTGCCAGCTATGCGG-3'

Tsix R:
(SEQ ID NO: 139668)
5'-TAACCACCTGTAAGGGACAG-3'

Jpx F:
(SEQ ID NO: 139669)
5'-TTAGCCAGGCAGCTAGAGGA-3'

Jpx R:
(SEQ ID NO: 139670)
5'-AGCCGTATTCCTCCATGGTT-3'

Ppia F:
(SEQ ID NO: 139671)
5'-CGATGACGAGCCCTTGG-3'

Ppia R:
(SEQ ID NO: 139672)
5'-TCTGCTGTCTTTGGAACTTTGTC-3'

H19 F:
(SEQ ID NO: 139673)
5'-TGTAAACCTCTTTGGCAATGCTGCC-3'

H19 R:
(SEQ ID NO: 139674)
5'-TATTGATGGACCCAGGACCTCTGGT-3'

Gtl2 F:
(SEQ ID NO: 139675)
5'-CGAGGACTTCACGCACAAC-3'

Gtl2 R:
(SEQ ID NO: 139676)
5'-TTACAGTTGGAGGGTCCTGG-3'

Gtl2-as F:
(SEQ ID NO: 139677)
5'-CACCCTGAACATCCAACA-3'

Gtl2-as R:
(SEQ ID NO: 139678)
5'-CATCTGCTTTTCCTACCTGG-3'

Malat1 F:
(SEQ ID NO: 139679)
5'-TAAGCGCTTGCCTCTGTCTT-3'

Malat1 R:
(SEQ ID NO: 139680)
5'-CACCTGCATTCTGTGTGGTC-3'

Neat1 F:
(SEQ ID NO: 139681)
5'-TGAGTGCTTTGCCACTGAAT-3'

Neat1 R:
(SEQ ID NO: 139682)
5'-TAACAGCTTCCCCTCTGCTC-3'

Airn F:
(SEQ ID NO: 139683)
5'-TAGTGTCCCGAGGACAAACC-3'

Airn R:
(SEQ ID NO: 139684)
5'-AGTGAGATCCAGGGATGCAG-3'

Kcnq1ot1 F:
(SEQ ID NO: 139685)
5'-ACTCGGAATTCAGGTGTGGG-3'

Kcnq1ot1 R:
(SEQ ID NO: 139686)
5'-GGTTGGAGGTCACCACAACAT-3'

Nespas F:
(SEQ ID NO: 139687)
5'-AGATGAGTCCAGGTGCTT-3'

Nespas R:
(SEQ ID NO: 139688)
5'-CAAGTCCAGAGTAGCCAAC-3'

UV-Crosslink RNA Immunoprecipitation

UV-RIP was performed as previously reported (Jeon and Lee, 2011). $1 \times 10^7$ day 3 female ES cells were trypsinized and resuspended in PBS. Cells for +UV experiments were crosslinked with 256 nm UV in a 15-cm dish at 250 mJ/cm$^2$ using the Stratalinker 1800 (Stratagene). ±UV cell pellets were resuspended in 1 mL of UV-RIP Nuclear Isolation Buffer (10 mM HEPES pH 7.5, 1.5 mM MgCl$_2$, 10 mM KCl, 0.5 mM DTT, protease inhibitors) for 30 min at 4° C., after which NP40 was added to a final concentration of 0.1% and incubated for an additional 10 min at 4° C. Nuclei were pelleted and lysed in 1 mL Lysis Buffer (1×PBS, 1% NP40, 0.5% sodium deoxycholate, protease and RNase inhibitors) for 25 min at 4° C., then for 15 min at 37° C. with 30 U TURBO DNase (Ambion) added. Lysates were spun down at 13,000 rpm at 4° C. for 10 min, and 5 μg of either αCTCF or IgG was added to the cleared lysate and incubated at 4° C. overnight with rotation, saving 5% lysate as input. 40 μL of Dynabeads Protein G per IP was pre-washed 3× with Lysis Buffer, added to the lysate-antibody mixture, and incubated for 2 hr at 4° C. to capture the RNA-protein-antibody complexes. Beads were washed 3× with high salt Wash Buffer I (Lysis Buffer supplemented with 150 mM NaCL, to a total of 300 mM), once with 1× TURBO DNase buffer, then treated with 100 U/mL TURBO DNase at 37° C. for 30 min in TURBO DNase buffer containing fresh protease and RNase inhibitors. Beads were further washed 2× with Wash Buffer I supplemented with 10 mM EDTA to quench DNase activity, then 2× with low salt Wash Buffer II (50 mM Tris-HCl pH 7.5, 1% NP40, 0.5% sodium deoxycholate, 50 mM NaCl, 10 mM EDTA), and finally treated with 100 μg proteinase K in 200 μL of proteinase K buffer (100 mM Tris-HCl pH 7.5, 50 mM NaCl, 10 mM EDTA, 0.5% SDS) for 30 min at 50° C. RNA was isolated by TRIzol extraction and used in strand-specific qRT-PCR with the following primers, in addition to primers listed under in vitro pulldown assay:

Gapdh F:
(SEQ ID NO: 139689)
5'-ATGAATACGGCTACAGCAACAGG-3'

Gapdh R:
(SEQ ID NO: 139690)
5'-CTCTTGCTCAGTGTCCTTGCTG-3'

Xite1 F:
(SEQ ID NO: 139691)
5'-GTCCACACTCCGCCAGCA-3'

Xite1 R:
(SEQ ID NO: 139692)
5'-TTAGGACAGAGTGAAAATCCGGAAGTTGT-3'

Xite2 F:
(SEQ ID NO: 139693)
5'-CCTATTACAACTATTACTCCATGCTACAACTTCTGG-3'

Xite2 R:
(SEQ ID NO: 139694)
5'-GGCATCTGATTCTCTCTTTCATTGTCCATG-3'

Tsix1 F:
(SEQ ID NO: 139695)
5'-CTCAAGAGCCTTAGGTCCCGC-3'

Tsix1 R:
(SEQ ID NO: 139696)
5'-AAGTGTGTAGCGCTTGCAGGTAC-3'

Tsix2 F:
(SEQ ID NO: 139697)
5'-TGAGATGCGGGCTAAGGAGAGG-3'

Tsix2 R:
(SEQ ID NO: 139698)
5'-CTGAAAGCACTTTGCCACTGTCCC-3'

Tsix3 F:
(SEQ ID NO: 139699)
5'-ACAGTGGAGCGATGGCTACGT-3'

Tsix3 R:
(SEQ ID NO: 139700)
5'-CTTCATCTCCGCATAGCTGGCAA-3'

Tsix4 F:
(SEQ ID NO: 139701)
5'-TCTGGGAACTTCTACCTGATCCTCACAT-3'

Tsix4 R:
(SEQ ID NO: 139702)
5'-AACTAGAAACAGGCAGTTAAGGTCCAAGG-3'

Tsix5 F:
(SEQ ID NO: 139703)
5'-CTTCTACTTGGACAAACCATGTATCGCTCC-3'

Tsix5 R:
(SEQ ID NO: 139704)
5'-TCCCAAGGTATGGAGTCACCAGG-3'

JpxE1 F:
(SEQ ID NO: 139705)
5'-AGGCTTCTGTAACTTATAAAATGGCGGC-3'

JpxE1 R:
(SEQ ID NO: 139706)
5'-CAGGGCATGTTCATTAATTGGCCAGT-3'

JpxE2 F:
(SEQ ID NO: 139707)
5'-CATTAATCCACCACTGAAGGAAGTCAGAGC-3'

JpxE2 R:
(SEQ ID NO: 139708)
5'-AGGTGAGCCAGCAAGCCGTATT-3'

U1 F:
(SEQ ID NO: 139709)
5'-CCAGGGCGAGGCTTATCCATT-3'

U1 R:
(SEQ ID NO: 139710)
5'-GCAGTCCCCCACTACCACAAAT-3'

RNA EMSA

RNA EMSA was performed as previously described (Sun et al., 2013). Briefly, probes were in vitro transcribed with T7 RNA polymerase (Ambion) from PCR-amplified cDNA template or linearized plasmids with cloned Xist RepA or RepF sequences. Transcripts were TURBO DNase treated, TRIzol purified, 5'-dephosphorylated with alkaline phosphatase (New England Biolabs), labelled with [γ-$^{32}$P]ATP using T4 polynucleotide kinase (New England Biolabs), and cleaned with Microspin G-50 columns. Probes were denatured at 95° C. for 2 min, then cooled at 70° C. for 5 min, 37° C. for 15 min, room temperature for 15 min, and kept in folding buffer (50 mM NaCl, 2 mM MgCl$_2$) on ice. For binding reactions, RNA probes were incubated with recombinant proteins at room temperature for 30 min in binding buffer (total reaction volume 20 µL) containing 50 mM Tris-HCl pH 7.5, 150 mM NaCl, 5 mM MgCl$_2$, 0.1 mM ZnSO$_4$, 10% glycerol, 0.1% Tween-20, 1 mM DTT, 1 µg poly(dI-dC), 0.1 mM polyamine, 8U RNase inhibitor (Roche), and 1 µg yeast tRNA. Samples were resolved at 4° C. by TBE polyacrylamide gel electrophoresis and detected using storage phosphor screen and Typhoon scanner (Amersham).

PCR primers (unlisted primers same as those for in vitro pulldown/UV-RIP):

```
T7_Neat1 F,
                                    (SEQ ID NO: 139711)
5'-TAATACGACTCACTATAGTGAGTGCTTTGCCACTGAAT-3'

T7_Nespas F,
                                    (SEQ ID NO: 139712)
5'-TAATACGACTCACTATAGAGATGAGTCCAGGTGCTT-3'

T7_Gapdh F,
                                    (SEQ ID NO: 139713)
5'-TAATACGACTCACTATAGATGAATACGGCTACAGCAACAGG-3'

T7_GtL2_2 F,
                                    (SEQ ID NO: 139714)
5'-TAATACGACTCACTATAGGGTGCTGGTGGATCGTTAAT-3'

GtL2_2 R,
                                    (SEQ ID NO: 139715)
5'-CTCCACTCCCTATTGCTTTCTATC-3'

T7_Xite F,
                                    (SEQ ID NO: 139716)
5'-TAATACGACTCACTATAGGAAGTGTGTGAGCAGAGTAAGG-3'

Xite R,
                                    (SEQ ID NO: 139717)
5'-GATGCGTGAAGACCCATGAA-3'

T7_Tsix_ex1F,
                                    (SEQ ID NO: 139718)
5'-TAATACGACTCACTATAGACAAGGTCCATGCTCTGTTCC-3'

T7_Tsix_ex1_mF,
                                    (SEQ ID NO: 139719)
5'-TAATACGACTCACTATAGGCAAGCGCTACACACTTGCG-3'

Tsix_ex1_mR,
                                    (SEQ ID NO: 139720)
5'-TTGCAGGTACTTTTGGGACC-3'

Tsix_ex1_mR2,
                                    (SEQ ID NO: 139721)
5'-AAGATGCGTGGATATCTCGG-3'

Tsix_ex1R,
                                    (SEQ ID NO: 139722)
5'-TTAGCCCGCATCTCACCCAC-3'

T7_Jpx_ex1F,
                                    (SEQ ID NO: 139723)
5'-TAATACGACTCACTATAGACGGCACCACCAGGCTTCT-3'

Jpx_ex3R,
                                    (SEQ ID NO: 139724)
5'-GAGTTTATTTGGGCTTACAGTTC-3'
```

Primer combination for Tsix RNA EMSA probes:
a, T7_Tsix_ex1F×Tsix_ex1_mR;
b, T7_Tsix_ex1 mF×Tsix_ex1R;
c, T7_Tsix_ex1F×Tsix_ex1_mR2;
d, T7_Tsix_ex1F×Tsix_ex1R.

Generation of shRNA Knockdown Lines

Wild-type male J1 (40XY) and female EL16.7 (40XX) ES cell lines and culture conditions have been previously described (Lee and Lu, 1999). Stable knockdown cell lines were generated by linearizing a pLKO.1-based vector containing shRNAs against Tsix, transfecting the DNA into J1 and EL16.7 cells using Lipofectamine 2000 (Invitrogen), and selecting for clones in 1 µg/mL puromycin for 7-9 days. Control cell lines containing a scrambled shRNA were also generated in parallel.

shRNA sequences were as follows: shTsix3 sense, 5'-GAAATAACCTCCAGAGAAATG-3' (SEQ ID NO: 139725); shTsix3 antisense, 5'-CTTTATTG-GAGGTCTCTTTAC-3' (SEQ ID NO: 139726); shScr sense, 5'-CCTAAGGTTAAGTCGCCCTCG-3' (SEQ ID NO: 139727); shScr antisense, 5'-CGAGGGCGACT-TAACCTTAGG-3' (SEQ ID NO: 139728).

Each cell line was differentiated for 6-8 days using suspension cultures forming embryoid bodies (EBs) at a starting concentration of ~5×10$^5$ cells/60 cm$^2$ as described (Ahn and Lee, 2010). At day 4, EBs were plated onto 0.2% gelatinized tissue culture plates for outgrowth. LIF (leukemia inhibitory factor) was removed from the differentiation medium, and culture medium was changed every two days. All experiments were performed three times. Viable cells were counted using a Cellometer Auto cell counter (Nexcelom Biosciences). Images were taken with a Nikon Eclipse TE2000-E inverted microscope.

Transient Knockdown by Antisense LNA

Antisense LNA oligonucleotides were obtained from Exiqon, Corp., and used for Tsix RNA knockdown. LNAs were delivered into female EL16.7 (40XX) ES cell line using Amaxa Biosystems Nucleofector and Mouse ES Cell Nucleofector Kit (Lonza). 2×10$^7$ trypsinized cells on d0, d3 and d6 were processed with 2 uM LNA using A-24 program. Cells were collected 6h or 12h later. LNA knockdown was confirmed by qRT-PCR using the following primers: TsixCf and TsixCr (see below); Tsix-F2, 5'-GTACGT-TACTCGCTAGCAGTAAT-3' (SEQ ID NO: 139729) and Tsix-R2, 5'-ATCCTTTGATTTTCTAATACCC-3' (SEQ ID NO: 139730); b-actin F, 5'-TTCTTTGCAGCTCCTTCGTT-3' (SEQ ID NO: 139731) and b-actin R, 5'-ATGGAGGG-GAATACAGCCC-3' (SEQ ID NO: 139732) LNA sequences are as follows: Tsix antisense LNA1, 5'-ACT-ACGCAGGCATTTT-3' (SEQ ID NO: 139733); Tsix antisense LNA2, 5'-GTATGGAGTCACCAGGTT-3' (SEQ ID NO: 139734); Scr LNA, 5'GTGTAACACGTC-TATACGCCCA-3' (SEQ ID NO: 139735).

Chromatin Immunoprecipitation

ChIP analyses were carried out using a modified protocol from Millipore as described (Ahn and Lee, 2010). Briefly, 1-2×10$^7$ cells were trypsinized and crosslinked with formaldehyde to a final concentration of 1% at 37° C. for 10 min. Crosslinking was quenched with glycine (125 mM final), and cells were pelleted at 640×g for 5 min and washed twice with 1×PBS containing protease inhibitors. Nuclei were isolated from fixed cells by washing once with Buffer A-NP40 (5 mM PIPES pH 8, 85 mM KCl, 0.5% NP40), incubated on ice for 10 min, then washed with Buffer A (5 mM PIPES pH 8, 85 mM KCl) and Lysis Buffer (10 mM Tris-HCl pH 8, 10 mM NaCl, 3 mM MgCl$_2$, 0.5% NP40). Pelleted nuclei were resuspended in MNase buffer (10 mM Tris-HCl pH 8, 10 mM NaCl, 3 mM MgCl$_2$, 1 mM CaCl$_2$), 4% NP40) containing protease inhibitors and 1% SDS. Lysates were sonicated using the Diagenode Bioruptor XL (15 min total with 30 s on and 30 s off cycles). Sonicated lysates were cleared at 16,100×g for 10 min. For each immunoprecipitation, 50 µL of Dynabeads Protein G were first incubated with 5 µg of either αCTCF, αOCT4 (Santa Cruz sc8628) or IgG for 2 hr with rotation, then with sonicated supernatants (~2.0×10$^6$ cells) overnight. IP samples were washed 2× each with Low Salt TSE 150 Buffer (20 mM Tris-HCl pH 8, 0.1% SDS, 1% Triton X-100, 2 mM EDTA, 150 mM NaCl), High Salt TSE 500 Buffer (20 mM Tris-HCl pH 8, 0.1% SDS, 1% Triton X-100, 2 mM EDTA, 500 mM NaCl), LiCl Buffer (10 mM Tris-HCl pH 8, 250 mM LiCl, 1% NP40, 1% deoxycholate, 1 mM EDTA), and TE Buffer (10 mM Tris-HCl pH 8, 1 mM EDTA). Protein-antibody complexes were eluted from the beads with freshly made Elution Buffer (50 mM Tris-HCl pH 8, 1 mM EDTA, 1% SDS, 50 mM NaHCO$_3$) incubated at 65° C. for 10 min. Crosslinks were reversed by digestion with 80 µg proteinase K at 65° C. for 4 hrs, and DNA was recovered by phenol/chloroform extraction and used for qPCR with the following primers (Xu et al., 2007; Donohoe et al., 2009; Navarro et al., 2010):

TsixAf, 5'-GTGTGTCATAGCTCAAGAGG-3' (SEQ ID NO: 139736)
TsixAr, 5'-GGAGCCTAAACCTGTCTGTC-3' (SEQ ID NO: 139737)
TsixCf, 5'-AATGCTTGCCAGCTATGCGG-3' (SEQ ID NO: 139738)
TsixCr, 5'-TAACCACCTGTAAGGGACAG-3' (SEQ ID NO: 139739)
Xitep77 (XiteCf), 5'-CAAGGTTGG-GAACAAGGTATATCAGG-3' (SEQ ID NO: 139740)
Xitep78 (XiteCr), 5'-GGACAAGGGACAGAAGTGCT-TATTTTAC-3' (SEQ ID NO: 139741)
XiteAf, 5'-ATGGCTTTAAGTCTGTAGCACAA-3' (SEQ ID NO: 139742)
XiteAr, 5'-CAGCCTCTATTCAGCTAGACTCC-3' (SEQ ID NO: 139743)
RS14f, 5'-ACATTCCGGCTACACACAAG-3' (SEQ ID NO: 139744)
RS14r, 5'-TGGGTGTTATACCCGTGTAGG-3' (SEQ ID NO: 139745)
Xist f, 5'-AACCCTTTTAAGTCCACTGTAAAT TCC-3' (SEQ ID NO: 139746)
Xist r, 5'-TAGAGAGCCAGACAATGCTAAGCC-3' (SEQ ID NO: 139747)
H19F, 5'-GTCACTCAGGCATAGCATTC-3' (SEQ ID NO: 139748)
H19R, 5'-GTCTGCCGAGCAATATGTAG-3' (SEQ ID NO: 139749)
ICRnF, 5'-GAGCTCTAAGGGAGGCTCCG-3' (SEQ ID NO: 139750)
ICRnR, 5'-CATCATGGTGTCCTCACAGG-3' (SEQ ID NO: 139751)

TsixAf,
(SEQ ID NO: 139736)
5'-GTGTGTCATAGCTCAAGAGG-3'

TsixAr,
(SEQ ID NO: 139737)
5'-GGAGCCTAAACCTGTCTGTC-3'

TsixCf,
(SEQ ID NO: 139738)
5'-AATGCTTGCCAGCTATGCGG-3'

TsixCr,
(SEQ ID NO: 139739)
5'-TAACCACCTGTAAGGGACAG-3'

Xitep77 (XiteCf),
(SEQ ID NO: 139740)
5'-CAAGGTTGGGAACAAGGTATATCAGG-3'

Xitep78 (XiteCr),
(SEQ ID NO: 139741)
5'-GGACAAGGGACAGAAGTGCTTATTTTAC-3'

XiteAf,
(SEQ ID NO: 139742)
5'-ATGGCTTTAAGTCTGTAGCACAA-3'

XiteAr,
(SEQ ID NO: 139743)
5'-CAGCCTCTATTCAGCTAGACTCC-3'

RS14f,
(SEQ ID NO: 139744)
5'-ACATTCCGGCTACACACAAG-3'

RS14r,
(SEQ ID NO: 139745)
5'-TGGGTGTTATACCCGTGTAGG-3'

Xist f,
(SEQ ID NO: 139746)
5'-AACCCTTTTAAGTCCACTGTAAATTCC-3'

Xist r,
(SEQ ID NO: 139747)
5'-TAGAGAGCCAGACAATGCTAAGCC-3'

H19F,
(SEQ ID NO: 139748)
5'-GTCACTCAGGCATAGCATTC-3'

H19R,
(SEQ ID NO: 139749)
5'-GTCTGCCGAGCAATATGTAG-3'

ICRnF,
(SEQ ID NO: 139750)
5'-GAGCTCTAAGGGAGGCTCCG-3'

ICRnR,
(SEQ ID NO: 139751)
5'-CATCATGGTGTCCTCACAGG-3'

Pairing Analysis

Pairing was assayed as previously described (Xu et al., 2006). DNA FISH was performed using two X-linked probes (centromeric RP24 and pSx9-Xic) to exclude XO cells. Digital images were taken with a Nikon Eclipse 90i microscope (Nikon Instruments, Inc.) and processed using Volocity software (Improvision). X-X distances were normalized to the nuclear area as distinguished by DAPI staining of the DNA. Measurements in 3D and 2D were essentially identical because maximal z dimensions were small compared to maximal x and y (H. P. Chu and J. T. Lee, unpublished observations).

Fluorescence in Situ Hybridization (FISH)

RNA/DNA FISH was performed on ES cells as previously described (Lee and Lu, 1999) using double-stranded Xist or Chr. 2 telomeric (RP24-338B6) DNA probes labeled by nick-translation (Roche). Digital images were taken with a Nikon Eclipse 90i microscope (Nikon Instruments, Inc.) and processed using Volocity software (Improvision). Cells were counted and scored for the presence or absence of an Xist RNA cloud or checked for ploidy.

Example 1. The CTCF-RNA Interactome

We endeavored to define the CTCF-RNA interactome in mouse embryonic stem cell (mESC) and examine its relationship to genomic CTCF-binding sites. To investigate the CTCF-RNA interactome, we performed UV-crosslinking and immunoprecipitation followed by deep sequencing (CLIP-seq) in order to identify directly interacting transcripts (Ule et al., 2005). We modified the CLIP-seq protocol to optimize detection within nuclear CTCF preparations (FIG. 1A; see Methods above), and performed this modified CLIP protocol in a female mESC line expressing inducible FLAG-tagged CTCF at physiological levels. Although expression of FLAG-tagged CTCF was robust after induction, total CTCF expression was nearly equal before and after induction at both the mRNA and protein levels (FIG. 8A,B), suggesting that CTCF levels are under feedback regulation. CLIP was carried out on day 0 (d0) and day 3 (d3) of cell differentiation, with minus-UV controls in parallel. Resolution of the radiolabelled CLIP materials by SDS-PAGE revealed an enrichment above background, with Western blotting indicating CTCF-RNA complexes running slightly higher than the 70-86-kD CTCF monomer and the 150-170-kD dimeric form, consistent with the presence of crosslinked RNA fragments (FIG. 1B). To minimize degradation of RNA during the isolation procedure, we used sonication instead of limiting RNase digestion to fragment RNA and produce CLIP tags of ~200 nt, as shown by bioanalyzer traces of RNA isolated from CLIP membranes (FIG. 1C, top left panel), with cDNA libraries yielding a range of sizes consistent with the RNA profile (FIG. 1C, bottom left panel). An aliquot of the CLIP nuclear lysate was set aside prior to sonication for total nuclear RNA isolation and RNA-seq library preparation to provide a comparative expression baseline.

Figure 1D:
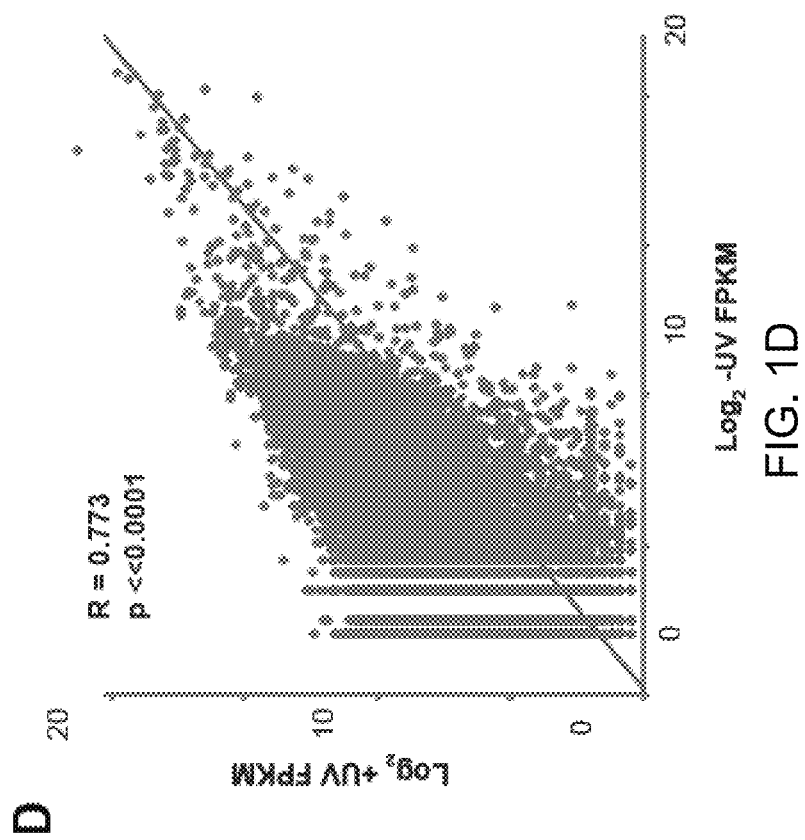
Figure 1E:
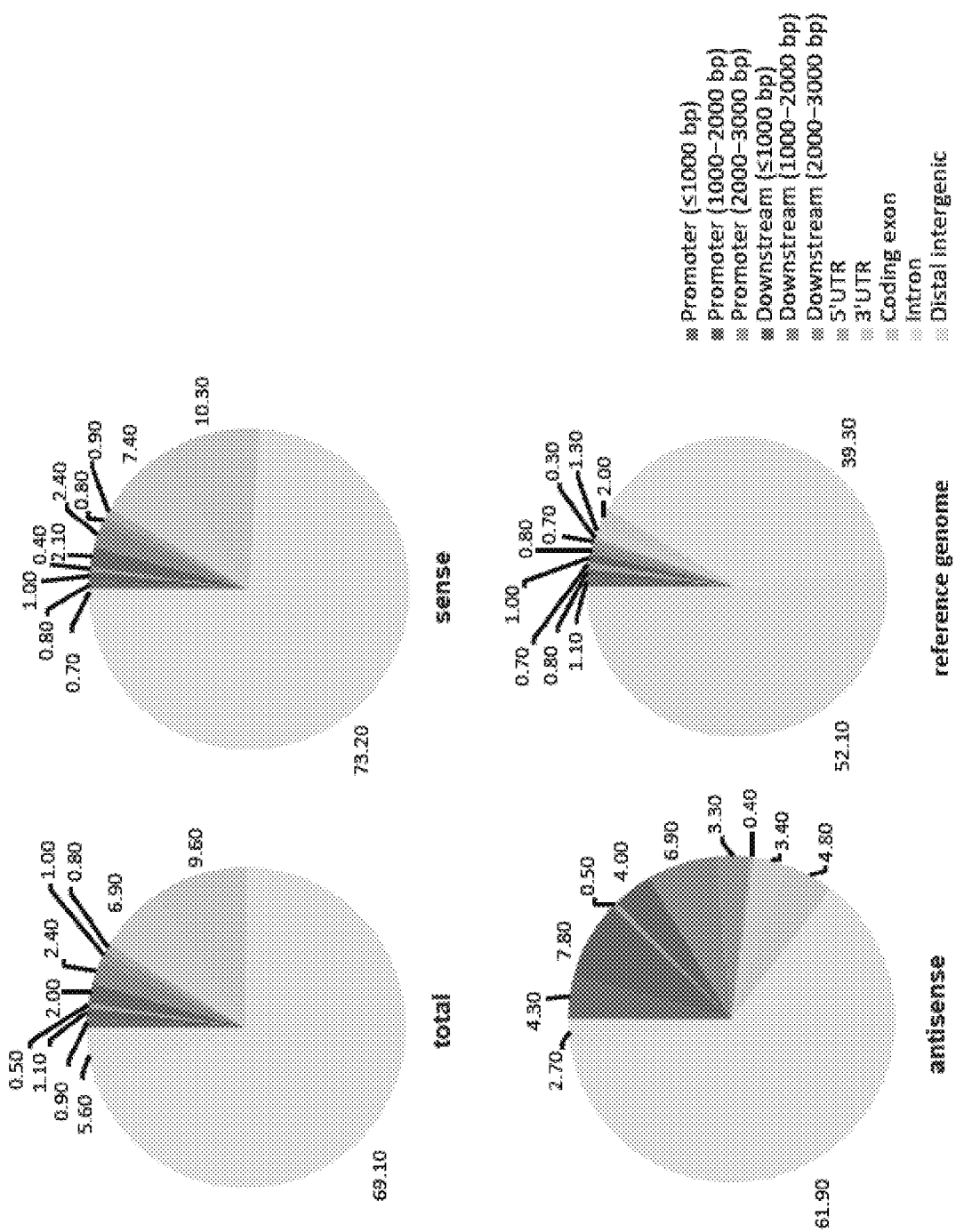

Approximately 200 million reads were obtained for each CLIP-seq (±UV) and RNA-seq libraries from two biological replicates of each sample. After removal of PCR duplicates, 40-50% of reads from the +UV libraries mapped to the mouse genome, resulting in libraries with high complexity; by contrast, only ~6% from control -UV libraries remained after removal of PCR duplicates, resulting in libraries with very low complexity (Table 3). Scatterplot analysis comparing +UV to -UV CLIP-seq reads revealed vast enrichment of RNA signal in the +UV library (FIG. 1D). Approximately a quarter of reads mapped more than once to the genome, of which 5-10% mapped to each of four well-characterized classes of repetitive elements, including LINEs, SINEs, LTRs, and simple repeats (FIG. 9A). Focusing on uniquely-aligned reads, the Piranha peak-caller software identified 100,000-200,000 statistically significant peaks (p<0.01, henceforth designated "peaks") when compared to the -UV CLIP controls. The CLIP peaks represented putative binding domains for the CTCF-RNA interactions. Using the Cis-regulatory Element Annotation System (CEAS), we determined the relative representation of CTCF CLIP peaks within genes and in intergenic space, excluding repetitive sequences. Around 90% of these peaks mapped within 3 kb of RefSeq-annotated gene loci. Thus, in mESC, RNA produced from 15,000 annotated genes are targets of CTCF. This large interactome is consistent with a recent analysis performed in a human osteosarcoma cell line using a different technique (Saldana-Meyer et al., 2014). In mESC, CTCF-interacting RNAs tend to reside within or near genes; in comparison to the reference genome, they appeared to localize preferentially to introns, exons, and 3' untranslated regions (UTR)(FIG. 1D). In addition to the forward strand of annotated genes, CLIP peaks were also identified on the reverse strand (Table 3; FIG. 1E, 9B), suggesting the existence of antisense transcripts that have not been annotated. Antisense RNAs accounted for 2.0-2.5% of peaks, corresponding to 2,000-3,000 loci. The remaining peaks were "intergenic," located outside of annotated genes (Table 3).

We then analyzed metagene profiles to examine the pattern of CTCF binding within the average interacting transcript. Interestingly, on the forward (sense) strand, CTCF binding sites trend towards greater enrichment near the 3' end at transcription termination site (TTS)(FIG. 2A,B, 9C, top panels), consistent with high enrichment within 3' UTRs (FIG. 1E, 9B). On the reverse (antisense) strand of RefSeq transcripts, enrichment was greatest within 1000 bp of the transcription start site (TSS) of the annotated sense gene (FIG. 2A,B, 9, bottom panels), indicating that CTCF preferred to bind the antisense transcript at a position upstream of the associated sense gene. Loci that produced CTCF-binding RNAs were not enriched in any noteworthy gene ontology (GO) terms, consistent with CTCF being a global transcriptional regulator. Analysis of CTCF CLIP peaks with the Multiple Em for Motif Elicitation (MEME) software also did not reveal a consensus motif, implying that CTCF recognizes RNA through secondary and/or tertiary structures, rather than through primary sequence.

Figure 2C:
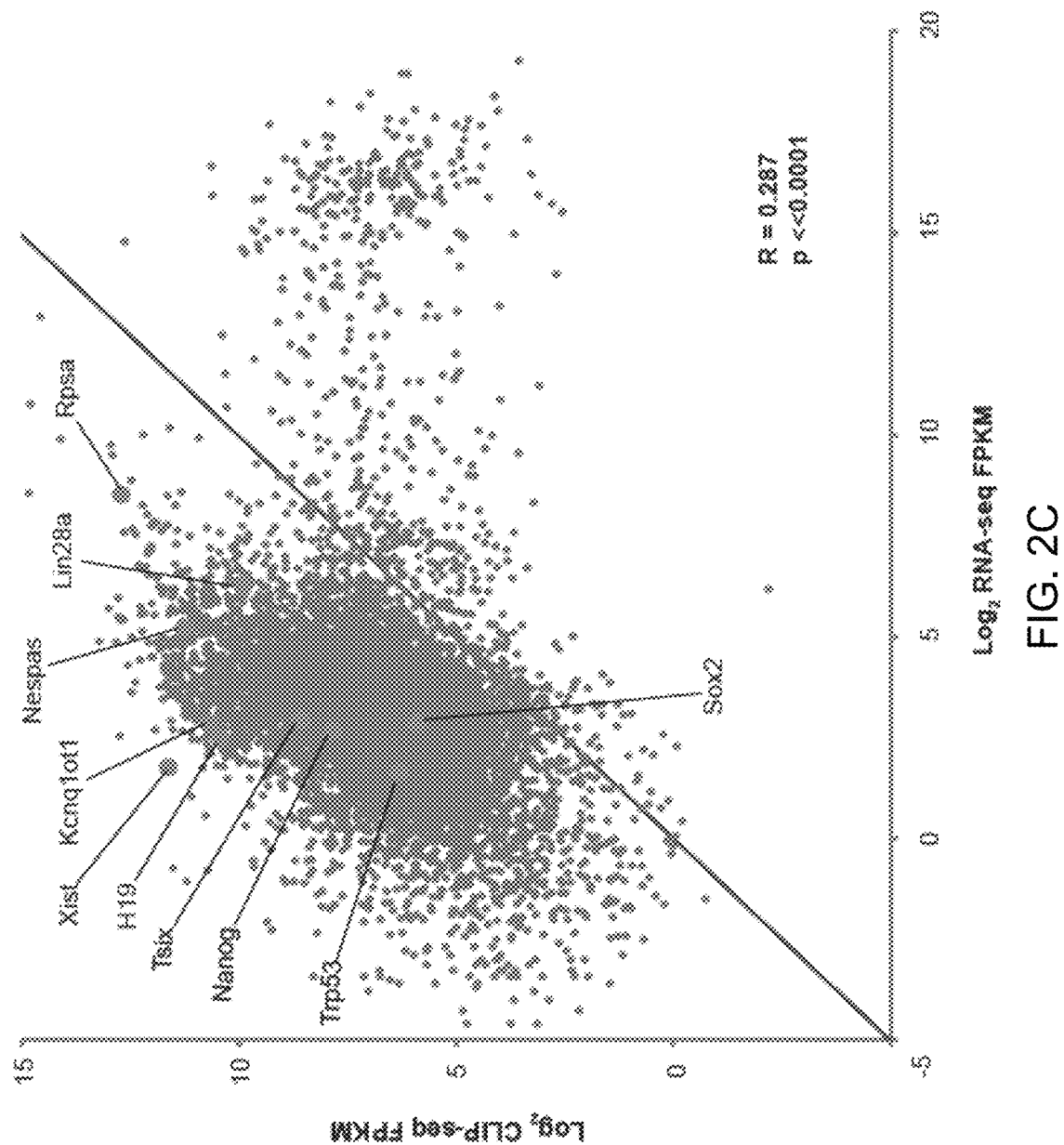

Because the CTCF CLIP peaks were highly enriched within genes, we sought to rule out the possibility of contamination by nuclear background. We therefore compared the CLIP-seq to nuclear RNA-seq profiles (FIG. 2C). If CTCF bound RNA nonspecifically or if our CLIP-seq method merely resulted in isolation of the nuclear RNA background, we would expect a random scatterplot in the case of nonspecific IP, or observe candidate transcripts residing along the diagonal in the case of nuclear RNA contamination. However, neither was the case. Indeed, we found a significant enrichment of hits in the transcripts of Table 3 ($R=0.287$, $p=2.94 \times 10^{-178}$). The proposed RNA interactome lay above the diagonal, inclusive of candidate interacting transcripts such as Tsix, Xist, Nespas, H19 and Kcnq1ot1. This data, together with the analysis comparing +UV to -UV libraries (FIG. 1D), argued against nonspecific interactions and substantial contamination by nuclear RNA. We conclude that CTCF has the capacity to interact directly with a great diversity of RNA in the mESC transcriptome.

The software UCSC Liftover was used to convert the empirically determined mouse mm9 coordinates to human hg19 to produce the sequences in Table 2.

Figure 2D:
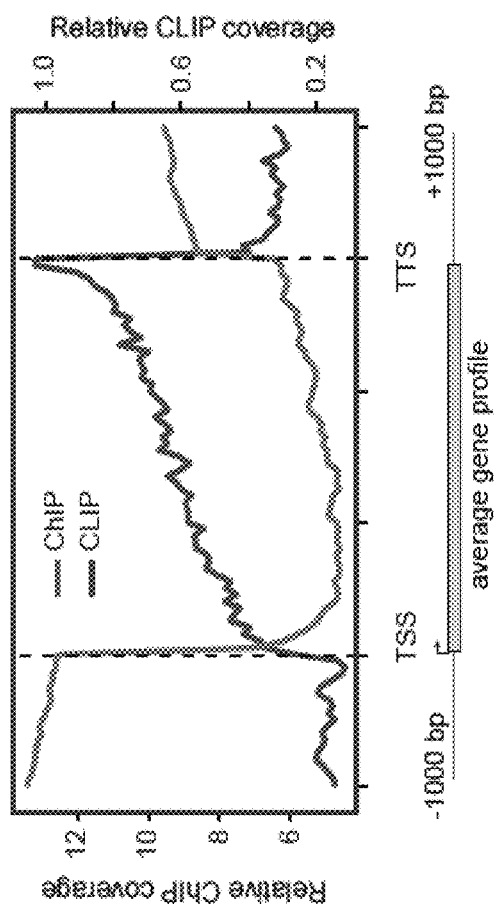
Figure 2E:
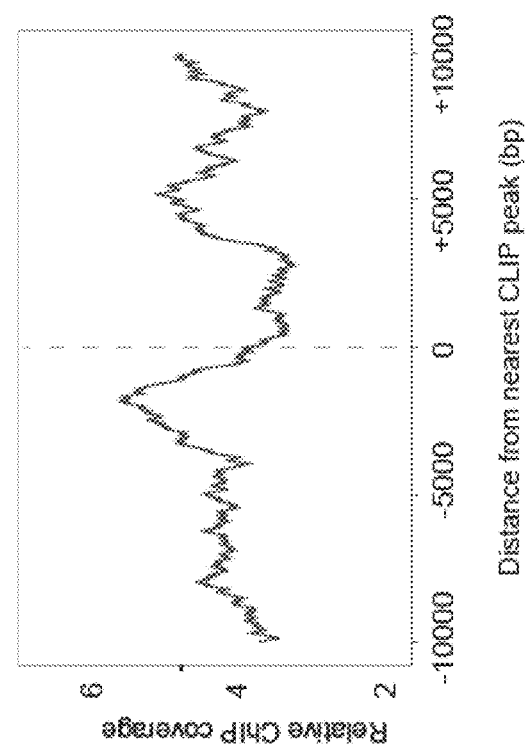

Example 2. Relationship Between the CTCF RNA Interactome and Epigenomic Landscape ChIP-seq analysis of CTCF has been reported in a number of recent publications (Xi et al., 2007; Heintzman et al., 2009; Calabrese et al., 2012). However, allelic profiling of the X-chromosome has not been carried out in female mESC during XCI. To investigate the relationship between the RNA interactome and the genomic CTCF landscape, we performed allele-specific ChIP-seq, with biological replicates, in d0 and d3 female mESCs (Table 4). Allele-specificity was made possible by a genetically marked hybrid female ES cell line carrying a disabled Tsix allele (Tsix$^{TST}$/+)(Ogawa et al., 2008), ensuring that the Xi (inactive X) will be the Mus musculus X-chromosome (mus) and Xa (active X) will be the Mus castaneus X (cas). Numerous polymorphisms between mus and cas enabled us to distinguish between CTCF ChIP signals from Xi and Xa (Pinter et al., 2012). Between 60-120 million reads were obtained for each ChIP-seq library, PCR duplicates were removed, and ChIP signals were normalized to input. Using the SPP software, we identified 45,000-48,000 CTCF DNA binding sites in d0 and d3 mESC, of which ~54% mapped within ±3 kb of Refseq annotated genes and the ~46% remaining reads mapped to intergenic space. Within genes, CTCF ChIP peaks could be observed within promoters, exons, introns, and 5' and 3' UTRs. However, metagene analysis indicated a preference for promoter regions (0-3 kb upstream of TSS) and the region immediately downstream of the TTS (0-3 kb downstream of TTS) (FIG. 2D).

located in close proximity to CTCF-interacting transcripts (FIG. 2E,F). Metagene analysis indicated that the CTCF-binding transcripts did not generally overlap the genomic binding sites (FIG. 2E). In fact, whereas CTCF tended to bind RNA sequences within gene bodies, it bound chromatin upstream of genes, preferentially in the promoter region and in regions immediately downstream of the TTS. We also examined the distance to the closest DNA-binding site (ChIP peak) from the typical RNA-binding site (CLIP peak) using a "metasite" analysis, and observed that DNA-binding sites occurred at greatest density around 2-kb upstream of the RNA-binding site, with a second concentration of ChIP sites 4000 bp downstream of the RNA-binding site (FIG. 2F). These data suggest that CTCF binds RNA and DNA at different locations, but the RNA- and DNA-binding sites tend to occur within 1-4 kb of each other.

To illustrate the aforementioned points about CTCF binding patterns, we examine specific genic loci. The locus for the Sox2 pluripotency factor harbors a distinct CTCF-DNA binding site upstream of its TSS and a robust CTCF-RNA interaction domain within the 3' UTR of the Sox2 transcript (FIG. 3A). Notably, the CLIP-seq profile did not resemble the RNA-seq profile; in fact, they were opposite of each other, with CLIP-seq peaks concentrated in the 3' UTR, and RNAseq reads showing highest coverage in the coding region (FIG. 3A). Positive controls further confirmed CLIP-seq specificity. For example, human SRA1 RNA was previously found to associate with a protein complex containing CTCF (Yao et al., 2010). Here, our CLIP-seq analysis demonstrated that the interaction is direct and that mouse Sra1 RNA contacts CTCF via its 3$^{rd}$ exon (FIG. 3B, significant peak in exon 3 [red bar]). Furthermore, binding of CTCF to Jpx RNA was previously shown to require exons 1-3 of Jpx (Sun et al., 2013). Our CLIP-seq analysis not only verified direct CTCF-Jpx interactions but also revealed that contact points occur predominantly within exon 3 (FIG. 3C). As for Sox2 RNA, the CLIP-seq profiles for Jpx and Sra1 were distinct from their RNA-seq profile. In contrast to Sox2, no CTCF-DNA interactions (ChIPseq peaks) were found within either the Jpx or Sra1 locus, consistent with the idea that Jpx and Sra1 RNA act in trans upon targets located at a distance from the site of synthesis (Lanz et al., 1999; Sun et al., 2013).

TABLE 3

Reads and peaks statistics for CTCF CLIP-seq and RNA-seq.

| | | CLIP-seq | | | | | | RNA-seq | |
|---|---|---|---|---|---|---|---|---|---|
| | | d0 rep1 | | d0 rep2 | | d3 | | | |
| | | +UV | −UV | +UV | −UV | +UV | −UV | d0 | d3 |
| reads | total | $2.18 \times 10^8$ | $1.99 \times 10^8$ | $2.19 \times 10^8$ | $2.12 \times 10^8$ | $1.97 \times 10^8$ | $2.28 \times 10^8$ | $2.50 \times 10^8$ | $1.83 \times 10^8$ |
| | with PCR duplicates removed | $2.90 \times 10^7$ | $1.64 \times 10^7$ | $3.35 \times 10^7$ | $1.77 \times 10^7$ | $2.81 \times 10^7$ | $2.20 \times 10^7$ | $4.74 \times 10^7$ | $3.48 \times 10^7$ |
| | uniquely aligned (% total reads; % cleaned-up reads) | $1.15 \times 10^7$ (5.26%; 39.52%) | $1.0 \times 10^6$ (0.53%; 6.43%) | $1.57 \times 10^7$ (7.19%; 47.00%) | $1.17 \times 10^6$ (0.55%; 6.62%) | $1.06 \times 10^7$ (5.40%; 37.81%) | $1.28 \times 10^6$ (0.56%; 5.83%) | $2.94 \times 10^7$ (11.75%; 61.93%) | $2.04 \times 10^7$ (11.16%; 58.70%) |
| peaks | total | 114016 | | 213183 | | 106382 | | | |
| | within annotated genes (+/−3b) | 101876 | | 190387 | | 96857 | | | |
| | no. of loci mapped to antisense to annotated genes | 15301 2716 | | 17107 5094 | | 14928 2137 | | | |
| | no. of loci mapped to intergenic | 2062 (1386 overlap with sense) 9424 | | 3137 (2394 overlap with sense) 17702 | | 2137 (1222 overlap with sense) 7388 | | | |

TABLE 4

Reads and peaks statistics for CTCF ChIP-seq.

| | | ChIP-seq | | | |
|---|---|---|---|---|---|
| | | d 0 | | d 3 | |
| | | input | IP | input | IP |
| reads | total | $1.27 \times 10^8$ | $9.86 \times 10^7$ | $9.40 \times 10^7$ | $6.66 \times 10^7$ |
| | with PCR duplicates removed | $1.01 \times 10^8$ | $6.76 \times 10^7$ | $8.34 \times 10^7$ | $5.66 \times 10^7$ |
| | aligned (% of total reads) | $8.69 \times 10^7$ (68.67%) | $5.79 \times 10^7$ (58.66%) | $7.21 \times 10^7$ (76.73%) | $4.82 \times 10^7$ (72.32%) |
| peaks | total | | 48495 (cas: 2932; mus: 26052) | | 45264 (cas: 2533; mus: 25170) |
| | % within annotated genes (+/− 3 kb) | | 53.3% | | 54.9% |
| | % intergenic | | 46.6% | | 46.1% |

Figure 3D:
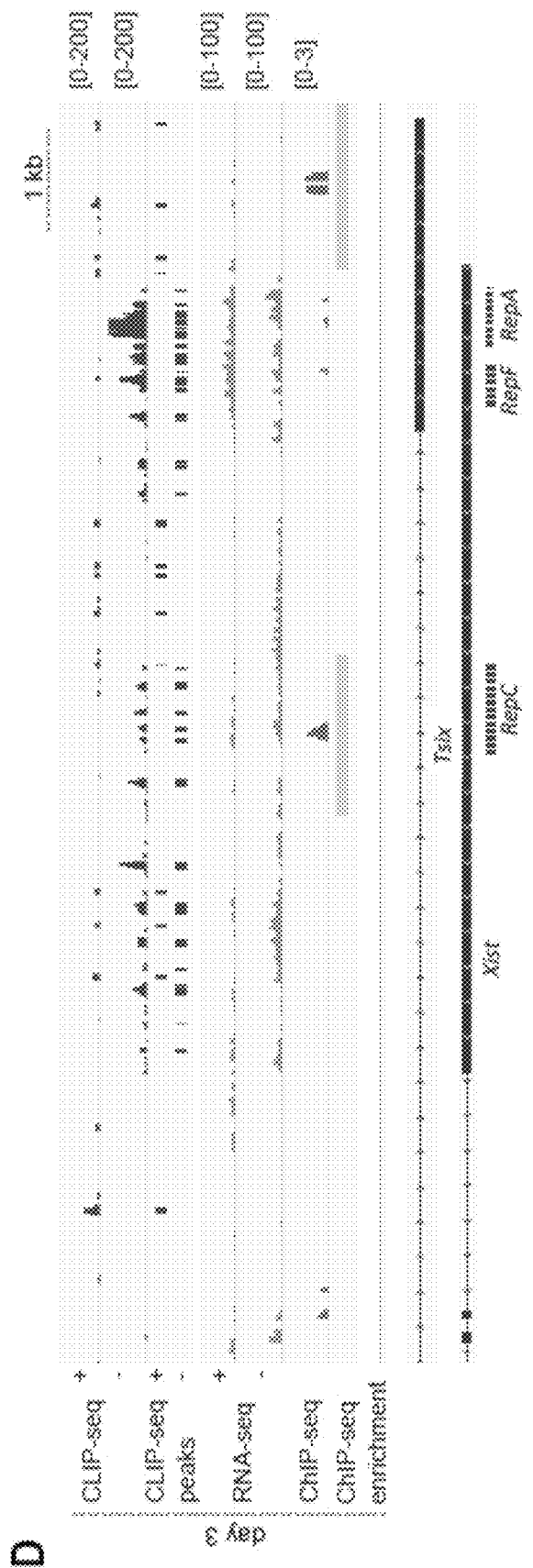
Figure 3E:
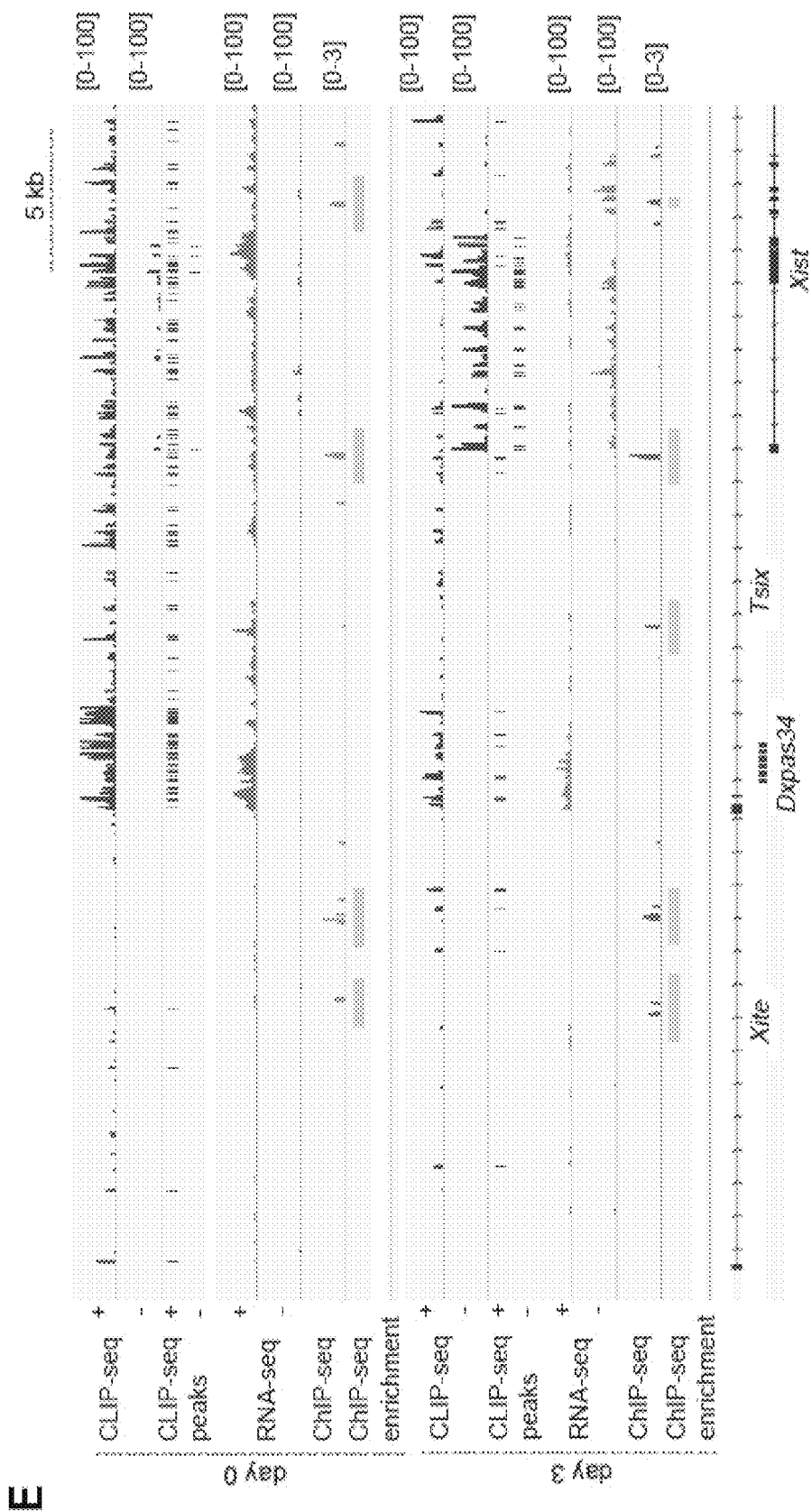

We then investigated the pattern of RNA binding (statistically significant CLIP-seq peaks) relative to DNA binding (statistically significant ChIP-seq peaks). Compared to CTCF-RNA interactions, CTCF-DNA interactions were more likely (46% vs. 5% of peaks) to occur in intergenic space. Interestingly, however, DNA binding sites were often Analysis of the rest of the X-inactivation center revealed multiple sites of interaction within both RNA and DNA (FIG. 3D,E). Within Xist, CTCF-Jpx RNA interactions has been proposed to cause eviction of CTCF repressor from the Xist promoter near Repeat F (RepF)(Sun et al., 2013). Indeed, we observed CTCF-DNA interactions near RepF, but also at ~1 kb upstream of the TSS and within Repeat C (RepC) (FIG. 3D). Meanwhile, CLIP-seq showed highly significant CTCF-RNA interactions within Xist exon 1, with particularly strong interactions at RepA and RepC, where PRC2 and YY1 interact with Xist/RepA transcripts (Zhao et al., 2008; Jeon and Lee, 2011), as well as RepF (FIG. 3D). Within Tsix and Xite, multiple CTCF-binding sites within the DNA had been identified previously by ChIP-qPCR and electromobility shift assays (EMSA)(Chao et al., 2002; Donohoe et al., 2007; Donohoe et al., 2009) and were confirmed here by ChIP-seq (FIG. 3E). Intriguingly, CLIP-seq analysis now identified multiple significant binding peaks with Tsix and Xite RNA (FIG. 3E), the biological significance of which we explored below.

The Xi provides a complex epigenomic landscape harboring both genes that are subject to silencing and those that escape from XCI (Carrel and Willard, 2005; Li and Carrel, 2008; Yang et al., 2010; Berletch et al., 2011; Calabrese et al., 2012; Pinter et al., 2012; Mugford et al., 2014). Allelic-specific ChIP-seq analysis of female mouse trophoblast stem cells (TSC) previously revealed CTCF localization patterns in a cell type with imprinted paternal X-chromosome silencing (Calabrese et al., 2012). Interestingly, in TSCs, the majority of CTCF binding sites on Xi were shared with Xa; furthermore, although a modest positive correlation was observed for CTCF binding and escape from XCI (Calabrese et al., 2012), no specific structural features have been identified (Mugford et al., 2014). Because imprinted XCI is mechanistically distinct from random XCI (Heard and Disteche, 2006; Starmer and Magnuson, 2009; Wutz, 2011; Disteche, 2012; Lee and Bartolomei, 2013), here we investigated the allelic binding patterns on Xi versus Xa in mESC undergoing random XCI.

Polymorphic sequences between mus (Xi) and cas (Xa) enabled us to distinguish between different allelic CTCF ChIP signals (Pinter et al., 2012). Although the majority of CTCF ChIP peaks were allelically balanced (or lacked sequence polymorphisms) (FIG. 4A: see "composite" track, which contains the sum of all ChIP reads at indicated positions), those peaks that did have allelic bias revealed very different binding profiles for Xa versus Xi in mESC undergoing XCI (FIG. 4A,B; violet versus green bars)—this contrasted with the mostly identical profiles reported for Xa and Xi in TSC (Calabrese et al., 2012). Even among genes subject to XCI, the pattern of CTCF binding on Xa and Xi were dramatically different (FIG. 4B; green versus violet peaks). Allele-specific binding profiles for escapee genes were also notable. For example, Kdm6a and Mid1 exhibited Xi-specific CTCF peaks (FIG. 4C and data not shown), with an Xi-specific interacting transcript located in close proximity. As was the case throughout the genome (FIG. 2E,F), the DNA binding sites on Xi were frequently located in proximity to CTCF-interacting transcripts in cis (FIG. 4C; 10A-D).

Example 3. CTCF is a High-Affinity and Specific RNA-Binding Protein

The large RNA interactome for CTCF is reminiscent of Polycomb repressive complex 2 (PRC2), for which an interactome of many thousands of transcripts has been reported by RIP-seq (Zhao et al., 2010; WO 2012/065143; WO 2012/087983). Recent work demonstrated that, while PRC2 has high affinity for a variety of transcripts (Davidovich et al., 2013), it binds RNA specifically with a dissociation constant ($K_d$) of ~80 nM for its strongest targets (Cifuentes-Rojas et al., 2014). Given a similarly large RNA interactome for CTCF, we sought to determine the biochemical specificity and binding affinities between RNA and CTCF.

To confirm a direct interaction with candidate RNAs, we first performed in vitro pulldown experiments with purified recombinant FLAG-CTCF and a control FLAG-GFP protein. Candidate RNAs identified in the CLIP-seq data were specifically pulled down from total cellular RNA by the purified FLAG-CTCF, whereas the negative controls, Gt12-as and Ppia, were not pulled down by CTCF significantly (FIG. 5A). Moreover, the negative control pulldowns using FLAG-GFP protein did not result in enrichment of any RNA (FIG. 5A; green bars all at ~0). Next, we performed in vivo UV-crosslinking followed by RNA immunoprecipitation (UV-RIP) in wild-type d3 ESC using either control IgG or αCTCF antibodies against the endogenous CTCF protein. Once again, target RNAs were specifically enriched in αCTCF pulldowns in UV-crosslinked cells, as compared to αCTCF RIPs in non-UV-crosslinked cells and/or in IgG pulldowns in UV-crosslinked cells (FIG. 5B).

We also performed RNA electrophoretic mobility shift assays (EMSA) with recombinant FLAG-CTCF and control FLAG-GFP proteins (FIG. 5C), testing in vitro-transcribed RNA fragments based on binding patterns informed by CLIP-seq (FIG. 3). EMSA showed specific RNA-protein shifts that were abrogated by unlabelled competitors at 40× molar excess, while control FLAG-GFP protein did not shift any of the RNA fragments (FIG. 5D). These experiments showed that, like the positive control Jpx RNA, the test RNAs (Tsix, Xist RepF, and Xite) could all bind CTCF, whereas the negative control Gapdh RNA could not. The imprinted lncRNAs, Nespas and Gt12, were also shifted by CTCF, consistent with CLIP-seq data (FIG. 10A-D). To map specific RNA-protein interaction domains, we focused on the 5' 400-nt region of Tsix (Tsix-d), which was identified as a strong binding site by CLIP-seq (FIG. 3E) and also shifted robustly by CTCF in the EMSA (FIG. 5D). We observed that within fragment d, subfragment c, but not b or a, could bind CTCF (FIG. 5E). To map the RNA-binding domain of CTCF, we carried out EMSA using domain-specific CTCF peptides. Interestingly, the fragment containing the Zn-finger region—a known nucleic-acids interaction domain—did not bind RNA; rather, the C-terminal region gave a specific RNA shift (FIG. 5F).

Example 4. Tsix RNA Recruits CTCF and Directs X-Chromosome Pairing

The genome-wide association identified here between CTCF-binding DNA and RNA sequences may suggest a functional relationship between the two. At the p53 locus, it has been proposed that binding of CTCF to an overlapping antisense transcript, Wrap53, regulates expression of p53 (Saldana-Meyer et al., 2014). Here we asked if CTCF RNA interactions may have other functions in epigenetic regulation. The association between CTCF and Tsix RNA was of particular interest because previous work strongly hinted that RNA may be required for inter-chromosomal interactions between the two X-inactivation centers (Xu et al., 2007). Random XCI is modeled ex vivo by mESCs undergoing cell differentiation, during which they recapitulate X-chromosome counting, choice, and spreading of silencing by Xist RNA (Starmer and Magnuson, 2009; Wutz, 2011; Disteche, 2012; Lee and Bartolomei, 2013). Xist is in turn controlled by the antisense Tsix locus and by Xite, a Tsix enhancer located between the major and minor promoters of Tsix and that produces short eRNAs (enhancer-associated RNAs)(Lee, 1999; Sado et al., 2001; Ogawa and Lee, 2003; Stavropoulos et al., 2005). Together, Tsix and Xite not only control allelic expression of Xist RNA, but also induce X-chromosome pairing, a transient event restricted to the Xic and observed prior to Xist upregulation between days 2-4 of mESC differentiation (Bacher et al., 2006; Xu et al., 2006; Xu et al., 2007; Masui et al., 2011). Genetic analyses have shown that pairing depends on a 15-kb region encompassing Tsix and Xite (Xu et al., 2006; Xu et al., 2007)(FIG. 6A). Interestingly, X-X pairing is rapidly disrupted by POL-II inhibitors, suggesting that newly synthesized transcripts—potentially Tsix and Xite themselves—may be required for the interchromosomal interactions.

Given a known requirement for Tsix/Xite and CTCF in X-X pairing (Xu et al., 2007) and in light of CTCF interactions with Tsix/Xite RNA (FIG. 3E), we investigated the functional relationship between CTCF-Tsix and CTCF-Xite interactions. First, we performed in vivo UV-RIP analysis to confirm the domains of interaction identified by CLIP-seq (FIG. 3E). Indeed, the regions of Tsix/Xite RNAs interacted specifically and directly with CTCF protein in vivo (FIG. 6B). We then knocked down Tsix RNA in female mESC using various strategies, including transiently transfected siRNAs, stably expressed shRNAs, and locked nucleic acid (LNA) gapmer oligonucleotides (which access nuclear lncRNAs more effectively (Sarma et al., 2010)). Whereas all tested siRNAs and most shRNAs were ineffective (data not shown), one shRNA directed at the Xite enhancer (Ogawa and Lee, 2003) and the overlapping minor Tsix transcript (Sado et al., 2001) achieved ~85% KD (FIG. 6C) and two LNAs directed at the major Tsix transcript, achieved 60-90% KD (FIG. 6D,E). To investigate effects on X-X pairing, we performed DNA fluorescence in situ hybridization (FISH) and measured Tsix inter-allelic distances. Knocking down Tsix (TsixKD) at all three positions reduced the number of X-X pairs between days 2-6 of differentiation (d2-d6) when pairing normally takes place (FIG. 6C-E; 11A-C). By contrast, scrambled shRNA or LNA (ScrKD) did not have any effect. Because the shRNA and LNAs yielded similar results, we henceforth show experiments using cell lines expressing the stably transfected shRNA, as these cells were more amenable to long-term differentiation assays.

We hypothesized that Tsix RNA may function as a locus-specific recruiting tool to recruit CTCF and thereby direct X-X pairing. In TsixKD cells, chromatin immunoprecipitations (ChIPs) of CTCF and OCT4, two transcriptional activators of Tsix/Xite known to regulate X-X pairing (Xu et al., 2006; Xu et al., 2007), showed reduced occupancy of CTCF at binding sites XiteC, XiteA, TsixA, and RS14 and decreased binding of OCT4 to binding sites XiteC, XiteA, and TsixA (FIG. 7A,B). Effects on binding were specific to this region, as CTCF and OCT4 binding to other X-linked regions was not altered (FIG. 12A-B). Other chromatin epitopes (e.g., H3K27me3) were also not affected by the knockdown (FIG. 12A-B). Consistent with disrupted pairing, TsixKD female cells exhibited defective embryoid body (EB) outgrowth (FIG. 7C), in spite of appropriate downregulation of pluripotency factors which indicated initiation of cell differentiation (FIG. 7D). Neither ScrKD female cells nor TsixKD male cells exhibited these anomalies (FIG. 7C). We furthermore observed that Xist induction was compromised, as only 1-2% of cells show full Xist upregulation between d2-d6 (P=0.03, FIG. 7E). Taken together, our functional analysis demonstrates that Tsix RNA is required for pairing and that it acts in this context by recruiting CTCF to the pairing center.

Example 5. Human CTCF Binding Sites

Using the methods and criteria described above, CTCF binding sites and their associated caRNAs were also identified in human HEK 293 kidney cells. Using a HEK 293 cell line expressing a FLAG-tagged CTCF construct (MacPherson, M. J., Beatty, L. G., Zhou, W., Du, M., and Sadowski, P. D. (2009) Mol Cell Biol 29:714-25), CLIP was performed to generate a CTCF-RNA interactome as described above for mESCs. Briefly, UV-crosslinking and immunoprecipitation of RNA followed by high-throughput sequencing was used to identify Ctcf-interacting RNAs. Peaks were called from uniquely mapped reads using the software Piranha. To produce non-overlapping peaks, entries from independent experiments were merged, then each entry was expanded by 500 nucleotides on each end, and then remerged. Human (hg19) data were obtained from 2 biological replicates using HEK293 cells. Approximately 170 million reads were obtained, of which about 4 million mapped uniquely to the human genome, producing about 51,000 statistically-significant peaks, covering about 8500 genes (sense or antisense). The peaks (representing CTCF binding sites), plus 500 nucleotides on either end, are listed in Table 1.

REFERENCES

Ahn, J. Y., and Lee, J. T. (2010). Retinoic acid accelerates downregulation of the Xist repressor, Oct4, and increases the likelihood of Xist activation when Tsix is deficient. BMC Dev Biol 10, 90

Bacher, C. P., Guggiari, M., Brors, B., Augui, S., Clerc, P., Avner, P., Eils, R., and Heard, E. (2006). Transient colocalization of X-inactivation centres accompanies the initiation of X inactivation. Nat Cell Biol 8, 293-299

Bell, A. C., and Felsenfeld, G. (2000). Methylation of a CTCF-dependent boundary controls imprinted expression of the Igf2 gene. Nature 405, 482-485.

Berletch, J. B., Yang, F., Xu, J., Carrel, L., and Disteche, C. M. (2011). Genes that escape from X inactivation. Hum Genet 130, 237-245

Calabrese, J. M., Sun, W., Song, L., Mugford, J. W., Williams, L., Yee, D., Starmer, J., Mieczkowski, P., Crawford, G. E., and Magnuson, T. (2012). Site-specific silencing of regulatory elements as a mechanism of X inactivation. Cell 151, 951-963

Carrel, L., and Willard, H. F. (2005). X-inactivation profile reveals extensive variability in X-linked gene expression in females. Nature 434, 400-404

Chao, W., Huynh, K. D., Spence, R. J., Davidow, L. S., and Lee, J. T. (2002). CTCF, a candidate trans-acting factor for X-inactivation choice. Science 295, 345-347

Chen, H., Tian, Y., Shu, W., Bo, X., and Wang, S. (2012). Comprehensive identification and annotation of cell type-specific and ubiquitous CTCF-binding sites in the human genome. PLoS ONE 7, e41374

Cifuentes-Rojas, C., Hernandez, A., Sarma, K., and Lee, J. T. (2014). Regulatory interactions between RNA and Polycomb repressive complex 2. Molecular Cell ePub May 29, 2014

Davidovich, C., Zheng, L., Goodrich, K. J., and Cech, T. R. (2013). Promiscuous RNA binding by Polycomb repressive complex 2. Nature structural & molecular biology 20, 1250-1257

DeMare, L. E., Leng, J., Cotney, J., Reilly, S. K., Yin, J., Sarro, R., and Noonan, J. P. (2013). The genomic landscape of cohesin-associated chromatin interactions. Genome Res 23, 1224-1234

Disteche, C. M. (2012). Dosage compensation of the sex chromosomes. Annual review of genetics 46, 537-560

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380

Donohoe, M. E., Silva, S. S., Pinter, S. F., Xu, N., and Lee, J. T. (2009). The pluripotency factor Oct4 interacts with Ctcf and also controls X-chromosome pairing and counting. Nature 460, 128-132

Donohoe, M. E., Zhang, L. F., Xu, N., Shi, Y., and Lee, J. T. (2007). Identification of a Ctcf cofactor, Yy1, for the X chromosome binary switch. Mol Cell 25, 43-56

Filippova, G. (2008). Genetics and epigenetics of the multifunctional protein CTCF. Curr Top Dev Biol 80, 337-360

Filippova, G. N., Cheng, M. K., Moore, J. M., Truong, J.-P., Hu, Y. J., Nguyen, D. K., Tsuchiya, K. D., and Disteche, C. M. (2005). Boundaries between Chromosomal domains of X inactivation and escape bind CTCF and lack CpG methylation during early development. Dev Cell 8, 31-42

Handoko, L., Xu, H., Li, G., Ngan, C. Y., Chew, E., Schnapp, M., Lee, C. W., Ye, C., Ping, J. L., Mulawadi, F., et al. (2011). CTCF-mediated functional chromatin interactome in pluripotent cells. Nat Genet 43, 630-638

Hark, A. T., Schoenherr, C. J., Katz, D. J., Ingram, R. S., Levorse, J. M., and Tilghman, S. M. (2000). CTCF mediates methylation-sensitive enhancer-blocking activity at the H19/Igf2 locus. Nature 405, 486-489

Heard, E., and Disteche, C. M. (2006). Dosage compensation in mammals: fine-tuning the expression of the X chromosome. Genes Dev 20, 1848-1867

Heintzman, N. D., Hon, G. C., Hawkins, R. D., Kheradpour, P., Stark, A., Harp, L. F., Ye, Z., Lee, L. K., Stuart, R. K., Ching, C. W., et al. (2009). Histone modifications at human enhancers reflect global cell-type-specific gene expression. Nature 459, 108-112

Jensen, K. B., and R. B., D. (2008). CLIP: crosslinking and immunoprecipitation of in vivo RNA targets of RNA-binding proteins. Methods Mol Biol 488, 85-98

Jeon, Y., and Lee, J. T. (2011). YY1 Tethers Xist RNA to the Inactive X Nucleation Center. Cell 146, 119-133

Kanduri, C., Fitzpatrick, G., Mukhopadhyay, R., Kanduri, M., Lobanenkov, V., Higgins, M., and Ohlsson, R. (2002). A differentially methylated imprinting control region within the Kcnql locus harbors a methylation-sensitive chromatin insulator. J Biol Chem 277, 18106-18110.

Kharchenko, P. V., Tolstorukov, M. Y., and Park, P. J. (2008). Design and analysis of ChIP-seq experiments for DNA-binding proteins. Nat Biotech 26, 1351-1359

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biol 14, R36

Kim, T. H., Abdullaev, Z. K., Smith, A. D., Ching, K. A., Loukinov, D. I., Green, R. D., Zhang, M. Q., Lobanenkov, V. V., and Ren, B. (2007). Analysis of the vertebrate insulator protein CTCF-binding sites in the human genome. Cell 128, 1231-1245

Kung, J. T., Colognori, D., and Lee, J. T. (2013). Long noncoding RNAs: Past, present, and future. Genetics 193, 651-669

Lai, F., Orom, U. A., Cesaroni, M., Beringer, M., Taatjes, D. J., Blobel, G. A., and Shiekhattar, R. (2013a). Activating RNAs associate with Mediator to enhance chromatin architecture and transcription. Nature 494, 497-501

Lai, F., Ørom, U. A., Cesaroni, M., Beringer, M., Taatjes, D. J., Blobel, G. A., and Shiekhattar, R. (2013b). Activating RNAs associate with Mediator to enhance chromatin architecture and transcription. Nature 494, 497-501

Lanz, R. B., McKenna, N. J., Onate, S. A., Albrecht, U., Wong, J., Tsai, S. Y., Tsai, M. J., and O'Malley, B. W. (1999). A steroid receptor coactivator, SRA, functions as an RNA and is present in an SRC-1 complex. Cell 97, 17-27

Lee, J. T., and Bartolomei, M. S. (2013). X-Inactivation, Imprinting, and Long Noncoding RNAs in Health and Disease. Cell 152, 1308-1323

Lee, J. T., Davidow, L. S., and Warshawsky, D. (1999). Tsix, a gene antisense to Xist at the X-inactivation centre. Nat Genet 21, 400-404

Lee, J. T., and Lu, N. (1999). Targeted mutagenesis of Tsix leads to nonrandom X inactivation. Cell 99, 47-57

Li, H., Handsaker, B., Wysoker, A., Fennell, T., Ruan, J., Homer, N., Marth, G., Abecasis, G., Durbin, R., and 1000 Genome Project Data Processing Subgroup (2009). The Sequence Alignment/Map format and SAMtools. Bioinformatics 25, 2078-2079

Li, N., and Carrel, L. (2008). Escape from X chromosome inactivation is an intrinsic property of the Jaridlc locus. Proc Natl Acad Sci USA 105, 17055-17060

Li, T., Hu, J. F., Qiu, X., Ling, J., Chen, H., Wang, S., Hou, A., Vu, T. H., and Hoffman, A. R. (2008). CTCF regulates allelic expression of Igf2 by orchestrating a promoter-polycomb repressive complex 2 intrachromosomal loop. Mol Cell Biol 28, 6473-6482

Li, W., Notani, D., Ma, Q., Tanasa, B., Nunez, E., Chen, A. Y., Merkurjev, D., Zhang, J., Ohgi, K., Song, X., et al. (2013). Functional roles of enhancer RNAs for oestrogen-dependent transcriptional activation. Nature 498, 516-520

Licatalosi, D. D., Mele, A., Fak, J. J., Ule, J., Kayikci, M., Chi, S. W., Clark, T. A., Schweitzer, A. C., Blume, J. E., Wang, X., et al. (2008). HITS-CLIP yields genome-wide insights into brain alternative RNA processing. Nature 456, 464-469

Ling, J. Q., Li, T., Hu, J. F., Vu, T. H., Chen, H. L., Qiu, X. W., Cherry, A. M., and Hoffman, A. R. (2006). CTCF mediates interchromosomal colocalization between Igf2/H19 and Wsb1/Nf1. Science 312, 269-272

Lobanenkov, V. V., Nicolas, R. H., Adler, V. V., Paterson, H., Klenova, E. M., Polotskaja, A. V., and Goodwin, G. H. (1990). A novel sequence-specific DNA binding protein which interacts with three regularly spaced direct repeats of the CCCTC-motif in the 5' flaking sequence of the chicken c-myc gene. Oncogene 5, 1743-1753

Martin, M. (2011). Cutadapt removes adapter sequences from high-throughput sequencing reads. EMBnet J 17, 10-12

Masui, O., Bonnet, I., Le Baccon, P., Brito, I., Pollex, T., Murphy, N., Hupe, P., Barillot, E., Belmont, A. S., and Heard, E. (2011). Live-cell chromosome dynamics and outcome of X chromosome pairing events during ES cell differentiation. Cell 145, 447-458

Mugford, J. W., Starmer, J., Williams, R. L., Jr., Calabrese, J. M., Mieczkowski, P., Yee, D., and Magnuson, T. (2014). Evidence for Local Regulatory Control of Escape from Imprinted X Chromosome Inactivation. Genetics Nakahashi, H., Kwon, Resch, W., Vian, L., Dose, M., Stavreva, D., Hakim, O., Pruett, N., Nelson, S., Yamane, A., et al. (2013). A genome-wide map of CTCF multivalency redefines the CTCF code. Cell Rep 3, 1678-1689

Navarro, P., Oldfield, A., Legoupi, J., Festuccia, N., Dubois, A., Attia, M., Schoorlemmer, J., Rougeulle, C., Chambers, I., and Avner, P. (2010). Molecular coupling of Tsix regulation and pluripotency. Nature 468, 457-460

Nora, E. P., Lajoie, B. R., Schulz, E. G., Giorgetti, L., Okamoto, I., Servant, N., Piolot, T., van Berkum, N. L., Meisig, J., Sedat, J., et al. (2012). Spatial partitioning of the regulatory landscape of the X-inactivation centre. Nature 485, 381-385

Ogawa, Y., and Lee, J. T. (2003). Xite, X-inactivation intergenic transcription elements that regulate the probability of choice. Mol Cell 11, 731-743

Ogawa, Y., Sun, B. K., and Lee, J. T. (2008). Intersection of the RNA interference and X-inactivation pathways. Science 320, 1336-1341

Ohlsson, R., Lobanenkov, V., and Klenova, E. (2010). Does CTCF mediate between nuclear organization and gene expression? BioEssays: news and reviews in molecular, cellular and developmental biology 32, 37-50

Ohlsson, R., Renkawitz, R., and Lobanenkov, V. V. (2001). CTCF is a uniquely versatile transcription regulator linked to epigenetics and disease. Trends Genet 7, 520-527

Ong, C.-T., and Corces, V. G. (2014). CTCF: an architectural protein bridging genome topology and function. Nat Rev Genet 15, 234-246

Palstra, R. J., Tolhuis, B., Splinter, E., Nijmeijer, R., Grosveld, F., and de Laat, W. (2003). The β-globin nuclear compartment in development and erythroid differentiation. Nat Genet 35, 190-194

Phillips-Cremins, J. E., Sauria, M. E., Sanyal, A., Gerasimova, T. I., Lajoie, B. R., Bell, J. S., Ong, C. T., Hookway, T. A., Guo, C., Sun, Y., et al. (2013). Architectural protein subclasses shape 3D organization of genomes during lineage commitment. Cell 153, 1281-1295

Pinter, S. F., Sadreyev, R. I., Yildirim, E., Jeon, Y., Ohsumi, T. K., Borowsky, M., and T., L. J. (2012). Spreading of X chromosome inactivation via a hierarchy of defined Polycomb stations. Genome Res 22, 1864-1876

Quinlan, A. R., and Hall, I. M. (2010). BEDTools: a flexible suite of utilities for comparing genomic features. Bioinformatics 26, 841-842

Sado, T., Wang, Z., Sasaki, H., and Li, E. (2001). Regulation of imprinted X-chromosome inactivation in mice by Tsix. Development 128, 1275-1286

Saldana-Meyer, R., Gonzalez-Buendia, E., Guerrero, G., Narendra, V., Bonasio, R., Recillas-Targa, F., and Reinberg, D. (2014). CTCF regulates the human p53 gene through direct interaction with its natural antisense transcript, Wrap53. Genes Dev 28, 723-734

Sanyal, A., Lajoie, B. R., Jain, G., and Dekker, J. (2012). The long-range interaction landscape of gene promoters. Nature 489, 109-113

Sarma, K., Levasseur, P., Aristarkhov, A., and Lee, J. T. (2010). Locked nucleic acids reveal sequence requirements and kinetics of Xist RNA localization to the X chromosome. Proc Natl Acad Sci USA 107, 22196-22201

Shen, Y., Yue, F., McCleary, D. F., Ye, Z., Edsall, L., Kuan, S., Wagner, U., Dixon, J., Lee, L., Lobanenkov, V. V., et al. (2012). A map of the cis-regulatory sequences in the mouse genome. Nature 488, 116-120

Shin, H., Liu, T., Manrai, A. K., and Liu, X. S. (2009). CEAS: cis-regulatory element annotation system. Bioinformatics 19, 2605-2606

Spencer, R. J., B. C., d. R., Pinter, S. F., Lessing, D., Sadreyev, R. I., and Lee, J. T. (2011). A boundary element between Tsix and Xist binds the chromatin insulator Ctcf and contributes to initiation of X-chromosome inactivation. Genetics 189, 441-454

Splinter, E., Heath, H., Kooren, J., Palstra, R. J., Klous, P., Grosveld, F., Galjart, N., and de Laat, W. (2006). CTCF mediates long-range chromatin looping and local histone modification in the beta-globin locus. Genes Dev 20, 2349-2354

Starmer, J., and Magnuson, T. (2009). A new model for random X chromosome inactivation. Development 136, 1-10

Stavropoulos, N., Rowntree, R. K., and Lee, J. T. (2005). Identification of developmentally specific enhancers for Tsix in the regulation of X chromosome inactivation. Mol Cell Biol 25, 2757-2769

Sun, S., del Rosario, B. C., Szanto, A., Ogawa, Y., Jeon, Y., and Lee, J. T. (2013). Jpx RNA activates Xist by evicting CTCF. Cell 153, 1537-1551

Takahashi, K., Saitoh, S., and Yanagida, M. (2000). Application of the chromatin immunoprecipitation method to identify in vivo protein-DNA associations in fission yeast. Sci STKE 2000, pl1

Trapnell, C., Roberts, A., Goff, L., Pertea, G., Kim, D., Kelley, D. R., Pimentel, H., Salzberg, S. L., Rinn, J. L., and Pachter, L. (2012). Differential gene and transcript expression analysis of RNA-seq experiments with TopHat and Cufflinks. Nat Protocols 7, 562-578

Tsai, C. L., Rowntree, R. K., Cohen, D. E., and Lee, J. T. (2008). Higher order chromatin structure at the X-inactivation center via looping DNA. Dev Biol 319, 416-425

Ule, J., Jensen, K., Mele, A., and Darnell, R. B. (2005). CLIP: a method for identifying protein-RNA interaction sites in living cells. Methods 37, 376-386

Ule, J., Jensen, K. B., Ruggiu, M., Mele, A., Ule, A., and Darnell, R. B. (2003). CLIP identifies Nova-regulated RNA networks in the brain. Science 302, 1212-1215

Uren, P. J., Bahrami-Samani, E., Burns, S. C., Qiao, M., Karginov, F. V., Hodges, E., Hannon, G. J., Sanford, J. R., Penalva, L. O. F., and Smith, A. D. (2012). Site identification in high-throughput RNA-protein interaction data. Bioinformatics 28, 3013-3020

Wan, L. B., and Bartolomei, M. S. (2008). Regulation of imprinting in clusters: Noncoding RNAs versus insulators. Adv Genet 61, 207-223

Wutz, A. (2011). Gene silencing in X-chromosome inactivation: advances in understanding facultative heterochromatin formation. Nat Rev Genet 12, 542-553

Xi, H., Shulha, H. P., Lin, J. M., Vales, T. R., Fu, Y., Bodine, D. M., McKay, R. D., Chenoweth, J. G., Tesar, P. J., Furey, T. S., et al. (2007). Identification and characterization of cell type-specific and ubiquitous chromatin regulatory structures in the human genome. PLoS genetics 3, e136

Xu, N., Donohoe, M. E., Silva, S. S., and Lee, J. T. (2007). Evidence that homologous X-chromosome pairing requires transcription and Ctcf protein. Nat Genet 39, 1390-1396

Xu, N., Tsai, C. L., and Lee, J. T. (2006). Transient homologous chromosome pairing marks the onset of X inactivation. Science 311, 1149-1152

Yang, F., Babak, T., Shendure, J., and Disteche, C. M. (2010). Global survey of escape from X inactivation by RNA-sequencing in mouse. Genome Res 20, 614-622

Yao, H., Brick, K., Evrard, Y., Xiao, T., Camerini-Otero, R. D., and Felsenfeld, G. (2010). Mediation of CTCF transcriptional insulation by DEAD-box RNA-binding protein p68 and steroid receptor RNA activator SRA. Genes Dev 24, 2543-2555

Yeo, G. W., Coufal, N. G., Liang, T. Y., Peng, G. E., Fu, X. D., and Gage, F. H. (2009). An RNA code for the FOX2 splicing regulator revealed by mapping RNA-protein interactions in stem cells. Nat Struct Mol Biol 16, 130-137

Zhang, H., Niu, B., Hu, J. F., Ge, S., Wang, H., Li, T., Ling, J., Steelman, B. N., Qian, G., and A. R., H. (2011). Interruption of intrachromosomal looping by CCCTC binding factor decoy proteins abrogates genomic imprinting of human insulin-like growth factor II. J Cell Biol 193, 475-487

Zhao, J., Ohsumi, T. K., Kung, J. T., Y., O., D. J., G., Sarma, K., Song, J. J., Kingston, R. E., Borowsky, M., and Lee, J. T. (2010). Genome-wide identification of polycomb-associated RNAs by RIP-seq. Mol Cell 40, 939-953

Zhao, J., Sun, B. K., Erwin, J. A., Song, J. J., and Lee, J. T. (2008). Polycomb proteins targeted by a short repeat RNA to the mouse X chromosome. Science 322, 750-756

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Lengthy table referenced here

US11001841-20210511-T00001

Please refer to the end of the specification for access instructions.

Lengthy table referenced here

US11001841-20210511-T00002

Please refer to the end of the specification for access instructions.

Lengthy table referenced here

US11001841-20210511-T00003

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US11001841B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11001841B2). An electronic copy of the "Sequence Listing" will also be available from the USPTO upon request and payment of the fee set forth in 37 CFR 1.19(b)(3).

What is claimed is:

1. A method of activating an inactive X-linked allele in a cell, preferably a cell of a female heterozygous subject, the method comprising administering to the cell an inhibitory oligonucleotide targeting a sequence of at least 12 consecutive nucleotides within SEQ ID NOs:49590-49613, wherein CTCF binding to Jpx RNA is disrupted.

2. The method of claim 1, wherein the inactive X-linked allele is associated with an X-linked disorder, and the oligonucleotide is administered in a therapeutically effective amount.

3. The method of claim 1, wherein the cell is in a living subject.

4. The method of claim 1, wherein the inhibitory oligonucleotide is identical or complementary to at least 15 consecutive nucleotides of SEQ ID NOs:49590-49613.

5. The method of claim 1, wherein the oligonucleotide does not comprise three or more consecutive guanosine nucleotides.

6. The method of claim 1, wherein the oligonucleotide does not comprise four or more consecutive guanosine nucleotides.

7. The method of claim 1, wherein the oligonucleotide is 12 to 30 nucleotides in length.

8. The method of claim 1, wherein at least one nucleotide of the oligonucleotide is a nucleotide analogue or a 2' O-methyl.

9. The method of claim 1, wherein the oligonucleotide comprises at least one ribonucleotide, at least one deoxyribonucleotide, or at least one bridged nucleotide.

10. The method of claim 9, wherein the bridged nucleotide is a LNA nucleotide, a cEt nucleotide or a ENA modified nucleotide.

11. The method of claim 1, wherein one or more of the nucleotides of the oligonucleotide comprise 2'-fluoro-deoxyribonucleotides, one or more of the nucleotides of the oligonucleotide comprise 2'-O-methyl nucleotides, one or more of the nucleotides of the oligonucleotide comprise ENA nucleotide analogues, and/or one or more of the nucleotides of the oligonucleotide comprise LNA nucleotides.

12. The method of claim 1, wherein the nucleotides of the oligonucleotide comprise comprising phosphorothioate internucleotide linkages between at least two nucleotides or between all nucleotides.

13. The method of claim 1, wherein the nucleotides of the oligonucleotide comprise phosphorothioate internucleotide linkages between at least two nucleotides.

14. The method of claim 1, wherein the nucleotides of the oligonucleotide comprise phosphorothioate internucleotide linkages between all nucleotides.

15. The method of claim 1, wherein the oligonucleotide is a gapmer or a mixmer.

16. The method of claim 1, wherein the inactive X-linked allele is CDKL5, MECP2, or FMR1.

* * * * *

UNITED STATES PATENT AND TRADEMARK OFFICE
CERTIFICATE OF CORRECTION

| | | |
|---|---|---|
| PATENT NO. | : 11,001,841 B2 | Page 1 of 1 |
| APPLICATION NO. | : 15/952679 | |
| DATED | : May 11, 2021 | |
| INVENTOR(S) | : Jeannie T. Lee, Johnny Kung and Barry Kesner | |

It is certified that error appears in the above-identified patent and that said Letters Patent is hereby corrected as shown below:

In the Specification

Column 1, Line 16, delete "GM58839" and insert -- GM090278 --

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*